United States Patent
Pulé et al.

(10) Patent No.: US 10,800,854 B2
(45) Date of Patent: Oct. 13, 2020

(54) CHIMERIC CYTOKINE RECEPTORS AND ENCODING NUCLEIC ACIDS

(71) Applicant: AUTOLUS LIMITED, London (GB)

(72) Inventors: Martin Pulé, London (GB); Shaun Cordoba, London (GB); Matteo Righi, London (GB); James Sillibourne, London (GB); Shimobi Onuoha, London (GB); Simon Thomas, London (GB)

(73) Assignee: AUTOLUS LIMITED, London (GB)

( * ) Notice: Subject to any disclaimer, the term of this patent is extended or adjusted under 35 U.S.C. 154(b) by 73 days.

(21) Appl. No.: 15/753,486

(22) PCT Filed: Aug. 19, 2016

(86) PCT No.: PCT/GB2016/052564
§ 371 (c)(1),
(2) Date: Feb. 19, 2018

(87) PCT Pub. No.: WO2017/029512
PCT Pub. Date: Feb. 23, 2017

(65) Prior Publication Data
US 2018/0244797 A1 Aug. 30, 2018

(30) Foreign Application Priority Data
Aug. 20, 2015 (GB) .................................. 1514875.2

(51) Int. Cl.
| | | |
|---|---|---|
| C07K 16/30 | (2006.01) | |
| C07K 14/46 | (2006.01) | |
| A61K 39/00 | (2006.01) | |
| A61K 35/17 | (2015.01) | |
| C07K 14/715 | (2006.01) | |

(52) U.S. Cl.
CPC .......... *C07K 16/3069* (2013.01); *A61K 35/17* (2013.01); *A61K 39/0011* (2013.01); *A61K 39/001116* (2018.08); *A61K 39/001135* (2018.08); *A61K 39/001182* (2018.08); *A61K 39/001194* (2018.08); *C07K 14/46* (2013.01); *C07K 14/7155* (2013.01); *A61K 2039/5158* (2013.01); *A61K 2039/55522* (2013.01); *C07K 2317/56* (2013.01); *C07K 2317/622* (2013.01); *C07K 2319/70* (2013.01)

(58) Field of Classification Search
CPC ................ C07K 16/3069; C07K 14/46; C07K 14/7155; C07K 2317/56; C07K 2317/569; C07K 2317/622; C07K 2319/00; C07K 2319/70; A61K 35/17; A61K 39/0011; A61K 2039/5158; A61K 2039/55522; A61P 35/00; C12N 5/0636
See application file for complete search history.

(56) References Cited

U.S. PATENT DOCUMENTS

2013/0280220 A1  10/2013  Ahmed et al.

FOREIGN PATENT DOCUMENTS

| | | | |
|---|---|---|---|
| WO | WO-94/29458 A1 | 12/1994 | |
| WO | WO-2007/115230 A2 | 10/2007 | |
| WO | WO-2008/045437 A2 | 4/2008 | |
| WO | WO-2010/085660 A2 | 7/2010 | |
| WO | WO-2013/123061 A1 | 8/2013 | |
| WO | WO-2013123061 A1 * | 8/2013 | ......... C07K 16/2803 |
| WO | WO-2015/150771 A1 | 10/2015 | |
| WO | WO-2016/061574 A1 | 4/2016 | |

OTHER PUBLICATIONS

Sogo et al Journal of Immunol. Methods, 337, 16-23 (Year: 2008).*
Chinnasamy D, et al. (Mar. 15, 2012) Clinical Cancer Research. 18(6):1672-1683. (doi:10.1158/1078-0432.CCR-11-3050).*
Leen AM, et al. (Jun. 2014) Molecular Therapy. 22(6):1211-1220. (doi: 10.1038/mt.2014.47).*
Kawahara M, et al. (Apr. 1, 2007) The Journal of Biochemistry. 141(4):563-571. (https://doi.org/10.1093/jb/mvm056).*
Shirasu N and Kuroki M (2012) Anticancer Research. 32:2377-2384.*
Kawahara et al., "Mimicry of Erythropoietin and Interleukin-6 Signalling by an Antibody/Cytokine Receptor Chimera in Murine Myeloid 32D Cells," J. Biochem. 141:563-571 (2007).
Livnah et al., "Crystallographic Evidence for Preformed Dimers of Erythropoietin Receptor Before Ligand Activation," Science 283:987-990 (1999).
Abate-Daga et al., "A Novel Chimeric Antigen Receptor Against Prostate Stem Cell Antigen Mediates Tumor Destruction in a Humanized Mouse Model of Pancreatic Cancer," Human Gene Therapy, 25(12):1003-1012 (2014).
Bayat et al., "Production and Characterization of Monoclonal Antibodies against Human Prostate Specific Antigen," Avicenna J Med Biotechnol, 7(1):2-7 (2015).
Donnelly et al., "The 'cleavage' activities of foot-and-mouth disease virus 2A site-directed mutants and naturally occurring '2A-like' sequences," J Gen Virol, 82(5):1027-1041 (2001).
Guedan et al., "ICOS-based chimeric antigen receptors program bipolar TH17/TH1 cells," Blood, 124(7):1070-1080 (2014).

(Continued)

*Primary Examiner* — Robert S Landsman
(74) *Attorney, Agent, or Firm* — Marshall, Gerstein & Borun LLP

(57) ABSTRACT

The present invention provides a chimeric cytokine receptor (CCR) comprising: (i) an exodomain which binds to a ligand selected from a tumour secreted factor, a chemokine and a cell-surface antigen; and (ii) a cytokine receptor endodomain.

22 Claims, 11 Drawing Sheets
Specification includes a Sequence Listing.

(56) References Cited

OTHER PUBLICATIONS

Hassuneh et al., "Evidence for the Participation of Interleukin-2 (IL-2) and IL-4 in the Regulation of Autonomous Growth and Tumorigenesis of Transformed Cells of Lymphoid Origin," Blood, 89:610-620 (1997).
Hillerdal et al., "Systemic treatment with CAR-engineered T cells against PSCA delays subcutaneous tumor growth and prolongs survival of mice," BMC Cancer, 14:30 (2014).
International Preliminary Report on Patentability for Application No. PCT/GB2016/052564, dated Feb. 20, 2018.
International Search Report and Written Opinion for Application No. PCT/GB2016/052564, dated Oct. 12, 2016.
Leen et al., "Reversal of Tumor Immune Inhibition Using a Chimeric Cytokine Receptor," Mol Therapy, 22(6):1211-1220 (2014).
Leinonen et al., "Characterization of monoclonal antibodies against prostate specific antigen produced by genetic immunization," J Immunol Methods, 289(1-2):157-167 (2004).
Morgenroth et al., "Targeting of tumor cells expressing the prostate stem cell antigen (PSCA) using genetically engineered T-cells," The Prostate, 67(10):1121-1131 (2007).
Nagarkatti et al., "Constitutive activation of the interleukin 2 gene in the induction of spontaneous in vitro transformation and tumorigenicity of T cells," PNAS, 91(16):7638-7642 (1994).
Nustad et al., "Specificity and Affinity of 26 Monoclonal Antibodies against the CA 125 Antigen: First Report from the ISOBM TD-1 Workshop," Tumor Biology, 17:196-219 (1996).
Sogo et al., "Selective Expansion of Genetically Modified T Cells Using an Antibody/Interleukin-2 Receptor Chimera," J Immunol Methods, 337(1):16-23 (2008).
Stura et al., "Crystal Structure of Human Prostate-Specific Antigen in a Sandwich Antibody Complex," J Mol Biol, 414(4):530-544 (2011).
Wilkie et al., "Selective Expansion of Chimeric Antigen Receptor-targeted T-cells with Potent Effector Function using Interleukin-4," J Biol Chem, 285(33):25538-25545 (2010).
Chang et al., "Five Different Anti-Prostate-specific Membrane Antigen (PSMA) Antibodies Confirm PSMA Expression in Tumor-associated Neovasculature," Cancer Research 59:3192-3198 (1999).
Communication pursuant to Article 94(3) in European Application No. 16 756 758.5 dated Apr. 29, 2020 (12 pages).
Kawahara, et al., "Engineering cytokine receptors to control cellular functions," Biochemical Engineering Journal, 48:283-294 (2010).

* cited by examiner

US 10,800,854 B2

CHIMERIC CYTOKINE RECEPTORS AND ENCODING NUCLEIC ACIDS

This application is a National Stage Entry of International Application No. PCT/GB2016/052564, filed Aug. 19, 2016, which claims priority under § 119 to GB 1514875.2, filed Aug. 20, 2015, in the United Kingdom.

FIELD OF THE INVENTION

The present invention relates to a chimeric cytokine receptor (CCR), and a cell which expresses such a chimeric cytokine receptor and optionally a chimeric antigen receptor at the cell surface.

BACKGROUND TO THE INVENTION

Chimeric Antigen Receptors (CARs)

A number of immunotherapeutic agents have been described for use in cancer treatment, including therapeutic monoclonal antibodies (mAbs), bi-specific T-cell engagers and chimeric antigen receptors (CARs).

Chimeric antigen receptors are proteins which graft the specificity of a monoclonal antibody (mAb) to the effector function of a T-cell. Their usual form is that of a type I transmembrane domain protein with an antigen recognizing amino terminus, a spacer, a transmembrane domain all connected to a compound endodomain which transmits T-cell survival and activation signals.

The most common form of these molecules are fusions of single-chain variable fragments (scFv) derived from monoclonal antibodies which recognize a target antigen, fused via a spacer and a trans-membrane domain to a signaling endodomain. Such molecules result in activation of the T-cell in response to recognition by the scFv of its target. When T cells express such a CAR, they recognize and kill target cells that express the target antigen. Several CARs have been developed against tumour associated antigens, and adoptive transfer approaches using such CAR-expressing T cells are currently in clinical trial for the treatment of various cancers.

CAR-Based Approaches to Treat Prostate Cancer

Prostate cancer is the second most common cancer in men worldwide, and the sixth leading cause of cancer-related death. Globally, there are approximately 1,100,000 new cases and 300,000 mortalities every year, comprising 4 percent of all cancer deaths. It is estimated that 1 in every 6 men will be diagnosed with the disease during his lifetime.

Initial treatment for prostate cancer may consist of surgery, radiation, or hormone therapy, or any combination of each. Hormone therapy consists of lowering the levels of testosterone, the male hormone that fuels out-of-control cell growth. Chemotherapy is typically reserved for advanced-stage cancers.

When prostate cancers grow despite the lowering of testosterone levels by hormone therapy, treatment options are limited. Typically, the cancer vaccine sipuleucel-T (Provenge®) a dendritic cell-based therapeutic cancer vaccine designed to induce an immune response targeted against the prostatic acid phosphatase ((PAP) antigen), a radiopharmaceutical agent (such as radium-223 chloride), secondary hormone therapies (such as abiraterone or enzalutamide), and/or chemotherapies (docetaxel and cabazitaxel) are added to the hormonal therapy in sequence. While each of these treatments can delay growth of the cancer for several months and palliate symptoms produced by the disease, the disease ultimately becomes resistant to them.

Preclinically, two antigens associated with prostate cancer have been targeted with CAR T-cell based therapies: prostate-specific membrane antigen (PSMA) and prostate stem cell antigen (PSCA).

Mice treated with PSCA CAR-engineered T cells showed delayed tumour growth (Hillerdal et al (2014) BMC Cancer 14:30; and Abate-Daga et al (2014) 25:1003-1012). Although the cells showed high in vitro cytotoxicity, in vivo, tumour growth was delayed but tumour-bearing mice were not cured.

This may be because, in vivo, CAR T-cells struggle to overcome the hostile microenvironment of a carcinoma. In particular CAR T-cells may fail to engraft and expand within a prostate cancer tumour bed.

CAR T-cell persistence and activity can be enhanced by administration of cytokines, or by the CAR T-cells producing cytokines constitutively. However, these approaches have limitations: systemic administration of cytokines can be toxic; constitutive production of cytokines may lead to uncontrolled proliferation and transformation (Nagarkatti et al (1994) PNAS 91:7638-7642; Hassuneh et al (1997) Blood 89:610-620).

There is therefore a need for alternative CAR T-cell approaches, which facilitate engraftment and expansion of T cells to counteract the effects of the hostile tumour microenvironment.

On-Target Off-Tumour Toxicity

It is relatively rare for the presence of a single antigen effectively to describe a cancer, which can lead to a lack of specificity.

Most cancers cannot be differentiated from normal tissues on the basis of a single antigen. Hence, considerable "on-target off-tumour" toxicity occurs whereby normal tissues are damaged by the therapy. For instance, whilst targeting CD20 to treat B-cell lymphomas with Rituximab, the entire normal B-cell compartment is depleted, whilst targeting CD52 to treat chronic lymphocytic leukaemia, the entire lymphoid compartment is depleted, whilst targeting CD33 to treat acute myeloid leukaemia, the entire myeloid compartment is damaged etc.

The predicted problem of "on-target off-tumour" toxicity has been borne out by clinical trials. For example, an approach targeting ERBB2 caused death to a patient with colon cancer metastatic to the lungs and liver. ERBB2 is over-expressed in colon cancer in some patients, but it is also expressed on several normal tissues, including heart and normal vasculature.

There is therefore a need for improved approaches to cancer therapy in which such "on-target off-tumour" toxicity is reduced or eliminated.

(b) One implementation of a chimeric cytokine receptor is to replace the ectodomain of the cytokine alpha/beta and gamma chain with different scFvs (or any other suitable binder) which recognize different epitopes of PSA.

(c) An alternative approach is to replace the ectodomains of alpha/beta and gamma with the VH/VL of a PSA specific antibody, where both VH and VL are involved in binding so that binding brings them together.

Figure 3:
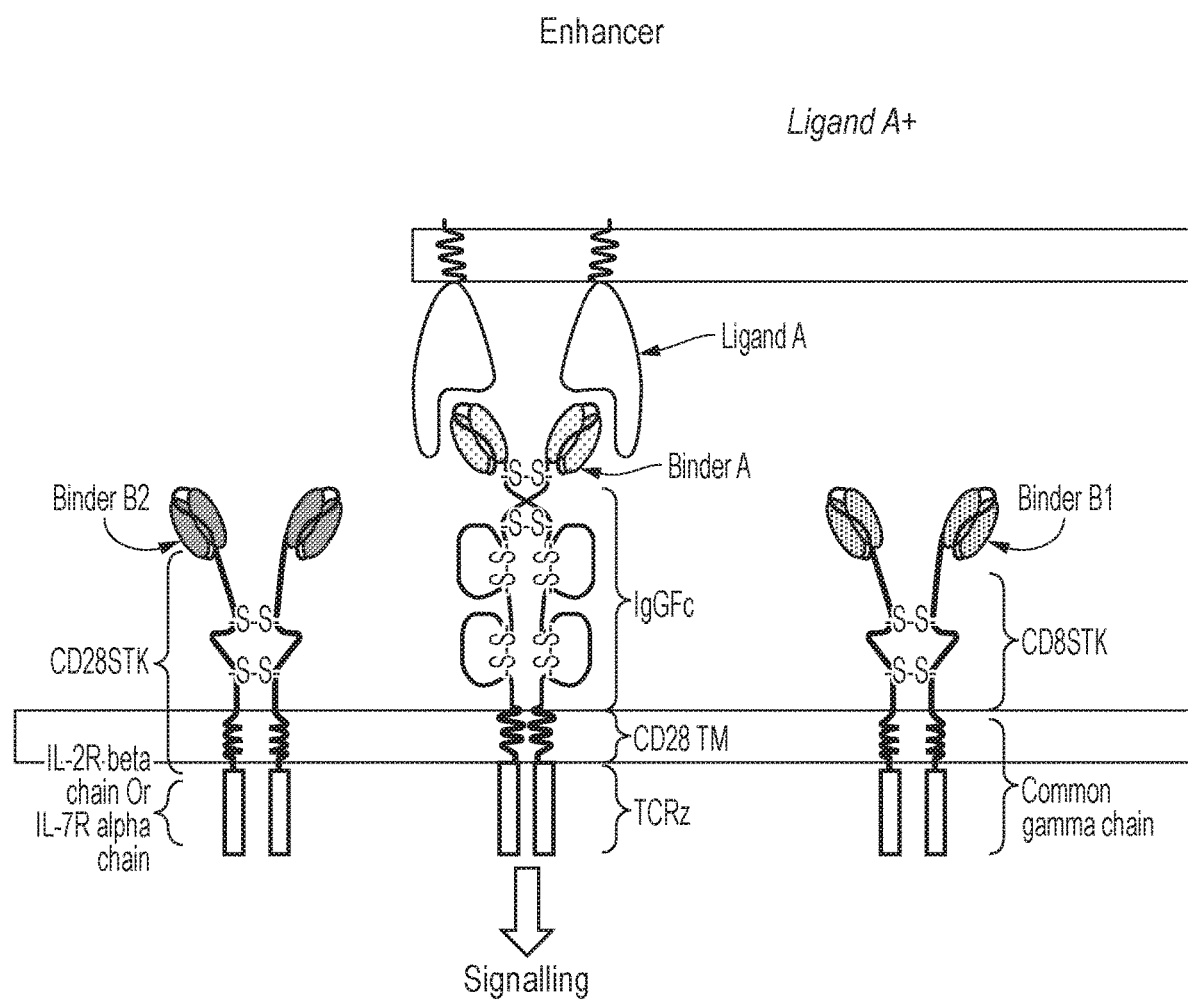
Figure 3:
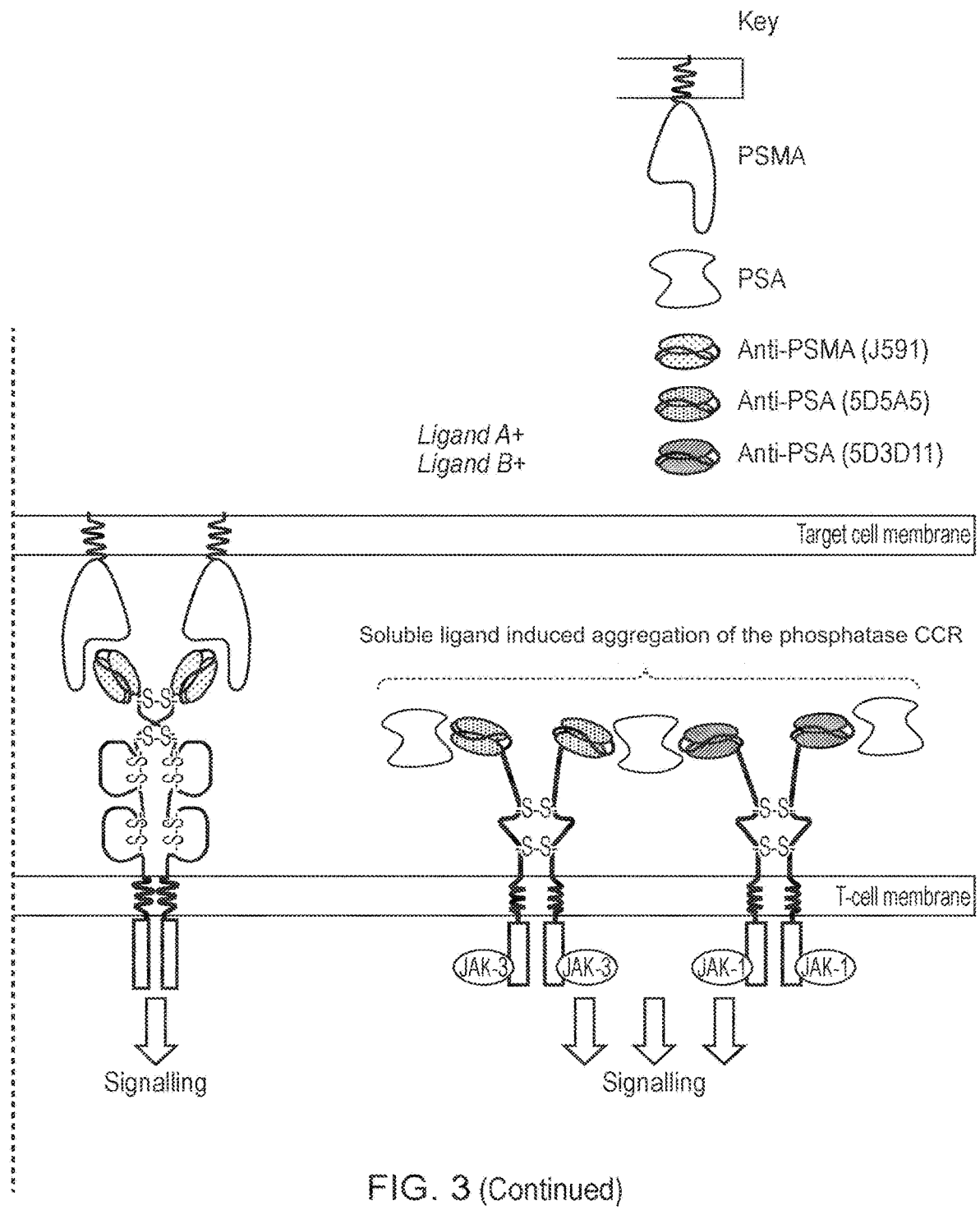

FIG. 3: Aggregation-based cytokine signalling enhancer

Schematic diagram showing a chimeric cytokine receptor and CAR combination system. The cell comprises two chimeric cytokine receptors which bind different epitopes on the same soluble ligand. In the absence of soluble ligand (e.g. PSA) but the presence of the cell-membrane antigen (e.g. PSMA) signalling occurs thought the CAR. In the presence of the soluble ligand, aggregation of the two chimeric cytokine receptors occurs, leading to cytokine-based signal enhancement.

Figure 4:
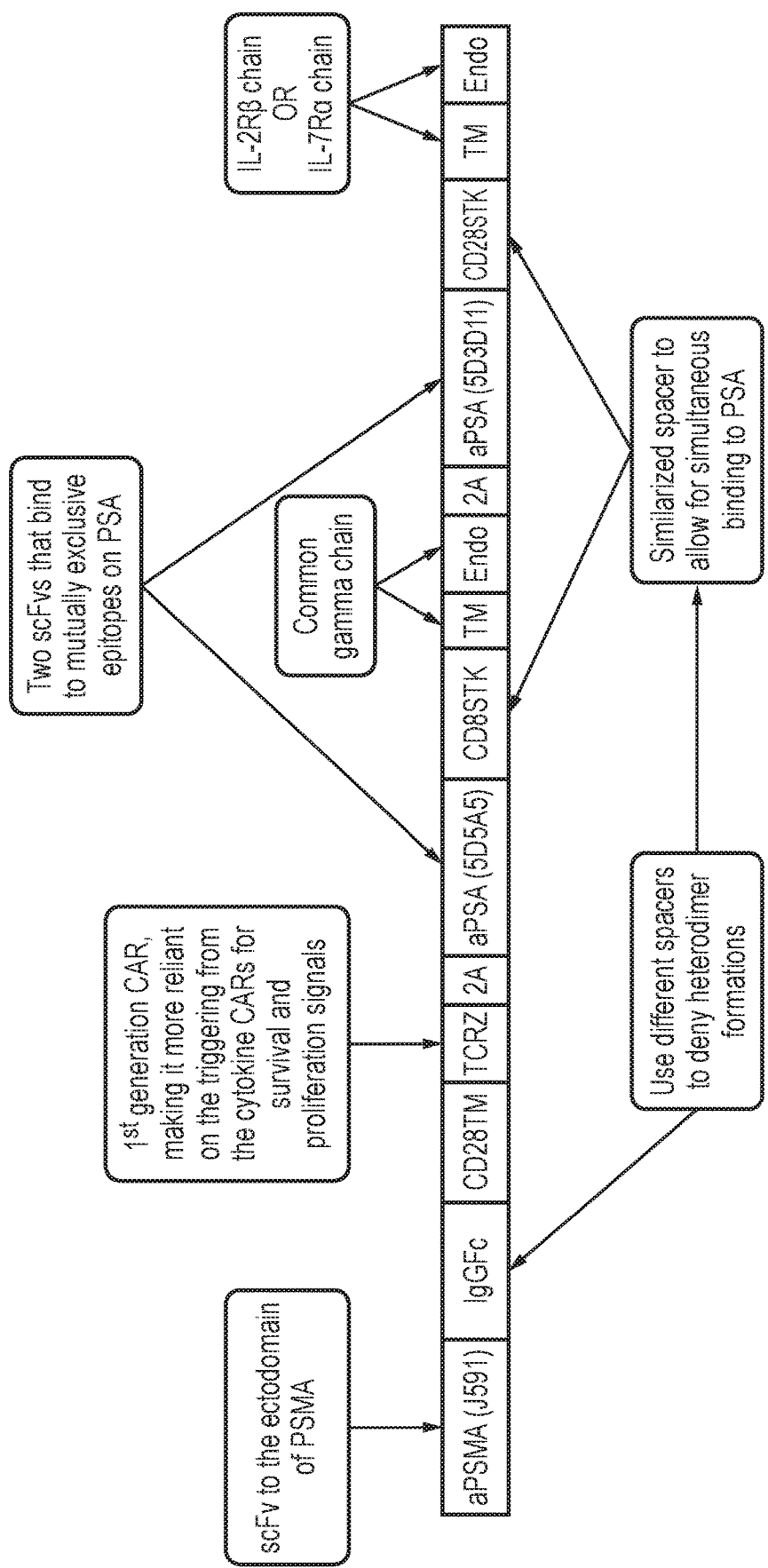

FIG. 4: Theoretical construct map for the chimeric cytokine receptor/CAR combination system illustrated in FIG. 3.

Figure 5:
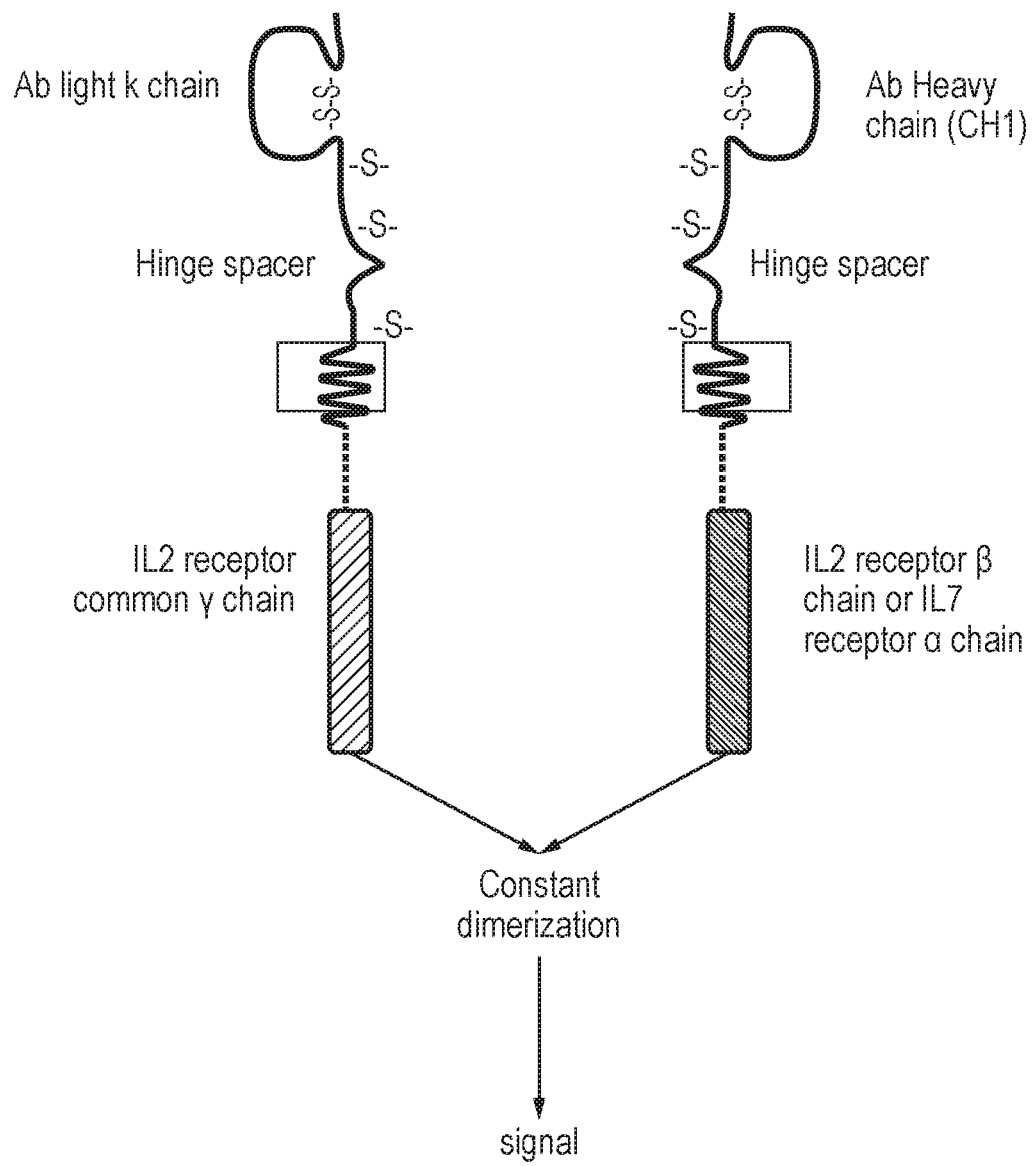

FIG. 5: Schematic diagram illustrating an example of a structure for the chimeric transmembrane protein of the present invention. The chimeric transmembrane protein comprises a dimerization domain and a cytokine receptor endodomain. The embodiment shown has a "Fab" type architecture, as the dimerization domain comprises antibody-type heavy and light chain constant regions. Constant dimerization between these domains brings together the IL2 receptor common γ chain with either the IL-2 receptor β chain or the IL-7 receptor α chain, leading to constitutive cytokine signalling.

Figure 6:
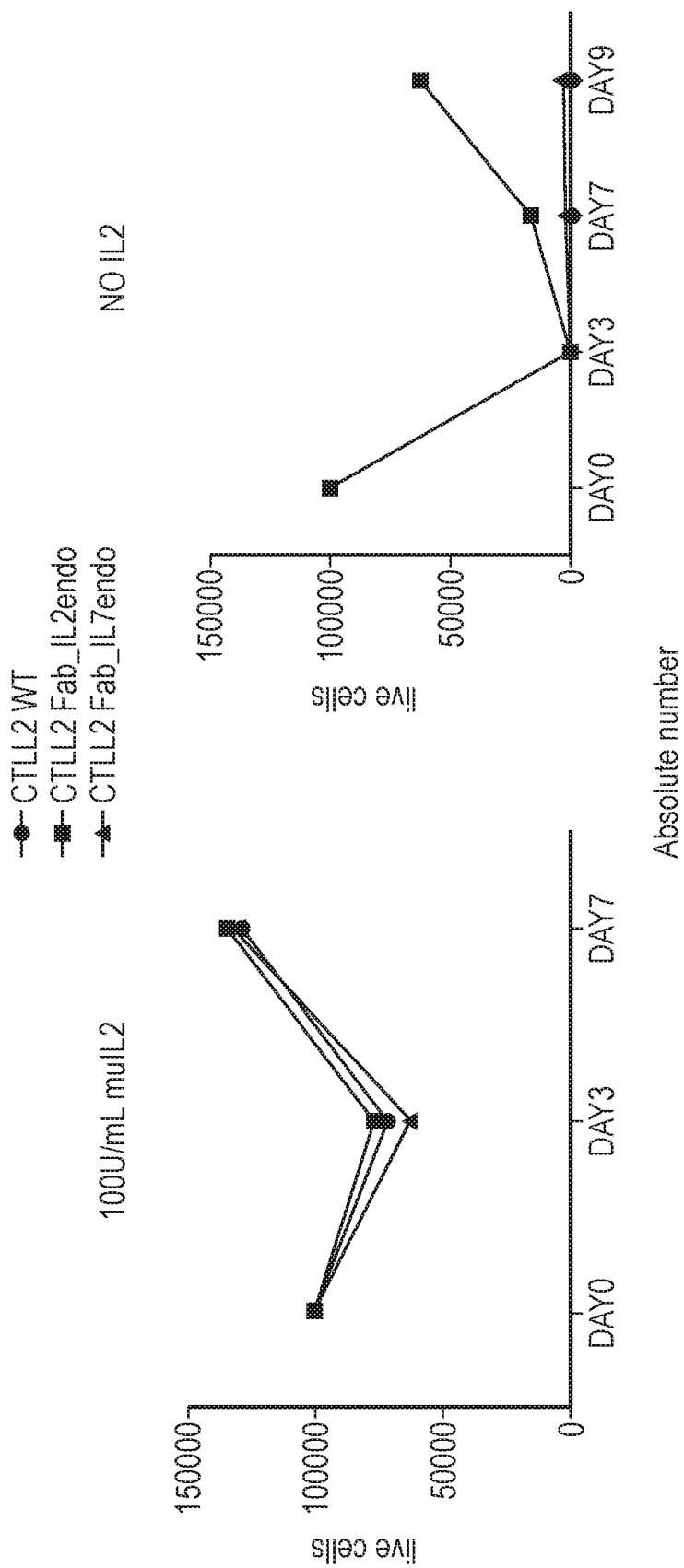

FIG. 6: IL-2 signalling by the chimeric transmembrane protein.

Two chimeric transmembrane proteins having the general structure shown in FIG. 5 were tested for their ability to induce IL-2 signalling. One chimeric transmembrane protein comprised an IL2 receptor endodomain and the other comprised an IL-7 receptor endodomain. IL-2 signalling was tested using the murine cell line CTLL2 which is dependent on IL-2 signalling for growth. As a positive control, CTLL2 cells were cultured with 100 u/mL murine IL2. Cells expressing the chimeric transmembrane protein comprising the IL2 receptor endodomain (Fab_IL2endo) supported CTLL2 cell survival and growth, whereas cells expressing the chimeric transmembrane protein comprising the IL-7 receptor (Fab_IL7endo) did not.

Figure 7:
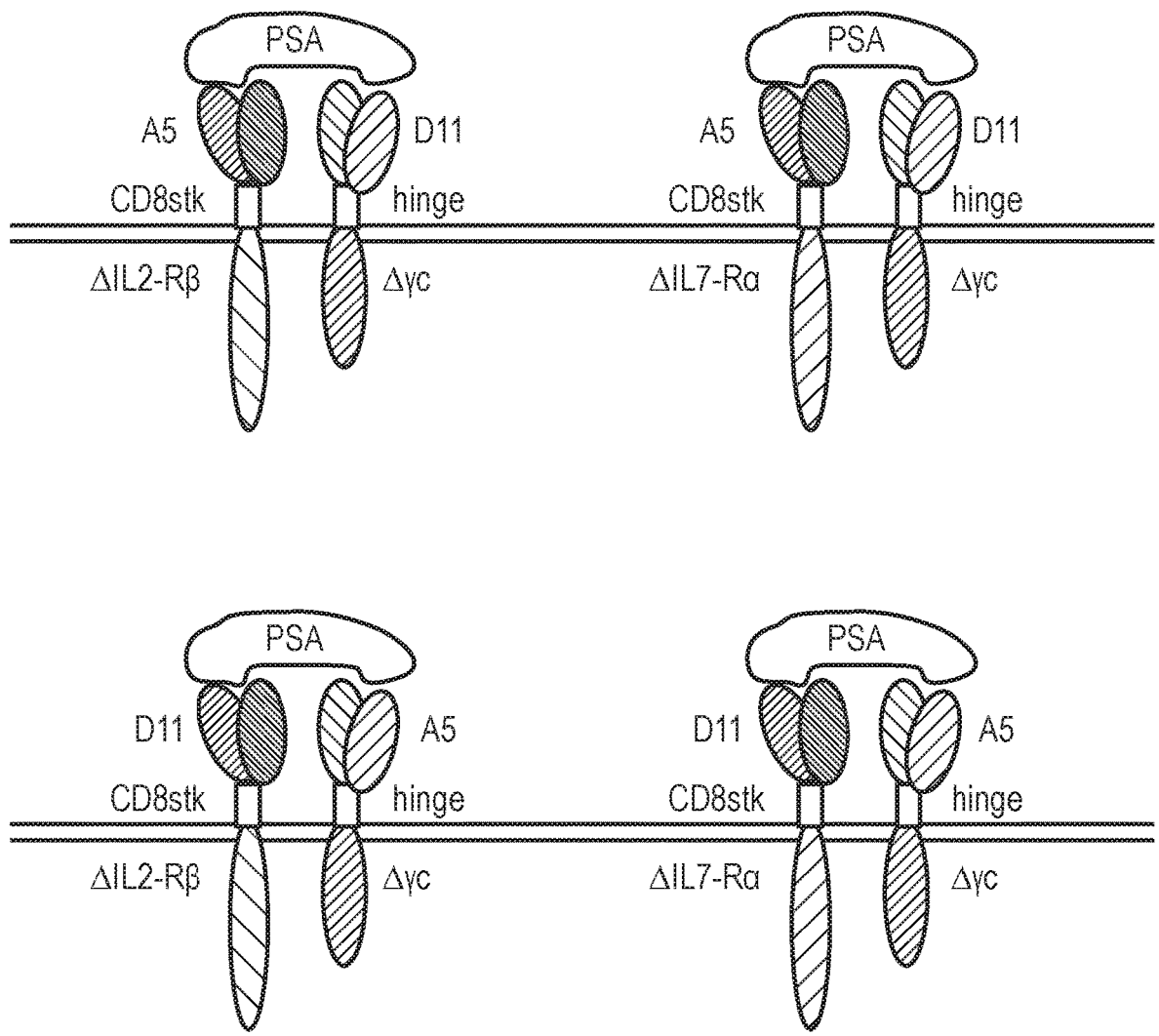

FIG. 7: Schematic diagram illustrating panel of PSA chimeric cytokine receptors

A panel of chimeric cytokine receptors (CCRs) targeting PSA was developed using scFvs derived from two antibodies which bind to different PSA epitopes: 5D5A5 and 5D3D11.

Top-left panel: A CCR with an IL-2R endodomain having A5 on the chain with IL2R β chain and D11 on the chain with common γ chain;

Top-right panel: A CCR with an IL7R endodomain having A5 on the chain with IL7R α chain and D11 on the chain with common γ chain;

Bottom-left panel: A CCR with an IL-2R endodomain having D11 on the chain with IL2R β chain and A5 on the chain with common γ chain; and Bottom-right hand panel: A CCR with an IL-7R endodomain having D11 on the chain with IL7R α chain and A5 on the chain with common γ chain.

A negative control was also created for each CCR, in which the IL2Rγ chain was replaced by a rigid linker.

Figure 8:
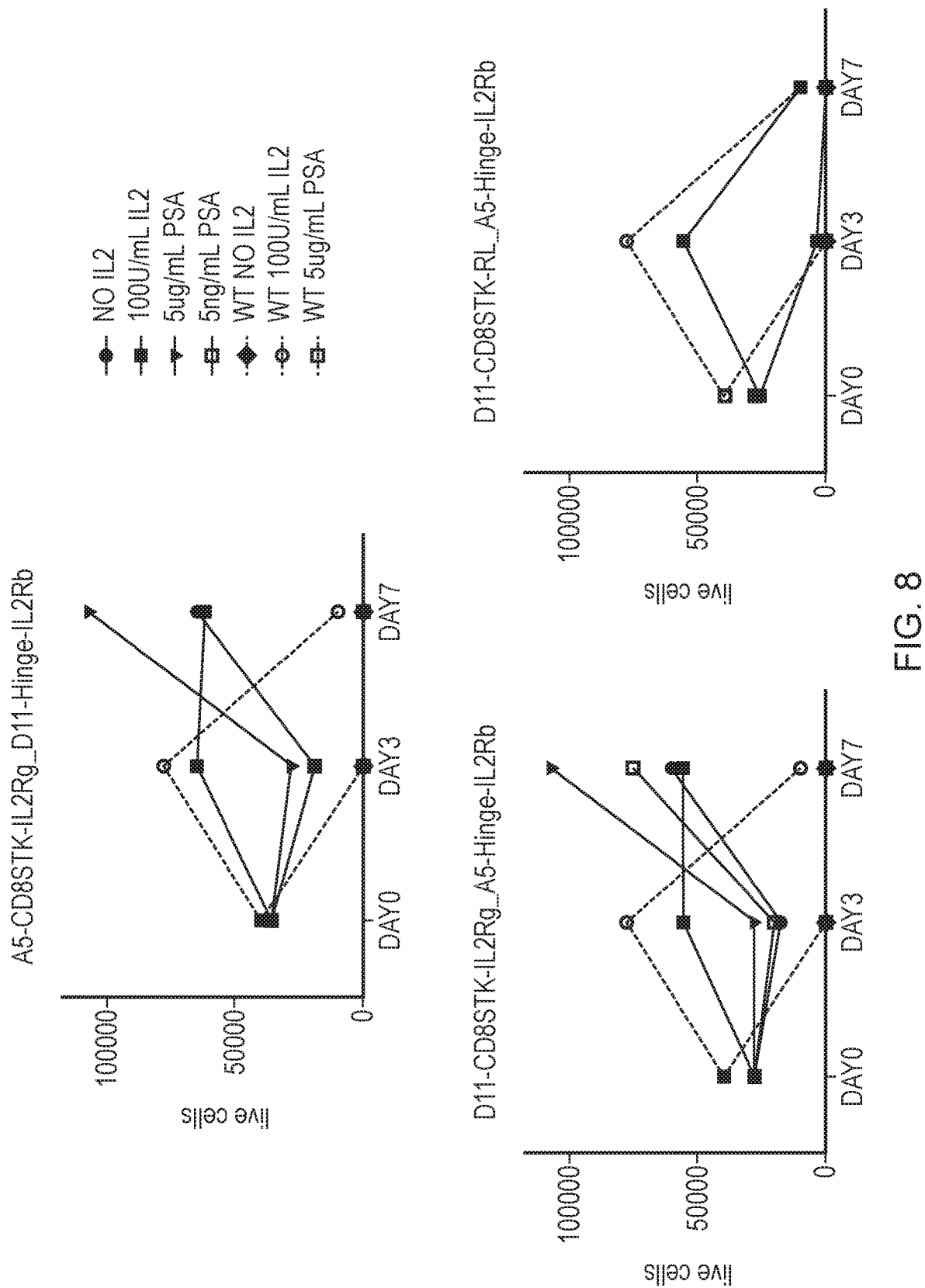
Figure 8:
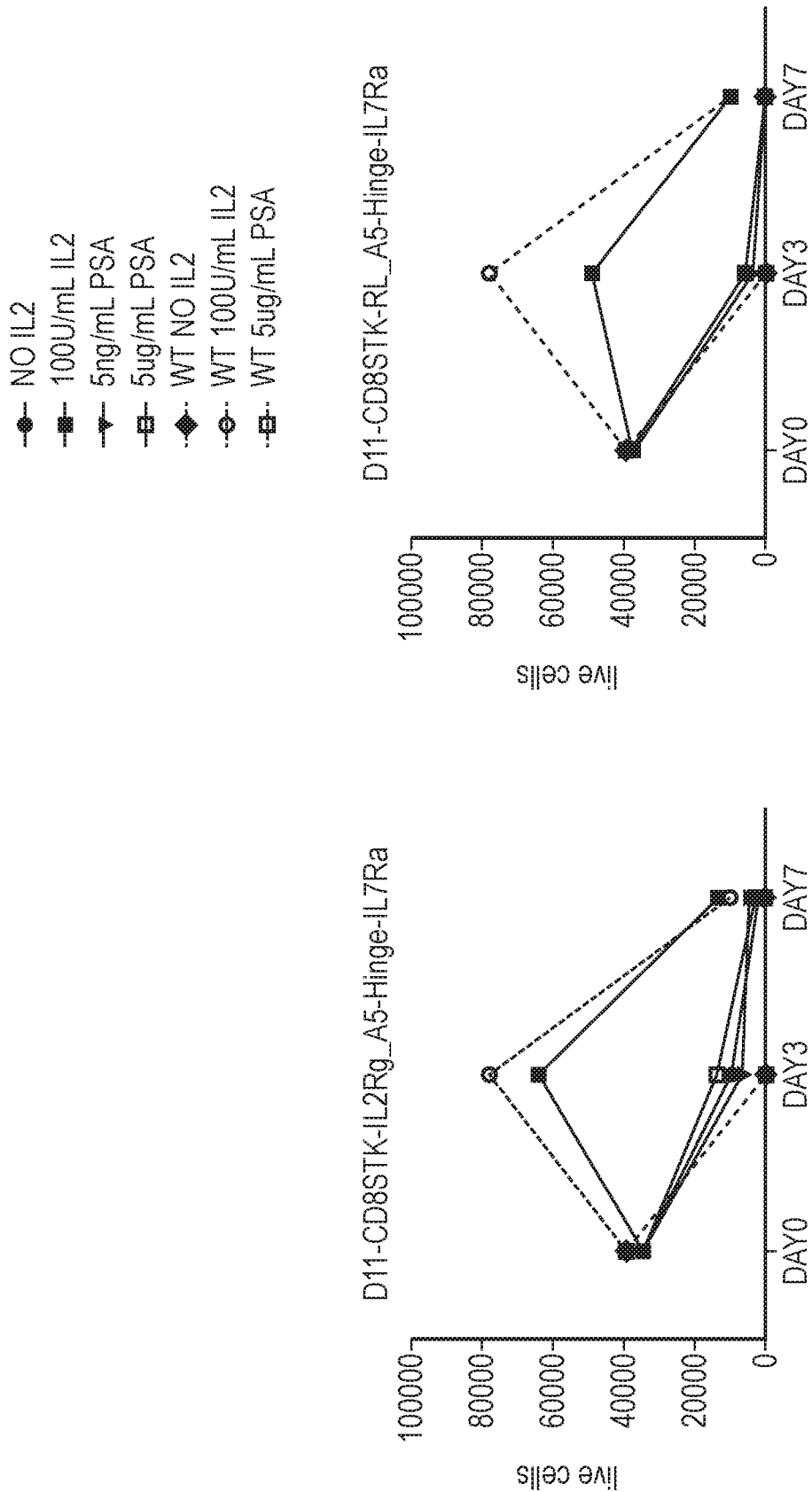

FIG. 8: IL2 signalling from cells expressing a PSA chimeric cytokine receptor in the presence of PSA-CTLL2 proliferation CTLL2 cells were transduced with constructs expressing some of the PSA chimeric cytokine receptors illustrated in FIG. 7. Cells were cultured in the presence of absence of IL2 (positive control) and the presence of absence of 5 ng/mL or 5 μg/mL PSA. CTLL2 proliferation was assessed after 3 and 7 days.

The anti-PSA chimeric cytokine receptor with an IL2R endodomain supported CTLL2 cell proliferation in the absence of IL2 and the presence of PSA, but not the receptor having an IL7R endodomain or any of the CCRs comprising a rigid linker in the place of the common γ chain.

Figure 9:
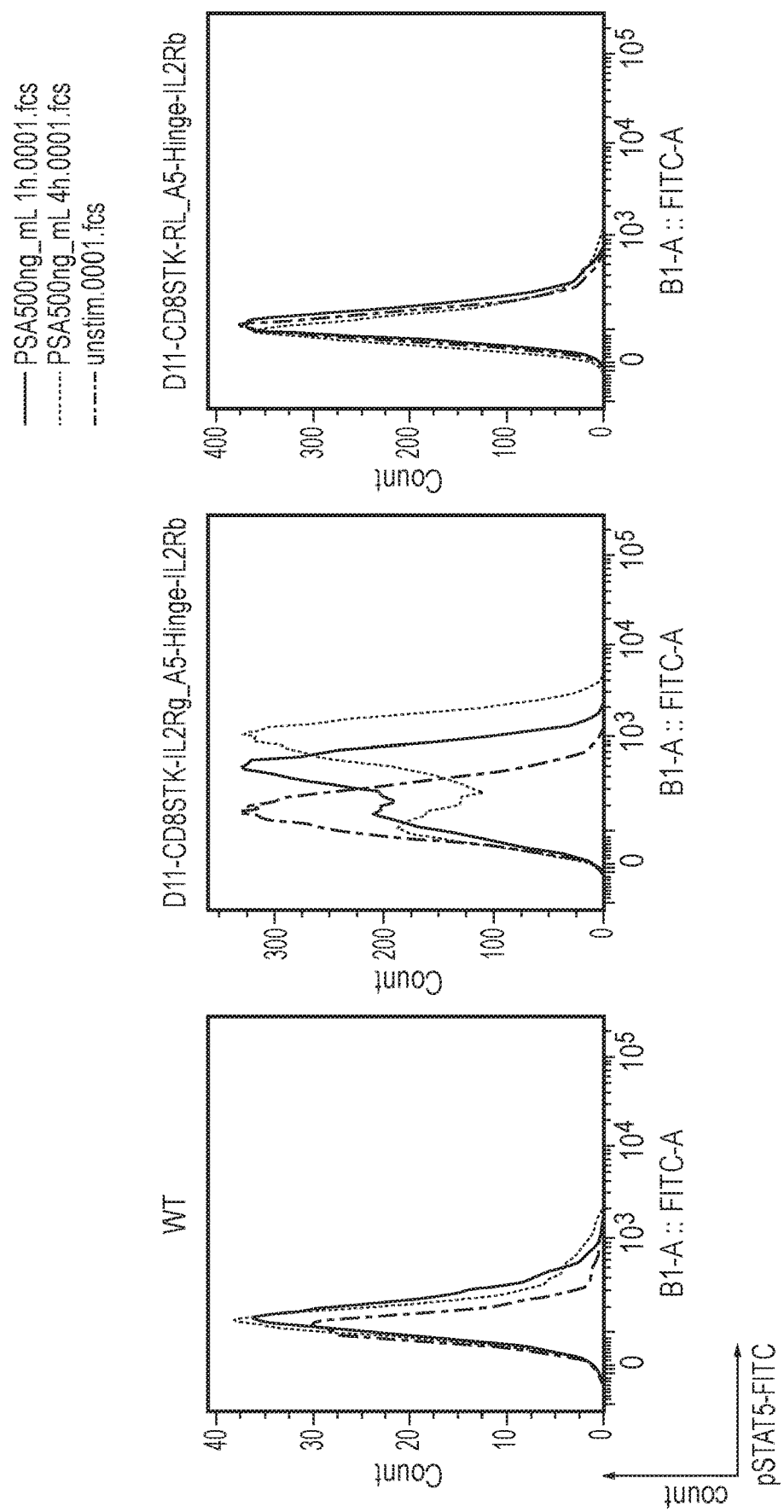

FIG. 9: IL2 signalling from cells expressing a PSA chimeric cytokine receptor in the presence of PSA-CTLL2 STAT5 phosphorylation CTLL2 cells were either left untransduced (WT); or transduced with a vector expressing a CCR against PSA (D11-CD8STK-IL2Rg_A5-Hinge-IL2Rb) or an equivalent construct having a rigid linker in the place of the common γ chain (D11-CD8STK-RL_A5-Hinge-IL2Rb). Cells were incubated with either 500 μM Pervanadate or 500 ng/mL PSA for 1 or 4 hours. Phosphorylation of Y694 of STAT5 was then investigated using phosphoflow.

SUMMARY OF ASPECTS OF THE INVENTION

The present inventors have developed "chimeric cytokine receptors" (CCR) which graft the binding specificity of a non-cytokine binding molecule on to the endodomain of a cytokine receptor. The co-expression of such a CCR with a chimeric antigen receptor (CAR) helps a CAR T-cell to engraft and expand in the hostile tumour microenvironment. The requirement for the ligand for the CCR as well as the ligand for the CAR to be present add another layer of selectivity and helps prevent on-target off-tumour toxicity.

For example, they have developed a cell which co-expresses a CAR with a chimeric cytokine receptor which detects PSA and transmits an IL2/15 or an IL7 signal to the CAR T-cell. In this way, the CAR T-cell is stimulated to proliferate selectively only in a prostate cancer microenvironment, and in the absence of PSA (i.e. after the patient is in remission), the cytokine stimulation is lost.

In a first aspect, the present invention provides a chimeric cytokine receptor (CCR) comprising:
  an exodomain which binds to a ligand selected from a tumour secreted factor, a chemokine and a cell-surface antigen; and
  a cytokine receptor endodomain.

Figure 1:
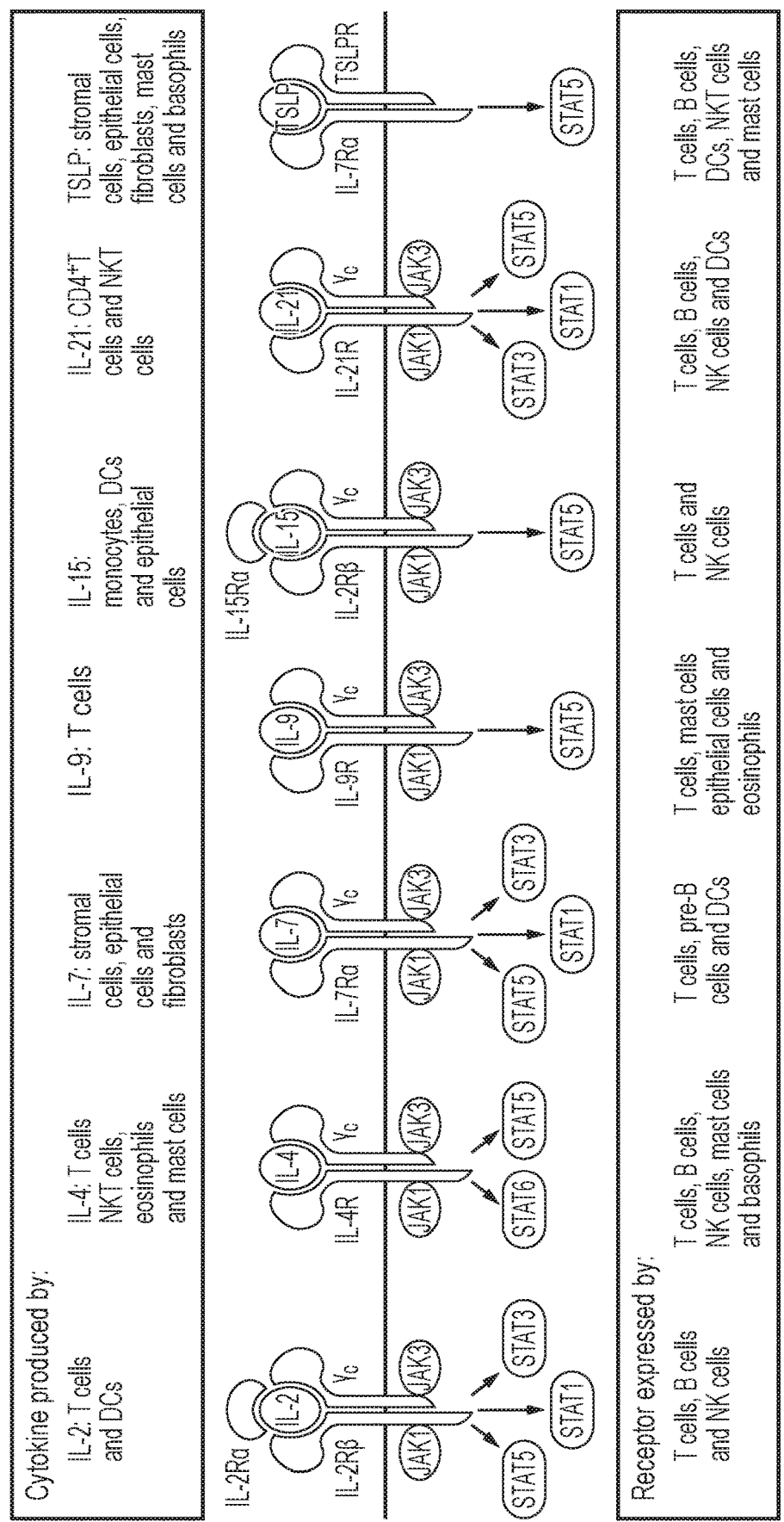
FIG. 1: Schematic diagram summarising the structure of various cytokine receptors, the cell types which produce the cytokines and the cell types which express the cytokine receptors.
Figure 2:
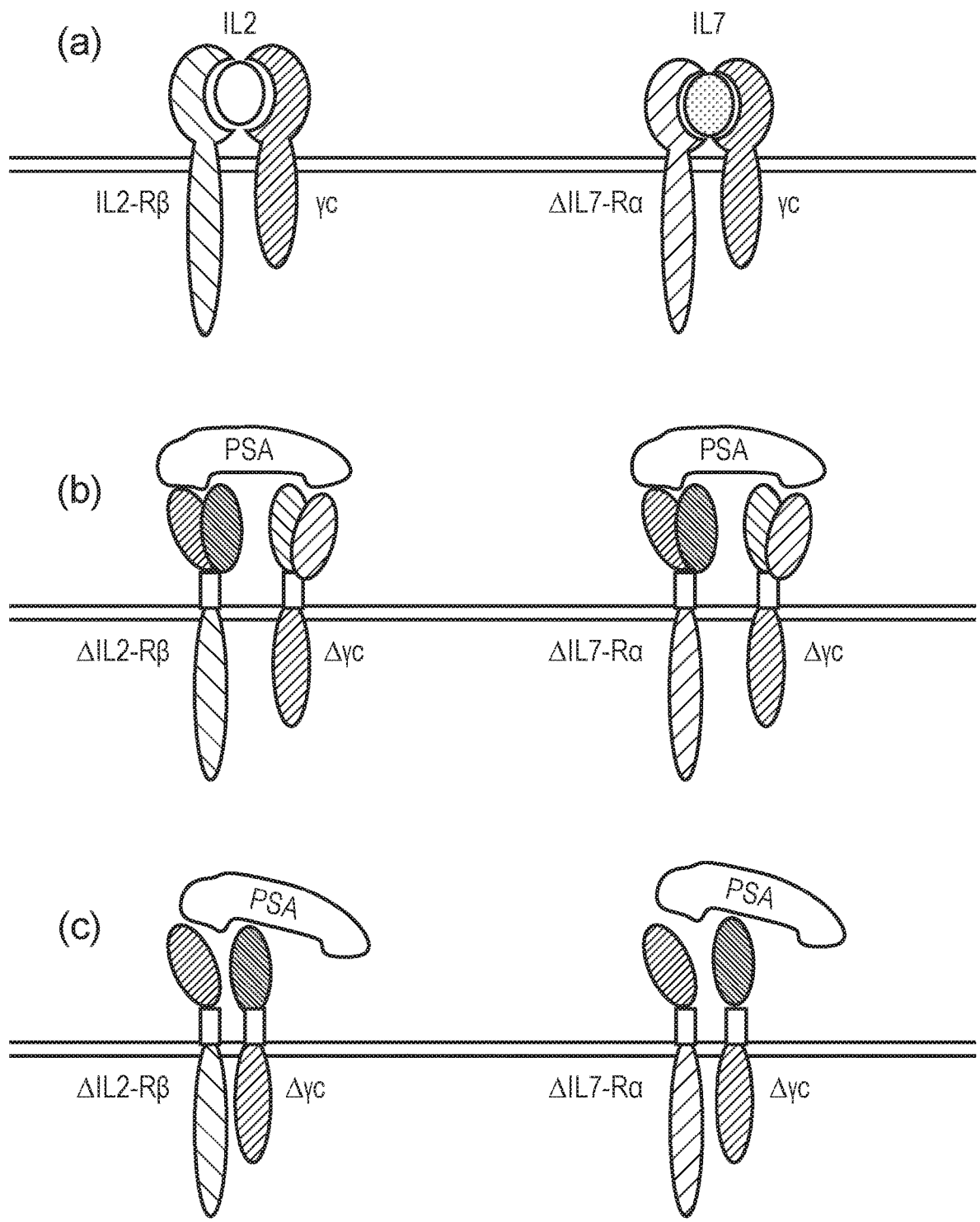
FIG. 2: Schematic diagram showing proposed chimeric cytokine receptor (a) Cytokine IL2 and IL7 cytokine receptors signal through a common gamma chain and a cytokine specific alpha/beta chain.

In a first embodiment of the first aspect of the invention, the chimeric cytokine receptor comprises two polypeptides:
  (i) a first polypeptide which comprises:
    (a) a first antigen-binding domain which binds a first epitope of the ligand
    (b) a first chain of the cytokine receptor endodomain; and
  (ii) a second polypeptide which comprises:
    (a) a second antigen-binding domain which binds a second epitope of the ligand
    (b) a second chain of the cytokine-receptor endodomain. FIG. 2b illustrates such an arrangement.

Each of the first and second antigen-binding domains may be, for example, single-chain variable fragments (scFvs) or single domain binders.

In a second embodiment of the first aspect of the invention, the chimeric cytokine receptor which comprises two polypeptides:

(i) a first polypeptide which comprises:
  (a) a heavy chain variable domain (VH)
  (b) a first chain of the cytokine receptor endodomain; and
(ii) a second polypeptide which comprises:
  (a) a light chain variable domain (VL)
  (b) a second chain of the cytokine-receptor endodomain.

FIG. 2c illustrates such an arrangement.

The first and second chains for the cytokine receptor endodomains may be different and may be selected from type I cytokine receptor endodomain α-, β-, and γ-chains.

Alternatively the first and second chains for the cytokine receptor endodomains may be the same and may be selected from type I cytokine receptor endodomain α-, β-, and γ-chains.

For example, the cytokine receptor endodomain may comprise:
(i) IL-2 receptor β-chain endodomain
(ii) IL-7 receptor α-chain endodomain;
(iii) IL-15 receptor α-chain endodomain; or
(iv) common γ-chain receptor endodomain.

The cytokine receptor endodomain may comprise (i), (ii) or (iii); and (iv).

The ligand may be a tumour secreted factor, for example a tumour secreted factor selected from: prostate-specific antigen (PSA), carcinoembryonic antigen (CEA), vascular endothelial growth factor (VEGF) and CA125.

The ligand may be a chemokine, for example a chemokine selected from chemokine selected from: CXCL12, CCL2, CCL4, CCL5 and CCL22.

The ligand may be a cell-surface molecule, such as a transmembrane protein. The ligand may be, for example, CD22.

In a second aspect, the present invention provides a cell which comprises a chimeric cytokine receptor according to the first aspect of the invention.

The cell may comprise a first chimeric cytokine receptor and a second chimeric cytokine receptor which bind different epitopes on the same ligand.

The cell may comprise a first chimeric cytokine receptor which comprises a type I cytokine receptor endodomain α- or β-chain, and a second chimeric cytokine receptor which comprises a type I cytokine receptor endodomain γ-chain, such that when the first chimeric cytokine receptor and the second cytokine receptor bind the ligand, combined signalling through the α-/β-chain and γ-chain occurs.

The cell may also comprise a chimeric antigen receptor, for example a chimeric antigen receptor which binds a tumour-associated cell surface antigen.

The chimeric antigen receptor may bind a cell surface antigen associated with prostate cancer, such as prostate stem-cell antigen (PSCA) or prostate-specific membrane antigen (PSMA).

Where the CCR recognises a cell-surface antigen, the CCR and CAR may recognise cell-surface antigens which are co-expressed on the same target (e.g. tumour) cell. For example, for B-cell malignancies, the CAR may recognize a cell-surface antigen such as CD19 and the CCR may recognize a molecule which is co-expressed on the target cell surface, such CD22, thereby enhancing engraftment.

In a third aspect, the present invention provides a nucleic acid sequence encoding a chimeric cytokine receptor (CCR) according to the first aspect of the invention.

In a fourth aspect the present invention provides a nucleic acid construct which comprises a first nucleic acid sequence encoding a first CCR and a second nucleic acid sequence encoding a second CCR, the nucleic acid construct having the structure:

AgB1-spacer1-TM1-endo1-coexpr-AbB2-spacer2-TM2-endo2 in which
AgB1 is a nucleic acid sequence encoding the antigen-binding domain of the first CCR;
spacer 1 is a nucleic acid sequence encoding the spacer of the first CCR;
TM1 is a a nucleic acid sequence encoding the transmembrane domain of the first CCR;
endo 1 is a nucleic acid sequence encoding the endodomain of the first CCR;
coexpr is a nucleic acid sequence enabling co-expression of both CCRs
AgB2 is a nucleic acid sequence encoding the antigen-binding domain of the second CCR;
spacer 2 is a nucleic acid sequence encoding the spacer of the second CCR;
TM2 is a a nucleic acid sequence encoding the transmembrane domain of the second CCR;
endo 2 is a nucleic acid sequence encoding the endodomain of the second CCR.

The nucleic acid construct may also encode a chimeric antigen receptor (CAR). In this embodiment, the nucleic acid construct may have the structure:
(i)  CCRAgB1-CCRspacer1-CCRTM1-CCRendo1-coexpr1-CCRAgB2-CCRspacer2-CCRTM2-CCRendo2-coexpr2-CARAgB-CARspacer-CARTM-CARendo;
(ii) CCRAgB1-CCRspacer1-CCRTM1-CCRendo1-coexpr1-CARAgB-CARspacer-CARTM-CARendo-coexpr2-CCRAgB2-CCRspacer2-CCRTM2-CCRendo2; or
(iii) CARAgB-CARspacer-CARTM-CARendo-coexpr1-CCRAgB1-CCRspacer1-CCRTM1-CCRendo1-coexpr2-CCRAgB2-CCRspacer2-CCRTM2-CCRendo2;

in which
CCRAgB1 is a nucleic acid sequence encoding the antigen-binding domain of the first CCR;
CCRspacer1 is a nucleic acid sequence encoding the spacer of the first CCR;
CCRTM1 is a nucleic acid sequence encoding the transmembrane domain of the first CCR;
CCRendo1 is a nucleic acid sequence encoding the endodomain of the first CCR;
CCRAgB2 is a nucleic acid sequence encoding the antigen-binding domain of the second CCR;
CCRspacer2 is a nucleic acid sequence encoding the spacer of the second CCR;
CCRTM2 is a nucleic acid sequence encoding the transmembrane domain of the second CCR;
CCRendo2 is a nucleic acid sequence encoding the endodomain of the second CCR;
Coexpr1 and coexpr2 are nucleic acid sequences enabling co-expression of the two flanking sequences;
CARAgB is a nucleic acid sequence encoding the antigen-binding domain of the CAR;
CARspacer is a nucleic acid sequence encoding the spacer of the CAR;
CARTM is a nucleic acid sequence encoding the transmembrane domain of the CAR; and
CARendo is a nucleic acid sequence encoding the endodomain of the CAR.

Any or all of the sequences coexpr, coexpr1, coexpr2 may encode a sequence comprising a self-cleaving peptide.

Alternative codons may be used in regions of sequence encoding the same or similar amino acid sequences, in order to avoid homologous recombination.

In a fifth aspect, the present invention provides a vector comprising a nucleic acid construct according to the fourth aspect of the invention.

The vector may be, for example, a retroviral vector or a lentiviral vector or a transposon.

In a sixth aspect, the present invention provides a kit which comprises:
  i) a vector comprising a nucleic acid sequence encoding a first CCR according to the first aspect of the invention; and
  ii) a vector comprising a nucleic acid sequence encoding a second CCR according to the second aspect of the invention.

The kit may also comprise a vector comprising a nucleic acid sequence encoding a chimeric antigen receptor.

The kit may comprise:
  i) a vector comprising a nucleic acid sequence encoding a CCR according to the first aspect of the invention; and
  ii) a vector comprising a nucleic acid sequence encoding a chimeric antigen receptor.

In a seventh aspect, the present invention provides a method for making a cell according to the second aspect of the invention, which comprises the step of introducing: a nucleic acid sequence according to the third aspect of the invention; a nucleic acid construct according to the fourth aspect of the invention; a vector according to the fifth aspect of the invention; or a kit of vectors according to the sixth aspect of the invention, into a cell.

The cell may be from a sample isolated from a subject.

In an eighth aspect, there is provided a pharmaceutical composition comprising a plurality of cells according to the second aspect of the invention.

In a ninth aspect, there is provided a method for treating and/or preventing a disease, which comprises the step of administering a pharmaceutical composition according to the eighth aspect of the invention to a subject.

The method may comprise the following steps:
  (i) isolation of a cell-containing sample from a subject;
  (ii) transduction or transfection of the cells with: a nucleic acid sequence according to the third aspect of the invention; a nucleic acid construct according to the fourth aspect of the invention; a vector according to the fifth aspect of the invention; or a kit of vectors according to the sixth aspect of the invention; and
  (iii) administering the cells from (ii) to a the subject.

The sample may be a T-cell containing sample.

The disease may be a cancer.

There is also provided a pharmaceutical composition according to the eighth aspect of the invention for use in treating and/or preventing a disease.

There is also provided the use of a cell according to the second aspect of the invention in the manufacture of a medicament for treating and/or preventing a disease.

Further aspects of the invention are summarised in the following numbered paragraphs:

1. A chimeric transmembrane protein comprising:
   a dimerization domain; and
   a cytokine receptor endodomain.
2. A chimeric transmembrane protein according to paragraph 1, wherein the dimerization domain comprises the dimerisation portion of a heavy chain constant domain ($C_H$) and a light chain constant domain ($C_L$).
3. A chimeric transmembrane protein according to any preceding paragraph, which comprises two polypeptides:
   (i) a first polypeptide which comprises:
     (a) a first dimerisation domain; and
     (b) a first chain of the cytokine receptor endodomain; and
   (ii) a second polypeptide which comprises:
     (a) a second dimerization domain, which dimerises with the first dimerization domain; and
     (b) a second chain of the cytokine-receptor endodomain.
4. A chimeric transmembrane protein according to paragraph 3, wherein the first and second dimerization domains either dimerise spontaneously, or in the presence of a chemical inducer of dimerization (CID).
5. A chimeric transmembrane protein according to paragraph 2, 3 or 4 which comprises two polypeptides:
   (i) a first polypeptide which comprises:
     (a) a heavy chain constant domain (CH)
     (b) a first chain of the cytokine receptor endodomain; and
   (ii) a second polypeptide which comprises:
     (a) a light chain constant domain (CL)
     (b) a second chain of the cytokine-receptor endodomain.
6. A chimeric transmembrane protein according to paragraph 5 wherein the first and second chains for the cytokine receptor endodomains are different and are selected from type I cytokine receptor endodomain α-, β-, and γ-chains.
7. A chimeric transmembrane protein according to paragraph 5 wherein the first and second chains for the cytokine receptor endodomains are the same and are selected from type I cytokine receptor endodomain α-, β-, and γ-chains.
8. A chimeric transmembrane protein according to any preceding paragraph, wherein the cytokine receptor endodomain comprises:
   (i) IL-2 receptor β-chain endodomain
   (ii) IL-7 receptor α-chain endodomain; or
   (iii) IL-15 receptor α-chain endodomain; and/or
   (iv) common γ-chain receptor endodomain.
9. A chimeric transmembrane protein according to paragraph 5, wherein the first polypeptide comprises a heavy chain variable domain (VH) and a heavy chain constant domain (CH); and the second polypeptide comprises a light chain variable domain (VL) and a light chain constant domain (CL).
10. A chimeric transmembrane protein according to paragraph 9 which comprises a Fab exodomain.
11. A cell which comprises a chimeric transmembrane protein according to any preceding paragraph.
12. A cell according to paragraph 11, which also comprises a chimeric antigen receptor.
13. A cell according to paragraph 12, wherein the chimeric antigen receptor binds a tumour-associated cell surface antigen.
14. A nucleic acid sequence encoding a chimeric transmembrane protein according to any of paragraphs 1 to 10.
15. A nucleic acid construct which comprises a first nucleic acid sequence encoding a first polypeptide as defined in paragraph 3 and a second nucleic acid sequence encoding a second polypeptide as defined in paragraph 3, the nucleic acid construct having the structure:

Dim1-TM1-endo1-coexpr-Dim2-TM2-endo2
in which
Dim1 is a nucleic acid sequence encoding the first dimerisation domain;
TM1 is a a nucleic acid sequence encoding the transmembrane domain of the first polypeptide;
endo 1 is a nucleic acid sequence encoding the endodomain of the first polypeptide;
coexpr is a nucleic acid sequence enabling co-expression of both CCRs
Dim2 is a nucleic acid sequence encoding the second dimerization domain;
TM2 is a a nucleic acid sequence encoding the transmembrane domain of the second polypeptide;
endo 2 is a nucleic acid sequence encoding the endodomain of the second polypeptide.

16. A nucleic acid construct according to paragraph 15 which also encodes a chimeric antigen receptor (CAR).

17. A nucleic acid construct according to paragraph 15 or 16, wherein coexpr encodes a sequence comprising a self-cleaving peptide.

18. A nucleic acid construct according to any of paragraphs 15 to 17, wherein alternative codons are used in regions of sequence encoding the same or similar amino acid sequences, in order to avoid homologous recombination.

19. A vector comprising a nucleic acid construct according to any of paragraphs 15 to 18.

20. A retroviral vector or a lentiviral vector or a transposon according to paragraph 19.

21. A kit which comprises:
   i) a vector comprising a nucleic acid sequence encoding a first polypeptide as defined in paragraph 3; and
   ii) a vector comprising a nucleic acid sequence encoding a second polypeptide as defined in paragraph 3.

22. A kit according to paragraph 21 which also comprises a vector comprising a nucleic acid sequence encoding a chimeric antigen receptor.

23. A kit which comprises:
   i) a vector comprising a nucleic acid sequence encoding a chimeric transmembrane protein as defined in any of paragraphs 1 to 10; and
   ii) a vector comprising a nucleic acid sequence encoding a chimeric antigen receptor.

24. A method for making a cell according to any of paragraphs 11 to 13, which comprises the step of introducing: a nucleic acid sequence according to paragraph 14; a nucleic acid construct according to any of paragraphs 15 to 18; a vector according to paragraph 19 or 20; or a kit of vectors according to any paragraphs 21 to 23, into a cell.

25. A method according to paragraph 24, wherein the cell is from a sample isolated from a subject.

26. A pharmaceutical composition comprising a plurality of cells according to any of paragraphs 11 to 13.

27. A method for treating and/or preventing a disease, which comprises the step of administering a pharmaceutical composition according to paragraph 26 to a subject.

28. A method according to paragraph 27, which comprises the following steps:
   (i) isolation of a cell-containing sample from a subject;
   (ii) transduction or transfection of the cells with: a nucleic acid sequence according to paragraph 14; a nucleic acid construct according to any of paragraphs 15 to 18; a vector according to paragraph 19 or 20; or a kit of vectors according to any paragraphs 21 to 23; and
   (iii) administering the cells from (ii) to a the subject.

29. A method according to paragraph 28, wherein the sample is a T-cell containing sample.

30. A method according to paragraph 28 or 29, wherein the disease is a cancer.

31. A pharmaceutical composition according to paragraph 26 for use in treating and/or preventing a disease.

32. The use of a cell according to any of paragraphs 11 to 13 in the manufacture of a medicament for treating and/or preventing a disease.

DETAILED DESCRIPTION

Chimeric Cytokine Receptor (CCR)

A chimeric cytokine receptor (CCR) is a molecule which comprises a cytokine receptor endodomain and a heterologous ligand-binding exodomain. The heterologous exodomain binds a ligand other than the cytokine for which the cytokine receptor from which the endodomain was derived is selective. In this way, it is possible to alter the ligand specificity of a cytokine receptor by grafting on a heterologous binding specificity.

A chimeric cytokine receptor comprises:
   (i) a ligand binding exodomain;
   (ii) an optional spacer;
   (iii) a transmembrane domain; and
   (iv) a cytokine-receptor endodomain.

Cytokine Receptors and Signalling

Many cell functions are regulated by members of the cytokine receptor superfamily. Signalling by these receptors depends upon their association with Janus kinases (JAKs), which couple ligand binding to tyrosine phosphorylation of signalling proteins recruited to the receptor complex. Among these are the signal transducers and activators of transcription (STATs), a family of transcription factors that contribute to the diversity of cytokine responses.

When the chimeric cytokine receptor of the invention binds its ligand, one or more of the following intracellular signaling pathways may be initiated:
   (i) the JAK-STAT pathway
   (ii) the MAP kinase pathway; and
   (iii) the Phosphoinositide 3-kinase (PI3K) pathway.

The JAK-STAT system consists of three main components: (1) a receptor (2) Janus kinase (JAK) and (3) Signal Transducer and Activator of Transcription (STAT).

JAKs, which have tyrosine kinase activity, bind to cell surface cytokine receptors. The binding of the ligand to the receptor triggers activation of JAKs. With increased kinase activity, they phosphorylate tyrosine residues on the receptor and create sites for interaction with proteins that contain phosphotyrosine-binding SH2 domains. STATs possessing SH2 domains capable of binding these phosphotyrosine residues are recruited to the receptors, and are themselves tyrosine-phosphorylated by JAKs. These phosphotyrosines then act as binding sites for SH2 domains of other STATs, mediating their dimerization. Different STATs form heteroor homodimers. Activated STAT dimers accumulate in the cell nucleus and activate transcription of their target genes.

Cytokine Receptor Endodomain

The chimeric cytokine receptor of the present invention comprises an endodomain which causes "cytokine-type" cell signalling (either alone or when in the presence of another chimeric cytokine receptor) when the exodomain binds its ligand.

The endodomain may be a cytokine receptor endodomain.

The endodomain may be derived from a type I cytokine receptor. Type I cytokine receptors share a common amino acid motif (WSXWS) in the extracellular portion adjacent to the cell membrane.

The endodomain may be derived from a type II cytokine receptor. Type II cytokine receptors include those that bind type I and type II interferons, and those that bind members of the interleukin-10 family (interleukin-10, interleukin-20 and interleukin-22).

Type I cytokine receptors include:
(i) Interleukin receptors, such as the receptors for IL-2, IL-3, IL-4, IL-5, IL-6, IL-7, IL-9, IL-11, IL-12, IL13, IL-15, IL-21, IL-23 and IL-27;
(ii) Colony stimulating factor receptors, such as the receptors for erythropoietin, GM-CSF, and G-CSF; and
(iii) Hormone receptor/neuropeptide receptor, such as hormone receptor and prolactin receptor Members of the type I cytokine receptor family comprise different chains, some of which are involved in ligand/cytokine interaction and others that are involved in signal transduction. For example the IL-2 receptor comprises an α-chain, a β-chain and a γ-chain.

The IL-2 receptor common gamma chain (also known as CD132) is shared between the IL-2 receptor, IL-4 receptor, IL-7 receptor, IL-9 receptor, IL-13 receptor and IL-15 receptor.

IL-2

IL-2 binds to the IL-2 receptor, which has three forms, generated by different combinations of three different proteins, often referred to as "chains": α, β and γ; these subunits are also parts of receptors for other cytokines. The β and γ chains of the IL-2R are members of the type I cytokine receptor family.

The three receptor chains are expressed separately and differently on various cell types and can assemble in different combinations and orders to generate low, intermediate, and high affinity IL-2 receptors.

The α chain binds IL-2 with low affinity, the combination of β and γ together form a complex that binds IL-2 with intermediate affinity, primarily on memory T cells and NK cells; and all three receptor chains form a complex that binds IL-2 with high affinity (Kd~10-11 M) on activated T cells and regulatory T cells.

The three IL-2 receptor chains span the cell membrane and extend into the cell, thereby delivering biochemical signals to the cell interior. The alpha chain does not participate in signalling, but the beta chain is complexed with the tyrosine phosphatase JAK1. Similarly the gamma chain complexes with another tyrosine kinase called JAK3. These enzymes are activated by IL-2 binding to the external domains of the IL-2R.

IL-2 signalling promotes the differentiation of T cells into effector T cells and into memory T cells when the initial T cells are also stimulated by an antigen. Through their role in the development of T cell immunologic memory, which depends upon the expansion of the number and function of antigen-selected T cell clones, they also have a key role in long-term cell-mediated immunity.

The chimeric cytokine receptor of the present invention may comprise the IL-2 receptor β-chain and/or the IL-2 receptor (i.e. common) γ-chain The amino acid sequences for the endodomains of the IL-2 β-chain and common γ-chain are shown as SEQ ID No. 1 and 2

SEQ ID No. 1: Endodomain derived from human common gamma chain:
ERTMPRIPTLKNLEDLVTEYHGNFSAWSGVSKGLAESLQPDYSERLCLVS
EIPPKGGALGEGPGASPCNQHSPYWAPPCYTLKPET SEQ ID No. 2: Endodomain derived from human IL-2Rβ:
NCRNTGPWLKKVLKCNTPDPSKFFSQLSSEHGGDVQKWLSSPFPSSSFSP

GGLAPEISPLEVLERDKVTQLLLQQDKVPEPASLSSNHSLTSCFTNQGYF

FFHLPDALEIEACQVYFTYDPYSEEDPDEGVAGAPTGSSPQPLQPLSGED

DAYCTFPSRDDLLLFSPSLLGGPSPPSTAPGGSGAGEERMPPSLQERVPR

DWDPQPLGPPTPGVPDLVDFQPPPELVLREAGEEVPDAGPREGVSFPWSR

PPGQGEFRALNARLPLNTDAYLSLQELQGQDPTHLV

The term "derived from" means that the endodomain of the chimeric cytokine receptor of the invention has the same sequence as the wild-type sequence of the endogenous molecule, or a variant thereof which retains the ability to form a complex with JAK-1 or JAK-3 and activate one of the signalling pathways mentioned above.

A "variant" sequence having at least 80, 85, 90, 95, 98 or 99% sequence identity to the wild-type sequence (e.g. SEQ ID Nos. 1 or 2), providing that the variant sequence retains the function of the wild-type sequence i.e. the ability to form a complex with JAK-1 or JAK-3 and activate, for example, the JAK-STAT signalling pathway.

The percentage identity between two polypeptide sequences may be readily determined by programs such as BLAST which is freely available at http COLON SLASH SLASH blast.ncbi.nlm.nih.gov.

IL-7

The interleukin-7 receptor is made up of two chains: the interleukin-7 receptor-α chain (CD127) and common-γ chain receptor (CD132). The common-γ chain receptors is shared with various cytokines, including interleukin-2, -4, -9, and -15. Interleukin-7 receptor is expressed on various cell types, including naive and memory T cells.

The interleukin-7 receptor plays a critical role in the development of lymphocytes, especially in V(D)J recombination. IL-7R also controls the accessibility of a region of the genome that contains the T-cell receptor gamma gene, by STAT5 and histone acetylation. Knockout studies in mice suggest that blocking apoptosis is an essential function of this protein during differentiation and activation of T lymphocytes.

The chimeric cytokine receptor of the present invention may comprise the IL-7 receptor α-chain and/or the IL-7 receptor (i.e. common) γ-chain, or a variant thereof.

The amino acid sequence for the endodomain of the IL-7 α-chain is shown as SEQ ID No. 3.

SEQ ID No. 3-Endodomain derived from human IL-7Rα:
KKRIKPIVWPSLPDHKKTLEHLCKKPRKNLNVSFNPESFLDCQIHRVDDI

QARDEVEGFLQDTFPQQLEESEKQRLGGDVQSPNCPSEDVVITPESFGRD

SSLTCLAGNVSACDAPILSSSRSLDCRESGKNGPHVYQDLLLSLGTTNST

LPPPFSLQSGILTLNPVAQGQPILTSLGSNQEEAYVTMSSFYQNQ

IL-15

Interleukin 15 (IL-15) is a cytokine with structural similarity to IL-2. Like IL-2, IL-15 binds to and signals through a complex composed of IL-2/IL-15 receptor beta chain (CD122) and the common gamma chain (gamma-C, CD132). IL-15 is secreted by mononuclear phagocytes (and some other cells) following viral infection. IL-15 induces cell proliferation of natural killer cells.

Interleukin-15 receptor consists of an interleukin 15 receptor alpha subunit and shares common beta and gamma subunits with the IL-2 receptor.

Spacer

The chimeric cytokine receptor of the present invention may comprise a spacer to connect the antigen-binding domain with the transmembrane domain and spatially separate the antigen-binding domain from the endodomain. A flexible spacer allows to the antigen-binding domain to orient in different directions to enable antigen binding.

Where the cell of the present invention comprises two or more chimeric cytokine receptors, the spacers may be the same or different. Where the cell of the present invention comprises a chimeric cytokine receptor (CCR) and a chimeric antigen receptor (CAR), the spacer of the CCR and the CAR may be different, for example, having a different length. The spacer of the CAR may be longer than the spacer of the or each CCR.

The spacer sequence may, for example, comprise an IgG1 Fc region, an IgG1 hinge or a CD8 stalk. The linker may alternatively comprise an alternative linker sequence which has similar length and/or domain spacing properties as an IgG1 Fc region, an IgG1 hinge or a CD8 stalk.

A human IgG1 spacer may be altered to remove Fc binding motifs.

Examples of amino acid sequences for these spacers are given below:

```
SEQ ID No. 4 (hinge-CH2CH3 of human IgG1)
AEPKSPDKTHTCPPCPAPPVAGPSVFLFPPKPKDTLMIARTPEVTCVVVD

VSHEDPEVKFNVVYVDGVEVHNAKTKPREEQYNSTYRVVSVLTVLHQDWL

NGKEYKCKVSNKALPAPIEKTISKAKGQPREPQVYTLPPSRDELTKNQVS

LTCLVKGFYPSDIAVEWESNGQPENNYKTTPPVLDSDGSFFLYSKLTVDK

SRWQQGNVFSCSVMHEALHNHYTQKSLSLSPGKKD

SEQ ID No. 5 (human CD8 stalk):
TTTPAPRPPTPAPTIASQPLSLRPEACRPAAGGAVHTRGLDFACDI

SEQ ID No. 6 (human IgG1 hinge):
AEPKSPDKTHTCPPCPKDPK
```

Transmembrane Domain

The transmembrane domain is the sequence of a CCR that spans the membrane. It may comprise a hydrophobic alpha helix. The transmembrane domain may be derived from CD28, which gives good receptor stability.

Alternatively the transmembrane domain may be derived from a cytokine receptor, for example the same cytokine from which the endodomain is derived.

The transmembrane domain may, for example be derived from IL-2R, IL-7R or IL-15R.

```
SEQ ID No. 7-Transmembrane derived from human
common gamma chain:
VVISVGSMGLIISLLCVYFWL SEQ ID No. 8-Transmembrane derived from human
IL-2Rβ:
IPWLGHLLVGLSGAFGFIILVYLLI SEQ ID No. 9-Transmembrane derived from human
IL-7Rα:
PILLTISILSFFSVALLVILACVLW SEQ ID No. 10-Transmembrane derived from human
IL-15Rα:
AISTSTVLLCGLSAVSLLACYL
```

Ligand-Binding Exodomain

The ligand binding domain comprises an antigen binding domain. The antigen binding domain binds the target ligand for the CCR, i.e. the tumour secreted factor or chemokine or cell surface antigen.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; the binding domain from a natural receptor for the target antigen; a peptide with sufficient affinity for the target ligand; a single domain binder such as a camelid; an artificial binder single as a Darpin; or a single-chain derived from a T-cell receptor.

The term "ligand" is used synonymously with "antigen" to mean an entity which is specifically recognised and bound by the antigen-binding domain of the CCR.

Where the ligand is a tumour secreted factor, the antigen binding domain may comprise an immunoglobulin-based antigen binding site, such as an scFv or a single domain binder.

Where the ligand is a chemokine, the antigen binding domain may comprise the chemokine-binding portion of a natural receptor for the chemokine.

Ligand

The CCR of the present invention binds ligand.

The ligand may be a soluble ligand such as a tumour secreted factor or a chemokine.

Alternatively, the ligand may be a membrane bound ligand, such as a cell surface antigen.

The term "soluble ligand" is used to indicate a ligand or antigen which is not part of or attached to a cell but which moves freely in the extracellular space, for example in a bodily fluid of the tissue of interest. The soluble ligand may exist in a cell-free state in the serum, plasma or other bodily fluid of an individual.

The soluble ligand may be associated with the presence or pathology of a particular disease, such as cancer.

The soluble ligand may be part of the cancer secretome, i.e. the collection of factors secreted by a tumour, be it from cancer stem cells, non-stem cells or the surrounding stroma. The soluble ligand may be secreted or shed by tumour cells (see next section).

The soluble ligand may be characteristic of a disease or of diseased tissue. It may be found exclusively, or at a higher level in a subject having the disease vs a healthy subject; or in diseased tissue vs healthy tissue. The soluble ligand may be expressed at at least a 2-fold, 5-fold, 10-fold, 100-fold, 1000-fold, 10,000-fold or 100,000 fold higher level a subject having the disease vs a healthy subject; or in diseased tissue vs healthy tissue.

The terms "cell-surface antigen" and "cell-surface ligand" is used synonymously with "membrane-bound antigen" and "membrane-bound ligand" to mean a ligand which is attached to or expressed on the surface of the cell. The cell-surface ligand may, for example, be a transmembrane protein.

The cell on which the cell-surface ligand is found may be a target cell, such as a cancer cell.

The cell-surface ligand may be associated with the presence or pathology of a particular disease, such as cancer. Alternatively the cell-surface ligand may be characteristic of the cell type of the target cell (e.g. B-cell) without being necessarily associated with the diseased state.

Where the cell-surface ligand is characteristic of a disease or of diseased tissue it may be found exclusively, or at a higher level on the relevant cells a subject having the disease vs a healthy subject; or in diseased tissue vs healthy tissue. The cell-surface ligand may be expressed at at least a 2-fold, 5-fold, 10-fold, 100-fold, 1000-fold, 10,000-fold or 100,000 fold higher level on a cell of a subject having the disease vs a healthy subject; or in diseased tissue vs healthy tissue.

Tumour Secreted Factor

The ligand recognised by the CCR may be a soluble ligand secreted by or shedded from a tumour.

This "tumour secreted factor" may, for example, be prostate-specific antigen (PSA), carcinoembryonic antigen (CEA), vascular endothelial growth factor (VEGF) or Cancer Antigen-125 (CA-125).

The tumour secreted factor may be a soluble ligand which is not a cytokine. The CCR of the present invention therefore grafts the binding specificity for a non-cytokine ligand on to the endodomain of a cytokine receptor.

Prostate-Specific Antigen (PSA)

The soluble ligand may be prostate-specific antigen (PSA).

Prostate-specific antigen (PSA), also known as gamma-seminoprotein or kallikrein-3 (KLK3), is a glycoprotein enzyme encoded in humans by the KLK3 gene. PSA is a member of the kallikrein-related peptidase family and is secreted by the epithelial cells of the prostate gland.

PSA is present in small quantities in the serum of men with healthy prostates, but is elevated in individuals with prostate cancer and other prostate disorders.

PSA is a 237-residue glycoprotein and is activated by KLK2. Its physiological role is the liquefaction of the coagulum components of the semen leading to liberation of spermatozoa. In cancer, PSA may participate in the processes of neoplastic growth and metastasis.

PSA is a chymotrypsin-like serine protease with a typical His-Asp-Ser triad and a catalytic domain similar to those of other kallikrein-related peptidases. The crystal structure of PSA has been obtained i) in complex with the monoclonal antibody (mAb) 8G8F5 and ii) in a sandwich complex with two mAbs 5D5A5 and 5D3D11 (Stura et al (J. Mol. Biol. (2011) 414:530-544).

Various monoclonal antibodies are known, including clones 2G2-B2, 2D8-E8, IgG1/K described in Bavat et al Avicenna J. Med. Biotechnol. 2015, 7:2-7; and Leinonen (2004) 289:157-67.

The CCR of the present invention may, for example, comprise the 6 CDRs or the VH and/or VL domain(s) from a PSA-binding mAb such as 8G8F5, 5D5A5 or 5D3D11.

Where the CCR comprises two antigen binding specificities, binding different epitopes on PSA, one may be based on, for example 5D3D11 and one may be based on, for example, 5D5A5.

The amino acid sequences for 5D3D11 and 5D5A5 VH and VL are given below. The complementarity determining regions (CDRs) are highlighted in bold.

5D3D11 VH
(SEQ ID No. 11)
QVQLQQSGPELVKPGASVKISCKVSGYAISSSWMNWVKQRPGQGLEWIGR
IYPGDGDTKYNGKFKDKATLTVDKSSSTAYMQLSSLTSVDSAVYFCARDG
YRYYFDYWGQGTSVTVSS

5D3D11 VL
(SEQ ID No. 12)
DIVMTQTAPSVFVTPGESVSISCRSSKSLLHSNGNTYLYWFLQRPGQSPQ
LLIYRMSNLASGVPDRFSGSGSGTDFTLRISRVEAEDVGVYYCMQHLEYP
VTFGAGTKVEIK

5D5A5 VH
(SEQ ID No. 13)
QVQLQQSGAELAKPGASVKMSCKTSGYSFSSYWMHWVKQRPGQGLEWIGY
INPSTGYTENNQKFKDKVTLTADKSSNTAYMQLNSLTSEDSAVYYCARSG
RLYFDVWGAGTTVTVSS

5D5A5 VL
(SEQ ID No. 14)
DIVLTQSPPSLAVSLGQRATISCRASESIDLYGFTFMHWYQQKPGQPPKI
LIYRASNLESGIPARFSGSGSRTDFTLTINPVEADDVATYYCQQTHEDPY
TFGGGTKLEIK

ScFv based on 5D5A5
(SEQ ID No. 15)
QVQLQQSGAELAKPGASVKMSCKTSGYSFSSYVVMHWVKQRPGQGLEWIG

YINPSTGYTENNQKFKDKVTLTADKSSNTAYMQLNSLTSEDSAVYYCARS

GRLYFDVWGAGTTVTVSSGGGGSGGGGSGGGGSGGGGSDIVLTQSPPSLA

VSLGQRATISCRASESIDLYGFTFMHWYQQKPGQPPKILIYRASNLESGI

PARFSGSGSRTDFTLTINPVEADDVATYYCQQTHEDPYTFGGGTKLEIK

ScFv based on 5D3D11
(SEQ ID No. 16)
QVQLQQSGPELVKPGASVKISCKVSGYAISSSWMNWVKQRPGQGLEWIGR

IYPGDGDTKYNGKFKDKATLTVDKSSSTAYMQLSSLTSVDSAVYFCARDG

YRYYFDYWGQGTSVTVSSGGGGSGGGGSGGGGSGGGGSDIVMTQTAPSVF

VTPGESVSISCRSSKSLLHSNGNTYLYWFLQRPGQSPQLLIYRMSNLASG

VPDRFSGSGSGTDFTLRISRVEAEDVGVYYCMQHLEYPVTFGAGTKVEIK

Where a cell comprises two CCRs, the antigen-binding domain of the first CCR may comprise the 6 CDRs from 5D5A5 and the antigen-binding domain of the second CCR may comprise the 6 CDRs from 5D3D11.

The antigen-binding domain of the first CCR may comprise the VH and/or VL domain(s) from 5D5A5 or a variant thereof; and the antigen-binding domain of the second CCR may comprise the VH and/or VL domain(s) from 5D3D11 or a variant thereof. Variant VH and VL domains may have at least 80, 90, 95 or 99% identity to the sequences given above, provided that they retain PSA-binding activity.

A cell expressing a CCR which binds PSA may be useful in the treatment of prostate cancer.

Carcinoembryonic Antigen (CEA)

The soluble ligand may be CEA.

Carcinoembryonic antigen (CEA) describes a set of highly related glycoproteins involved in cell adhesion. CEA is normally produced in gastrointestinal tissue during fetal development, but the production stops before birth. Therefore CEA is usually present only at very low levels in the blood of healthy adults. However, the serum levels are raised in some types of cancer, which means that it can be used as a tumor marker in clinical tests.

CEA are glycosyl phosphatidyl inositol (GPI) cell surface anchored glycoproteins whose specialized sialofucosylated glycoforms serve as functional colon carcinoma L-selectin and E-selectin ligands, which may be critical to the metastatic dissemination of colon carcinoma cells. Immunologically they are characterized as members of the CD66 cluster of differentiation.

CEA and related genes make up the CEA family belonging to the immunoglobulin superfamily. In humans, the carcinoembryonic antigen family consists of 29 genes, 18 of which are normally expressed. The following is a list of human genes which encode carcinoembryonic antigen-related cell adhesion proteins: CEACAM1, CEACAM3, CEACAM4, CEACAM5, CEACAM6, CEACAM7, CEACAM8, CEACAM16, CEACAM18, CEACAM19, CEACAM20, CEACAM21

Various antibodies which target CEA are described in WO 2011/034660.

A cell expressing a CCR against CEA may be useful in the treatment of, for example, colorectal cancer.

Vascular Endothelial Growth Factor (VEGF)

The soluble ligand may be VEGF.

Vascular endothelial growth factor (VEGF) is a signal protein produced by cells that stimulates vasculogenesis and angiogenesis. It is part of the system that restores the oxygen supply to tissues when blood circulation is inadequate. Serum concentration of VEGF is high in bronchial asthma and diabetes mellitus. VEGF's normal function is to create new blood vessels during embryonic development, new blood vessels after injury, muscle following exercise, and new vessels (collateral circulation) to bypass blocked vessels.

When VEGF is overexpressed, it can contribute to disease. Solid cancers cannot grow beyond a limited size without an adequate blood supply; cancers that can express VEGF are able to grow and metastasize.

VEGF is a sub-family of the platelet-derived growth factor family of cystine-knot growth factors. They are important signaling proteins involved in both vasculogenesis (the de novo formation of the embryonic circulatory system) and angiogenesis (the growth of blood vessels from pre-existing vasculature).

The VEGF family comprises in mammals five members: VEGF-A, placenta growth factor (PGF), VEGF-B, VEGF-C and VEGF-D.

Various antibodies to VEGF are known, such as bevacizumab (Avastin) and Ranibizumab (Lucentis).

Cancer Antigen 125 (CA-125)

CA-125 is associated with ovarian cancer and is the most frequently used biomarker for ovarian cancer detection. While CA-125 is best known as a marker for ovarian cancer, it may also be elevated in other cancers, including endometrial cancer, fallopian tube cancer, lung cancer, breast cancer and gastrointestinal cancer.

The sequence of human CA-125 (also known as mucin-16) is available from NCBI, Accession No. 078966.

A number of CA125-binding monoclonal antibodies are known, including OC125 and M11 (Nustad et al 1996, Tumour Biol. 17:196-329). In this study the specificity of 26 monoclonal antibodies against the CA 125 antigen was investigated. It was found that the CA 125 antigen carries only two major antigenic domains, which classifies the antibodies as OC125-like (group A) or M11-like (group B).

The chimeric cytokine receptor of the present invention may comprise an antigen-binding domain from such an antibody. A cell comprising such a CCR may be useful in the treatment of, for example, ovarian cancer.

The tumour secreted factor (or, if in a membrane-bound form, the transmembrane protein) may be selected from the following non-exhaustive list:

ALK gene rearrangements and overexpression giving mutated forms of ALK proteins
Alpha-fetoprotein (AFP)
Beta-2-microglobulin (B2M)
Beta-human chorionic gonadotropin (Beta-hCG)
BRAF V600 mutations giving mutated B-REF protein
C-kit/CD117
CA15-3/CA27.29
CA19-9
Calcitonin
CD20
Chromogranin A (CgA)
Cytokeratin fragment 21-1
EGFR gene mutation analysis
Estrogen receptor (ER)/progesterone receptor (PR)
Fibrin/fibrinogen
HE4
HER2/neu gene amplification or protein overexpression
Immunoglobulins
KRAS gene mutation analysis
Lactate dehydrogenase
Neuron-specific enolase (NSE)
Nuclear matrix protein 22
Programmed death ligand 1 (PD-L1)
Thyroglobulin
Urokinase plasminogen activator (uPA) and plasminogen activator inhibitor (PAI-1)

Chemokine

Chemokines are chemotactic cytokines. Cell migration is guided by chemokine gradients embedded and immobilized in extracellular matrix. The positively charged chemokines like CXCL12 bind to negatively charged ECM molecules. These gradients provide tracks for cancer cell and immune cell homing. The action on T cells seems to be inhibitory for the homing of cytotoxic T cells, while regulatory T cells appear to be attracted.

Chemokines are approximately 8-10 kilodaltons in mass and have four cysteine residues in conserved locations which are key to forming their 3-dimensional shape.

Some chemokines are considered pro-inflammatory and can be induced during an immune response to recruit cells of the immune system to a site of infection, while others are considered homeostatic and are involved in controlling the migration of cells during normal processes of tissue maintenance or development.

Chemokines have been classified into four main subfamilies: CXC, CC, CX3C and XC. All of these proteins exert their biological effects by interacting with G protein-linked transmembrane receptors called chemokine receptors that are selectively found on the surfaces of their target cells.

The major role of chemokines is to act as a chemoattractant to guide the migration of cells. Cells that are attracted by chemokines follow a signal of increasing chemokine concentration towards the source of the chemokine. Some chemokines control cells of the immune system during processes of immune surveillance, such as directing lymphocytes to the lymph nodes so they can screen for invasion of pathogens by interacting with antigen-presenting cells residing in these tissues. Other chemokines are inflammatory and are released from a wide variety of cells in response to bacterial infection, viruses and other agents. Their release is often stimulated by pro-inflammatory cytokines such as interleukin 1. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. They are released by many different cell types and serve to guide cells of both innate immune system and adaptive immune system.

CC Chemokines

The CC chemokine (or β-chemokine) proteins have two adjacent cysteines (amino acids), near their amino terminus. There have been at least 27 distinct members of this subgroup reported for mammals, called CC chemokine ligands (CCL)-1 to -28; CCL10 is the same as CCL9. Chemokines of this subfamily usually contain four cysteines (C4-CC chemokines), but a small number of CC chemokines possess six cysteines (C6-CC chemokines). C6-CC chemokines include CCL1, CCL15, CCL21, CCL23 and CCL28. CC chemokines induce the migration of monocytes and other cell types such as NK cells and dendritic cells.

Examples of CC chemokine include monocyte chemoattractant protein-1 (MCP-1 or CCL2) which induces monocytes to leave the bloodstream and enter the surrounding tissue to become tissue macrophages.

CCL5 (or RANTES) attracts cells such as T cells, eosinophils and basophils that express the receptor CCR5.

CXC Chemokines

The two N-terminal cysteines of CXC chemokines (or α-chemokines) are separated by one amino acid, represented in this name with an "X". There have been 17 different CXC chemokines described in mammals, that are subdivided into two categories, those with a specific amino acid sequence (or motif) of glutamic acid-leucine-arginine (or ELR for short) immediately before the first cysteine of the CXC motif (ELR-positive), and those without an ELR motif (ELR-negative). ELR-positive CXC chemokines specifically induce the migration of neutrophils, and interact with chemokine receptors CXCR1 and CXCR2.

C Chemokines

The third group of chemokines is known as the C chemokines (or γ chemokines), and is unlike all other chemokines in that it has only two cysteines; one N-terminal cysteine and one cysteine downstream. Two chemokines have been described for this subgroup and are called XCL1 (lymphotactin-α) and XCL2 (lymphotactin-β).

CX3C Chemokine

CX3C chemokines have three amino acids between the two cysteines. The only CX3C chemokine discovered to date is called fractalkine (or CX3CL1). It is both secreted and tethered to the surface of the cell that expresses it, thereby serving as both a chemoattractant and as an adhesion molecule.

Chemokine receptors are G protein-coupled receptors containing 7 transmembrane domains that are found on the surface of leukocytes. Approximately 19 different chemokine receptors have been characterized to date, which are divided into four families depending on the type of chemokine they bind; CXCR that bind CXC chemokines, CCR that bind CC chemokines, CX3CR1 that binds the sole CX3C chemokine (CX3CL1), and XCR1 that binds the two XC chemokines (XCL1 and XCL2). They share many structural features; they are similar in size (with about 350 amino acids), have a short, acidic N-terminal end, seven helical transmembrane domains with three intracellular and three extracellular hydrophilic loops, and an intracellular C-terminus containing serine and threonine residues important for receptor regulation. The first two extracellular loops of chemokine receptors each has a conserved cysteine residue that allow formation of a disulfide bridge between these loops. G proteins are coupled to the C-terminal end of the chemokine receptor to allow intracellular signaling after receptor activation, while the N-terminal domain of the chemokine receptor determines ligand binding specificity.

CXCL12

CXCL12 is strongly chemotactic for lymphocytes. CXCL12 plays an important role in angiogenesis by recruiting endothelial progenitor cells (EPCs) from the bone marrow through a CXCR4 dependent mechanism. It is this function of CXCL12 that makes it a very important factor in carcinogenesis and the neovascularisation linked to tumour progression. CXCL12 also has a role in tumour metastasis where cancer cells that express the receptor CXCR4 are attracted to metastasis target tissues that release the ligand, CXCL12.

The receptor for CXCL12 is CXCR4. The CCR of the present invention may comprise the CXCL12-binding domain from CXCR4 linked to an endodomain derived from a cytokine receptor, such as the IL-2 receptor.

CXCR4 coupled expression of IL2 would support engraftment of therapeutic T cell for cancer therapies. In multiple myeloma, a cell expressing such a CCR may mobilize cells and change the bone marrow environment. Such cells also have uses in the treatment of solid cancers by modifying the solid tumour microenvironment.

The amino acid sequence for CXCR4 is shown below as SEQ ID No. 17

```
                                                              SEQ ID No. 17
  1    msiplpllqi ytsdnyteem gsgdydsmke pcfreenanf nkiflptiys iifltgivgn 61    glvilvmgyq kklrsmtdky rlhlsvadll fvitlpfwav davanwyfgn flckavhviy 121    tvnlyssvli lafisldryl aivhatnsqr prkllaekvv yvgvwipall ltipdfifan
181    vseaddryic drfypndlwv vvfqfqhimv glilpgivil scyciiiskl shskghqkrk 241    alkttvilil affacwlpyy igisidsfil leiikqgcef entvhkwisi tealaffhcc 301    lnpilyaflg akfktsaqha ltsysrgssl kilskgkrgg hssvsteses ssfhss
```

CXCR7 also binds CXCL12.

CCL2

The chemokine (C-C motif) ligand 2 (CCL2) is also referred to as monocyte chemotactic protein 1 (MCP1) and small inducible cytokine A2. CCL2 recruits monocytes, memory T cells, and dendritic cells to the sites of inflammation produced by either tissue injury or infection.

CCR2 and CCR4 are two cell surface receptors that bind CCL2.

CCR2 has the amino acid sequence shown as SEQ ID No. 18

```
                                                      SEQ ID No. 18
  1   mlstsrsrfi rntnesgeev ttffdydyga pchkfdvkqi gaqllpplys lvfifgfvgn 61   mlvvlilinc kklkcltdiy llnlaisdll flitlplwah saanewvfgn amcklftgly 121   higyfggiff iilltidryl aivhavfalk artvtfgvvt svitwlvavf asvpgiiftk 181   cqkedsvyvc gpyfprgwnn fhtimrnilg lvlpllimvi cysgilktll rcrnekkrhr 241   avrviftimi vyflfwtpyn ivillntfqe ffglsncest sqldqatqvt etlgmthcci 301   npiiyafvge kfrslfhial gcriaplqkp vcggpgvrpg knvkvttqgl ldgrgkgksi 361   grapeaslqd kega
```

CCR4 has the amino acid sequence shown as SEQ ID No. 19.

```
                                                      SEQ ID No. 19
  1   mnptdiadtt ldesiysnyy lyesipkpct kegikafgel flpplyslvf vfgllgnsvv 61   vlvlfkykrl rsmtdvylln laisdllfvf slpfwgyyaa dqwvfglglc kmiswmylvg 121   fysgiffvml msidrylaiv havfslrart ltygvitsla twsvavfasl pgflfstcyt 181   ernhtycktk yslnsttwkv lssleinilg lviplgimlf cysmiirtlq hcknekknka 241   vkmifavvvl flgfwtpyni vlfletlvel evlqdctfer yldyaiqate tlafvhccln 301   piiyfflgek frkyilqlfk tcrglfvlcq ycgllqiysa dtpsssytqs tmdhdlhdal
```

The CCR of the present invention may comprise the CCL2 binding site of CCR2 or CCR4 in its ligand binding domain.

Cell-Surface Antigen

The ligand may be a cell-surface antigen, such as a transmembrane protein.

The cell surface antigen may be CD22.

CD22, or cluster of differentiation-22, is a molecule belonging to the SIGLEC family of lectins. It is found on the surface of mature B cells and to a lesser extent on some immature B cells. Generally speaking, CD22 is a regulatory molecule that prevents the overactivation of the immune system and the development of autoimmune diseases.

CD22 is a sugar binding transmembrane protein, which specifically binds sialic acid with an immunoglobulin (Ig) domain located at its N-terminus. The presence of Ig domains makes CD22 a member of the immunoglobulin superfamily. CD22 functions as an inhibitory receptor for B cell receptor (BCR) signalling.

Increased expression of CD22 is seen in non-Hodgkin and other lymphomas. Various monoclonal antibodies targeting CD22 are known, including epratuzumab, inotuzumab ozogamicin, m971 and m972.

Chimeric Antigen Receptors (CAR)

The cell of the present invention may also comprise one or more chimeric antigen receptor(s). The CAR(s) may be specific for a tumour-associated antigen.

Classical CARs are chimeric type I trans-membrane proteins which connect an extracellular antigen-recognizing domain (binder) to an intracellular signalling domain (endodomain). The binder is typically a single-chain variable fragment (scFv) derived from a monoclonal antibody (mAb), but it can be based on other formats which comprise an antibody-like or ligand-based antigen binding site. A trans-membrane domain anchors the protein in the cell membrane and connects the spacer to the endodomain.

Early CAR designs had endodomains derived from the intracellular parts of either the γ chain of the FcεR1 or CD3ζ. Consequently, these first generation receptors transmitted immunological signal 1, which was sufficient to trigger T-cell killing of cognate target cells but failed to fully activate the T-cell to proliferate and survive. To overcome this limitation, compound endodomains have been constructed: fusion of the intracellular part of a T-cell co-stimulatory molecule to that of CD3ζ results in second generation receptors which can transmit an activating and co-stimulatory signal simultaneously after antigen recognition. The co-stimulatory domain most commonly used is that of CD28. This supplies the most potent co-stimulatory signal—namely immunological signal 2, which triggers T-cell proliferation. Some receptors have also been described which include TNF receptor family endodomains, such as the closely related OX40 and 41BB which transmit survival signals. Even more potent third generation CARs have now been described which have endodomains capable of transmitting activation, proliferation and survival signals.

CAR-encoding nucleic acids may be transferred to T cells using, for example, retroviral vectors. In this way, a large number of antigen-specific T cells can be generated for adoptive cell transfer. When the CAR binds the target-antigen, this results in the transmission of an activating signal to the T-cell it is expressed on. Thus the CAR directs the specificity and cytotoxicity of the T cell towards cells expressing the targeted antigen.

The cell of the present invention may comprise one or more CAR(s).

The CAR(s) may comprise an antigen-binding domain, a spacer domain, a transmembrane domain and an endodomain. The endodomain may comprise or associate with a domain which transmit T-cell activation signals.

CAR Antigen Binding Domain

The antigen-binding domain is the portion of a CAR which recognizes antigen.

Numerous antigen-binding domains are known in the art, including those based on the antigen binding site of an antibody, antibody mimetics, and T-cell receptors. For example, the antigen-binding domain may comprise: a single-chain variable fragment (scFv) derived from a monoclonal antibody; a natural ligand of the target antigen; a peptide with sufficient affinity for the target; a single domain binder such as a camelid; an artificial binder single as a Darpin; or a single-chain derived from a T-cell receptor.

The term "ligand" is used synonymously with "antigen" to mean an entity which is specifically recognised and bound by the antigen-binding domain of a CAR.

Cell Surface Antigen

The CAR may recognise a cell-surface antigen, i.e. an entity, such as a transmembrane protein which is expressed on the surface of a target cell, such as a tumour cell.

The CAR may specifically bind a tumour-associated cell-surface antigen.

Various tumour associated antigens (TAA) are known, some of which are shown in Table 1. The antigen-binding domain used in the present invention may be a domain which is capable of binding a TAA as indicated therein.

TABLE 1

| Cancer type | TAA |
|---|---|
| Diffuse Large B-cell Lymphoma | CD19, CD20, CD22 |
| Breast cancer | ErbB2, MUC1 |
| AML | CD13, CD33 |
| Neuroblastoma | GD2, NCAM, ALK, GD2 |
| B-CLL | CD19, CD52, CD160 |
| Colorectal cancer | Folate binding protein, CA-125 |
| Chronic Lymphocytic Leukaemia | CD5, CD19 |
| Glioma | EGFR, Vimentin |
| Multiple myeloma | BCMA, CD138 |
| Renal Cell Carcinoma | Carbonic anhydrase IX, G250 |
| Prostate cancer | PSMA |
| Bowel cancer | A33 |

Where the CAR recognises a B-cell lymphoma or leukemia antigen (such as CD19, CD20, CD52, CD160 or CD5), the CCR may recognise another B-cell antigen, such as CD22.

Prostate-Cancer Associated Antigens

The CAR may specifically bind a cell-surface antigen associated with prostate cancer, such as prostate stem cell antigen (PSCA) or prostate-specific membrane antigen (PSMA).

PSCA is a glycosylphosphatidylinositol-anchored cell membrane glycoprotein. It is is up-regulated in a large proportion of prostate cancers and is also detected in cancers of the bladder and pancreas.

Various anti-PSCA antibodies are known, such as 7F5 (Morgenroth et al (Prostate (2007) 67:1121-1131); 1G8 (Hillerdal et al (2014) BMC Cancer 14:30); and Ha1-4.117 (Abate-Daga et al (2014) 25:1003-1012).

The CCR-expressing cell of the invention may also express an anti-PSCA CAR which may comprise an antigen binding domain based on one of these antibodies.

PSMA is is a zinc metalloenzyme that resides in membranes. PSMA is strongly expressed in the human prostate, being a hundredfold greater than the expression in most other tissues. In cancer, it is upregulated in expression and has been called the second-most-upregulated gene in prostate cancer, with increase of 8- to 12-fold over the noncancerous prostate. In addition to the expression in the human prostate and prostate cancer, PSMA is also found to be highly expressed in tumor neovasculature but not normal vasculature of all types of solid tumors, such as kidney, breast, colon, etc.

Various anti-PSMA antibodies are known, such as 7E11, J591, J415, and Hybritech PEQ226.5 and PM2J004.5 each of which binds a distinct epitope of PSMA (Chang et al (1999) Cancer Res 15:3192-8).

The CCR-expressing cell of the invention may also express an anti-PSMA CAR which may comprise an antigen binding domain based on one of these antibodies.

For example, the CCR may comprise an scFv based on J591, having the sequence shown as SEQ ID No. 20.

```
(J591 scFv)
                                         SEQ ID No. 20
EVQLQQSGPELKKPGTSVRISCKTSGYTFTEYTIHWVKQSHGKSLEWIGN

INPNNGGTTYNQKFEDKATLTVDKSSSTAYMELRSLTSEDSAVYYCAAGW

NFDYWGQGTTLTVSSGGGGSGGGGSGGGGSDIVMTQSHKFMSTSVGDRVS

IICKASQDVGTAVDWYQQKPGQSPKWYWASTRHTGVPDRFTGSGSGTDFT

LTITNVQSEDLADYFCQQYNSYPLTFGAGTMLDLKR
```

CAR Transmembrane Domain

The transmembrane domain is the sequence of a CAR that spans the membrane. It may comprise a hydrophobic alpha helix. The CAR transmembrane domain may be derived from CD28, which gives good receptor stability.

CAR Signal Peptide

The CAR and CCR described herein may comprise a signal peptide so that when it/they is expressed in a cell, such as a T-cell, the nascent protein is directed to the endoplasmic reticulum and subsequently to the cell surface, where it is expressed.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the sequence shown as SEQ ID No. 21, 22 or 23 or a variant thereof having 5, 4, 3, 2 or 1 amino acid mutations (insertions, substitutions or additions) provided that the signal peptide still functions to cause cell surface expression of the CAR.

```
SEQ ID No. 21:
MGTSLLCWMALCLLGADHADG
```

The signal peptide of SEQ ID No. 21 is compact and highly efficient and is derived from TCR beta chain. It is predicted to give about 95% cleavage after the terminal glycine, giving efficient removal by signal peptidase.

```
SEQ ID No. 22:
MSLPVTALLLPLALLLHAARP
```

The signal peptide of SEQ ID No. 22 is derived from IgG1.

SEQ ID No. 23:
MAVPTQVLGLLLLWLTDARC

The signal peptide of SEQ ID No. 23 is derived from CD8a.

CAR Endodomain

The endodomain is the portion of a classical CAR which is located on the intracellular side of the membrane.

The endodomain is the signal-transmission portion of a classical CAR. After antigen recognition by the antigen binding domain, individual CAR molecules cluster, native CD45 and CD148 are excluded from the synapse and a signal is transmitted to the cell.

The CAR endodomain may be or comprise an intracellular signalling domain. In an alternative embodiment, the endodomain of the present CAR may be capable of interacting with an intracellular signalling molecule which is present in the cytoplasm, leading to signalling.

The intracellular signalling domain or separate intracellular signalling molecule may be or comprise a T cell signalling domain.

The most commonly used signalling domain component is that of CD3-zeta endodomain, which contains 3 ITAMs. This transmits an activation signal to the T cell after antigen is bound. CD3-zeta may not provide a fully competent activation signal and additional co-stimulatory signalling may be needed. For example, chimeric CD28 and OX40 can be used with CD3-Zeta to transmit a proliferative/survival signal, or all three can be used together.

The CAR may comprise the CD3-Zeta endodomain alone, the CD3-Zeta endodomain with that of either CD28 or OX40 or the CD28 endodomain and OX40 and CD3-Zeta endodomain.

The CAR endodomain may comprise one or more of the following: an ICOS endodomain, a CD27 endodomain, a BTLA endodomain, a CD30 endodomain, a GITR endodomain and an HVEM endodomain.

The endomain may comprise the sequence shown as SEQ ID No. 24 to 32 or a variant thereof having at least 80% sequence identity.

-CD3 Z endodomain
SEQ ID No. 24
RVKFSRSADAPAYQQGQNQLYNELNLGRREEYDVLDKRRGRDPEMGGKPR
RKNPQEGLYNELQKDKMAEAYSEIGMKGERRRGKGHDGLYQGLSTATKDT
YDALHMQALPPR -CD28 and CD3 Zeta endodomains
SEQ ID No. 25
SKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQALP

PR

-CD28, OX40 and CD3 Zeta endodomains
SEQ ID No. 26
SKRSRLLHSDYMNMTPRRPGPTRKHYQPYAPPRDFAAYRSRDQRLPPDAH

KPPGGGSFRTPIQEEQADAHSTLAKIRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPR

-ICOS endodomain
SEQ ID No. 27
CWLTKKKYSSSVHDPNGEYMFMRAVNTAKKSRLTDVTL

-CD27 endodomain
SEQ ID No. 28
QRRKYRSNKGESPVEPAEPCHYSCPREEEGSTIPIQEDYRKPEPACSP

-BTLA endodomain
SEQ ID No. 29
RRHQGKQNELSDTAGREINLVDAHLKSEQTEASTRQNSQVLLSETGIYDN
DPDLCFRMQEGSEVYSNPCLEENKPGIVYASLNHSVIGPNSRLARNVKEA
PTEYASICVRS -CD30 endodomain
SEQ ID No. 30
HRRACRKRIRQKLHLCYPVQTSQPKLELVDSRPRRSSTQLRSGASVTEPV

AEERGLMSQPLMETCHSVGAAYLESLPLQDASPAGGPSSPRDLPEPRVST

EHTNNKIEKIYIMKADTVIVGTVKAELPEGRGLAGPAEPELEEELEADHT

PHYPEQETEPPLGSCSDVMLSVEEEGKEDPLPTAASGK

-GITR endodomain
SEQ ID No. 31
QLGLHIWQLRSQCMWPRETQLLLEVPPSTEDARSCQFPEEERGERSAEEK
GRLGDLWV -HVEM endodomain
SEQ ID No. 32
CVKRRKPRGDVVKVIVSVQRKRQEAEGEATVIEALQAPPDVTTVAVEETI
PSFTGRSPNH A variant sequence may have at least 80%, 85%, 90%, 95%, 98% or 99% sequence identity to SEQ ID No. 24 to 32, provided that the sequence provides an effective intracellular signalling domain.

Nucleic Acid

The present invention also provides a nucleic acid encoding a CCR of the invention.

The nucleic acid may have the structure:
AgB-spacer-TM-endo
in which
AgB1 is a nucleic acid sequence encoding the antigen-binding domain of the CCR;
spacer 1 is a nucleic acid sequence encoding the spacer of the CCR;
TM1 is a nucleic acid sequence encoding the transmembrane domain of the CCR;
endo 1 is a nucleic acid sequence encoding the endodomain of the CCR.

Nucleic Acid Construct

The present invention further provides a nucleic acid construct which comprises a first nucleic acid sequence encoding a first CCR as defined in connection with the first aspect of the invention; and a second nucleic acid sequence encoding a second CCR as defined in connection with the first aspect of the invention.

The nucleic acid construct may have the following structure:
AgB1-spacer1-TM1-endo1-coexpr-AgB2-spacer2-TM2-endo2
in which
AgB1 is a nucleic acid sequence encoding the antigen-binding domain of the first CCR;
spacer 1 is a nucleic acid sequence encoding the spacer of the first CCR;
TM1 is a nucleic acid sequence encoding the transmembrane domain of the first CCR;
endo 1 is a nucleic acid sequence encoding the endodomain of the first CCR;

coexpr is a nucleic acid sequence enabling co-expression of both CCRs

AgB2 is a nucleic acid sequence encoding the antigen-binding domain of the second CCR;

spacer 2 is a nucleic acid sequence encoding the spacer of the second CCR;

TM2 is a a nucleic acid sequence encoding the transmembrane domain of the second CCR;

endo 2 is a nucleic acid sequence encoding the endodomain of the second CCR.

When the nucleic acid construct is expressed in a cell, such as a T-cell, it encodes a polypeptide which is cleaved at the cleavage site such that the first and second CCRs are co-expressed at the cell surface.

The first and second CCRs may bind distinct epitopes on the same antigen.

The first and second CCRs may have complementary endodomains e.g. one derived from the α or β chain of a cytokine receptor and one derived from the γ chain of the same cytokine receptor.

The present invention also provides a nucleic acid construct encoding a CCR of the invention and a CAR. Such a construct may have the structure:

CCRAgB-CCRspacer-CCRTM-CCRendo-coexpr-CARAgB-CARspacer-CARTM-CARendo or

CARAgB-CARspacer-CARTM-CARendo-coexpr-CCRAgB-CCRspacer-CCRTM-CCRendo in which

CCRAgB is a nucleic acid sequence encoding the antigen-binding domain of the CCR;

CCRspacer is a nucleic acid sequence encoding the spacer of the CCR;

CCRTM is a a nucleic acid sequence encoding the transmembrane domain of the CCR;

CCRendo is a nucleic acid sequence encoding the endodomain of the CCR;

coexpr is a nucleic acid sequence enabling co-expression of both the CCR and the CAR CARAgB is a nucleic acid sequence encoding the antigen-binding domain of the CAR;

CARspacer is a nucleic acid sequence encoding the spacer of the CAR;

CARTM is a nucleic acid sequence encoding the transmembrane domain of the CAR; and CARendo is a nucleic acid sequence encoding the endodomain of the CAR.

The present invention also provides a nucleic acid construct encoding a first and a second CCR of the invention and a CAR. The first and second CCRs may bind separate epitopes on the same antigen. Such a construct may have the structure:

(i) CCRAgB1-CCRspacer1-CCRTM1-CCRendo1-coexpr1-CCRAgB2-CCRspacer2-CCRTM2-CCRendo2-coexpr2-CARAgB-CARspacer-CARTM-CARendo;

(ii) CCRAgB1-CCRspacer1-CCRTM1-CCRendo1-coexpr1-CARAgB-CARspacer-CARTM-CARendo-coexpr2-CCRAgB2-CCRspacer2-CCRTM2-CCRendo2; or (iii) CARAgB-CARspacer-CARTM-CARendo-coexpr1-CCRAgB1-CCRspacer1-CCRTM1-CCRendo1-coexpr2-CCRAgB2-CCRspacer2-CCRTM2-CCRendo2;

in which

CCRAgB1 is a nucleic acid sequence encoding the antigen-binding domain of the first CCR;

CCRspacer1 is a nucleic acid sequence encoding the spacer of the first CCR;

CCRTM1 is a nucleic acid sequence encoding the transmembrane domain of the first CCR;

CCRendo1 is a nucleic acid sequence encoding the endodomain of the first CCR;

CCRAgB2 is a nucleic acid sequence encoding the antigen-binding domain of the second CCR;

CCRspacer2 is a nucleic acid sequence encoding the spacer of the second CCR;

CCRTM2 is a nucleic acid sequence encoding the transmembrane domain of the second CCR;

CCRendo2 is a nucleic acid sequence encoding the endodomain of the second CCR;

Coexpr1 and coexpr2 are nucleic acid sequences enabling co-expression of the two flanking sequences;

CARAgB is a nucleic acid sequence encoding the antigen-binding domain of the CAR;

CARspacer is a nucleic acid sequence encoding the spacer of the CAR;

CARTM is a nucleic acid sequence encoding the transmembrane domain of the CAR; and CARendo is a nucleic acid sequence encoding the endodomain of the CAR.

As used herein, the terms "polynucleotide", "nucleotide", and "nucleic acid" are intended to be synonymous with each other.

It will be understood by a skilled person that numerous different polynucleotides and nucleic acids can encode the same polypeptide as a result of the degeneracy of the genetic code. In addition, it is to be understood that skilled persons may, using routine techniques, make nucleotide substitutions that do not affect the polypeptide sequence encoded by the polynucleotides described here to reflect the codon usage of any particular host organism in which the polypeptides are to be expressed.

Nucleic acids according to the invention may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the use as described herein, it is to be understood that the polynucleotides may be modified by any method available in the art. Such modifications may be carried out in order to enhance the in vivo activity or life span of polynucleotides of interest.

The terms "variant", "homologue" or "derivative" in relation to a nucleotide sequence include any substitution of, variation of, modification of, replacement of, deletion of or addition of one (or more) nucleic acid from or to the sequence.

In the structure above, "coexpr" is a nucleic acid sequence enabling co-expression of both first and second CARs. It may be a sequence encoding a cleavage site, such that the nucleic acid construct produces comprises two or more CCRs, or a CCR and a CAR, joined by a cleavage site(s). The cleavage site may be self-cleaving, such that when the polypeptide is produced, it is immediately cleaved into individual peptides without the need for any external cleavage activity.

The cleavage site may be any sequence which enables the first and second CCRs, or CCR and CAR, to become separated.

The term "cleavage" is used herein for convenience, but the cleavage site may cause the peptides to separate into individual entities by a mechanism other than classical cleavage. For example, for the Foot-and-Mouth disease virus (FMDV) 2A self-cleaving peptide (see below), various models have been proposed for to account for the "cleavage" activity: proteolysis by a host-cell proteinase, autoproteolysis or a translational effect (Donnelly et al (2001) J. Gen. Virol. 82:1027-1041). The exact mechanism of such "cleavage" is not important for the purposes of the present invention, as long as the cleavage site, when positioned between nucleic acid sequences which encode proteins, causes the proteins to be expressed as separate entities.

The cleavage site may be a furin cleavage site.

Furin is an enzyme which belongs to the subtilisin-like proprotein convertase family. The members of this family are proprotein convertases that process latent precursor proteins into their biologically active products. Furin is a calcium-dependent serine endoprotease that can efficiently cleave precursor proteins at their paired basic amino acid processing sites. Examples of furin substrates include proparathyroid hormone, transforming growth factor beta 1 precursor, proalbumin, pro-beta-secretase, membrane type-1 matrix metalloproteinase, beta subunit of pro-nerve growth factor and von Willebrand factor. Furin cleaves proteins just downstream of a basic amino acid target sequence (canonically, Arg-X-(Arg/Lys)-Arg') and is enriched in the Golgi apparatus.

The cleavage site may be a Tobacco Etch Virus (TEV) cleavage site.

TEV protease is a highly sequence-specific cysteine protease which is chymotrypsin-like proteases. It is very specific for its target cleavage site and is therefore frequently used for the controlled cleavage of fusion proteins both in vitro and in vivo. The consensus TEV cleavage site is ENLYFQ\S (where '\' denotes the cleaved peptide bond). Mammalian cells, such as human cells, do not express TEV protease. Thus in embodiments in which the present nucleic acid construct comprises a TEV cleavage site and is expressed in a mammalian cell—exogenous TEV protease must also expressed in the mammalian cell.

The cleavage site may encode a self-cleaving peptide.

A 'self-cleaving peptide' refers to a peptide which functions such that when the polypeptide comprising the proteins and the self-cleaving peptide is produced, it is immediately "cleaved" or separated into distinct and discrete first and second polypeptides without the need for any external cleavage activity.

The self-cleaving peptide may be a 2A self-cleaving peptide from an aphtho- or a cardiovirus. The primary 2A/2B cleavage of the aptho- and cardioviruses is mediated by 2A "cleaving" at its own C-terminus. In apthoviruses, such as foot-and-mouth disease viruses (FMDV) and equine rhinitis A virus, the 2A region is a short section of about 18 amino acids, which, together with the N-terminal residue of protein 2B (a conserved proline residue) represents an autonomous element capable of mediating "cleavage" at its own C-terminus (Donelly et al (2001) as above).

"2A-like" sequences have been found in picornaviruses other than aptho- or cardioviruses, 'picornavirus-like' insect viruses, type C rotaviruses and repeated sequences within Trypanosoma spp and a bacterial sequence (Donnelly et al (2001) as above). The cleavage site may comprise one of these 2A-like sequences, such as:

```
                                        (SEQ ID No. 33)
YHADYYKQRLIHDVEMNPGP (SEQ ID No. 34)
HYAGYFADLLIHDIETNPGP (SEQ ID No. 35)
QCTNYALLKLAGDVESNPGP (SEQ ID No. 36)
ATNFSLLKQAGDVEENPGP (SEQ ID No. 37)
AARQMLLLLSGDVETNPGP (SEQ ID No. 38)
RAEGRGSLLTCGDVEENPGP (SEQ ID No. 39)
TRAEIEDELIRAGIESNPGP (SEQ ID No. 40)
TRAEIEDELIRADIESNPGP (SEQ ID No. 41)
AKFQIDKILISGDVELNPGP (SEQ ID No. 42)
SSIIRTKMLVSGDVEENPGP (SEQ ID No. 43)
CDAQRQKLLLSGDIEQNPGP (SEQ ID No. 44)
YPIDFGGFLVKADSEFNPGP
```

The cleavage site may comprise the 2A-like sequence shown as SEQ ID No. 38 (RAEGRGSLLTCGDVEENPGP).

The present invention also provides a kit comprising one or more nucleic acid sequence(s) encoding first and second CCRs according to the first aspect of the present invention, or one or more CCR(s) according to the invention and one or more CAR(s).

SEQ ID NOS 45 and 46 give the complete amino acid sequences of a fusion between and anti-PSMA CAR and an anti-PSA CCR. Subheadings are given to label each portion of the sequence but in practice the various elements are connected giving one continuous sequence.

The nucleic acid construct of the invention may encode a fusion protein as shown in SEQ ID No. 45 or 46.

```
-Illustrative construct with IL-2R beta chain
                                         SEQ ID NO. 45

Signal sequence derived from human CD8a:
MSLPVTALLLPLALLLHAA scFv aPSMA (J591 H/L)
EVQLQQSGPELKKPGTSVRISCKTSGYTFTEYTIHWVKQSHGKSLEWIGN

INPNGTTYNQKFEDKATLTVDKSSSTAYMELRSLTSEDSAVYYCAAGWNF

DYWGQGTTVSSGGGGSGGGGSGGGGSDIVMTQSHKFMSTSVGDRVSIICK

ASQDVGTAVYQQKPGQSPKWYWASTRHTGVPDRFTGSGSGTDFTLTITNV

QSEDLADYFCQNSYPLTFGAGTMLDLKR

Linker
SDPA

Human IgG1 Fc spacer (HCH2CH3pvaa):
EPKSPDKTHTCPPCPAPPVAGPSVFLFPPKPKDTLMIARTPEVTCVVVDV

SHEDPKFNWYVDGVEVHNAKTKPREEQYNSTYRVVSVLTVLHQDWLNGKE
```

-continued
YKCKVSNKPAPIEKTISKAKGQPREPQVYTLPPSRDELTKNQVSLTCLVK

GFYPSDIAVEWESQPENNYKTTPPVLDSDGSFFLYSKLTVDKSRWQQGNV

FSCSVMHEALHNHYTQLSLSPGK

Transmembrane derived from human CD28:
FWVLVVVGGVLACYSLLVTVAFIIFWV

Endodomain derived from TCRz:
RRVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATKD
TYDALHMQALPPR 2A peptide from Thosea asigna virus capsid protein:
RAEGRGSLLTCGDVEENPGP Signal sequence derived from mouse kappa VIII:
METDTLILWVLLLLVPGSTG scFv aPSA (5D5A5 H/L):
QVQLQQSGAELAKPGASVKMSCKTSGYSFSSYVVMHWVKQRPGQGLEWIG

YINPSTGYTENNQKFKDKVTLTADKSSNTAYMQLNSLTSEDSAVYYCARS

GRLYFDVWGAGTTVTVSSGGGGSGGGGSGGGGSGGGGSDIVLTQSPPSLA

VSLGQRATISCRASESIDLYGFTFMHWYQQKPGQPPKILIYRASNLESGI

PARFSGSGSRTDFTLTINPVEADDVATYYCQQTHEDPYTFGGGTKLEIK

Linker:
SDPA

Human CD8aSTK spacer:
TTTPAPRPPTPAPTIASQPLSLRPEACRPAAGGAVHTRGLDFACDI

Transmembrane derived from human common gamma chain:
VVISVGSMGLIISLLCVYFWL

Endodomain derived from human common gamma chain:
ERTMPRIPTLKNLEDLVTEYHGNFSAWSGVSKGLAESLQPDYSERLCLVS
EIPPKGGALGEGPGASPCNQHSPYWAPPCYTLKPET 2A peptide from equine rhinitis A virus polyprotein:
QCTNYALLKLAGDVESNPGP Signal sequence derived from mouse kappa VIII:
METDTLILWVLLLLVPGSTG scFv aPSA (5D3D11 H/L):
QVQLQQSGPELVKPGASVKISCKVSGYAISSSWMNWVKQRPGQGLEWIGR

IYPGDGDTKYNGKFKDKATLTVDKSSSTAYMQLSSLTSVDSAVYFCARDG

YRYYFDYWGQGTSVTVSSGGGGSGGGGSGGGGSGGGGSDIVMTQTAPSVF

VTPGESVSISCRSSKSLLHSNGNTYLYWFLQRPGQSPQLLIYRMSNLASG

VPDRFSGSGSGTDFTLRISRVEAEDVGVYYCMQHLEYPVTFGAGTKVEIK

Linker:
SDPA

Human CD28STK spacer:
KIEVMYPPPYLDNEKSNGTIIHVKGKHLCPSPLFPGPSKP

Transmembrane derived from human IL-2Rβ:
IPWLGHLLVGLSGAFGFIILVYLLI

Endodomain derived from human IL-2Rβ:
NCRNTGPWLKKVLKCNTPDPSKFFSQLSSEHGGDVQKWLSSPFPSSSFSP

GGLAPEISPLEVLERDKVTQLLLQQDKVPEPASLSSNHSLTSCFTNQGYF

FFHLPDALEIEACQVYFTYDPYSEEDPDEGVAGAPTGSSPQPLQPLSGED

DAYCTFPSRDDLLLFSPSLLGGPSPPSTAPGGSGAGEERMPPSLQERVPR

-continued
DWDPQPLGPPTPGVPDLVDFQPPPELVLREAGEEVPDAGPREGVSFPWSR

PPGQGEFRALNARLPLNTDAYLSLQELQGQDPTHLV

-Illustrative construct with IL-7R alpha chain
SEQ ID No. 46

Signal sequence derived from human CD8a:
MSLPVTALLLPLALLLHAA scFv aPSMA (J591 H/L)
EVQLQQSGPELKKPGTSVRISCKTSGYTFTEYTIHWVKQSHGKSLEWIGN

INPNNGGTTYNQKFEDKATLTVDKSSSTAYMELRSLTSEDSAVYYCAAGW

NFDYWGQGTTLTVSSGGGGSGGGGSGGGGSDIVMTQSHKFMSTSVGDRVS

IICKASQDVGTAVDWYQQKPGQSPKWYWASTRHTGVPDRFTGSGSGTDFT

LTITNVQSEDLADYFCQQYNSYPLTFGAGTMLDLKR

Linker
SDPA

Human IgG1 Fc spacer (HCH2CH3pvaa):
EPKSPDKTHTCPPCPAPPVAGPSVFLFPPKPKDTLMIARTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK

Transmembrane derived from human CD28:
FWVLWVGGVLACYSLLVTVAFIIFWV

Endodomain derived from TCRz:
RRVKFSRSADAPAYQQGQNQLYNELNLGRREEYDVLDKRRGRDPEMGGKP
RRKNPQEGLYNELQKDKMAEAYSEIGMKGERRRGKGHDGLYQGLSTATKD
TYDALHMQALPPR 2A peptide from Thosea asigna virus capsid protein:
RAEGRGSLLTCGDVEENPGP Signal sequence derived from mouse kappa VIII:
METDTLILWVLLLLVPGSTG scFv aPSA (5D5A5 H/L):
QVQLQQSGAELAKPGASVKMSCKTSGYSFSSYVVMHWVKQRPGQGLEWIG

YINPSTGYTENNQKFKDKVTLTADKSSNTAYMQLNSLTSEDSAVYYCARS

GRLYFDVWGAGTTVTVSSGGGGSGGGGSGGGGSGGGGSDIVLTQSPPSLA

VSLGQRATISCRASESIDLYGFTFMHWYQQKPGQPPKILIYRASNLESGI

PARFSGSGSRTDFTLTINPVEADDVATYYCQQTHEDPYTFGGGTKLEIK

Linker:
SDPA

Human CD8aSTK spacer:
TTTPAPRPPTPAPTIASQPLSLRPEACRPAAGGAVHTRGLDFACDI

Transmembrane derived from human common gamma chain:
VVISVGSMGLIISLLCVYFWL

Endodomain derived from human common gamma chain:
ERTMPRIPTLKNLEDLVTEYHGNFSAWSGVSKGLAESLQPDYSERLCLV
SEIPPKGGALGEGPGASPCNQHSPYWAPPCYTLKPET 2A peptide from equine rhinitis A virus polyprotein:
QCTNYALLKLAGDVESNPGP -continued

```
Signal sequence derived from mouse kappa VIII:
METDTLILWVLLLLVPGSTG scFv aPSA (5D3D11 H/L):
QVQLQQSGPELVKPGASVKISCKVSGYAISSSWMNWVKQRPGQGLEWIG

RIYPGDGDTKYNGKFKDKATLTVDKSSSTAYMQLSSLTSVDSAVYFCAR

DGYRYYFDYWGQGTSVTVSSGGGGSGGGGSGGGGSGGGGSDIVMTQTAP

SVFVTPGESVSISCRSSKSLLHSNGNTYLYWFLQRPGQSPQLLIYRMSN

LASGVPDRFSGSGSGTDFTLRISRVEAEDVGVYYCMQHLEYPVTFGAG

TKVEIK

Linker:
SDPA

Human CD28STK spacer:
KIEVMYPPPYLDNEKSNGTIIHVKGKHLCPSPLFPGPSKP

Transmembrane derived from human IL-7Ra:
PILLTISILSFFSVALLVILACVLW

Endodomain derived from human IL-7Ra:
KKRIKPIVWPSLPDHKKTLEHLCKKPRKNLNVSFNPESFLDCQIHRVDDI

QARDEVEGFLQDTFPQQLEESEKQRLGGDVQSPNCPSEDVVITPESFGRD

SSLTCLAGNVSACDAPILSSSRSLDCRESGKNGPHVYQDLLLSLGTTNST

LPPPFSLQSGILTLNPVAQGQPILTSLGSNQEEAYVTMSSFYQNQ
```

Vector

The present invention also provides a vector, or kit of vectors, which comprises one or more nucleic acid sequence(s) encoding a one or more CCR(s) according to the first aspect of the invention and optionally one or more CAR(s). Such a vector may be used to introduce the nucleic acid sequence(s) into a host cell so that it expresses a CCR according to the first aspect of the invention.

The vector may, for example, be a plasmid or a viral vector, such as a retroviral vector or a lentiviral vector, or a transposon based vector or synthetic mRNA.

The vector may be capable of transfecting or transducing a T cell or a NK cell.

Cell

The present invention provides a cell which comprises one or more CCR(s) of the invention and optionally one of more CAR(s).

The cell may comprise a nucleic acid or a vector of the present invention.

The cell may be a cytolytic immune cell such as a T cell or an NK cell.

T cells or T lymphocytes are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses.

Cytolytic T cells (TC cells, or CTLs) destroy virally infected cells and tumor cells, and are also implicated in transplant rejection. CTLs express the CD8 at their surface. These cells recognize their targets by binding to antigen associated with MHC class I, which is present on the surface of all nucleated cells. Through IL-10, adenosine and other molecules secreted by regulatory T cells, the CD8+ cells can be inactivated to an anergic state, which prevent autoimmune diseases such as experimental autoimmune encephalomyelitis.

Memory T cells are a subset of antigen-specific T cells that persist long-term after an infection has resolved. They quickly expand to large numbers of effector T cells upon re-exposure to their cognate antigen, thus providing the immune system with "memory" against past infections. Memory T cells comprise three subtypes: central memory T cells (TCM cells) and two types of effector memory T cells (TEM cells and TEMRA cells). Memory cells may be either CD4+ or CD8+. Memory T cells typically express the cell surface protein CD45RO.

Regulatory T cells (Treg cells), formerly known as suppressor T cells, are crucial for the maintenance of immunological tolerance. Their major role is to shut down T cell-mediated immunity toward the end of an immune reaction and to suppress auto-reactive T cells that escaped the process of negative selection in the thymus.

Two major classes of CD4+ Treg cells have been described—naturally occurring Treg cells and adaptive Treg cells.

Naturally occurring Treg cells (also known as CD4+ CD25+FoxP3+ Treg cells) arise in the thymus and have been linked to interactions between developing T cells with both myeloid (CD11c+) and plasmacytoid (CD123+) dendritic cells that have been activated with TSLP. Naturally occurring Treg cells can be distinguished from other T cells by the presence of an intracellular molecule called FoxP3. Mutations of the FOXP3 gene can prevent regulatory T cell development, causing the fatal autoimmune disease IPEX.

Adaptive Treg cells (also known as Tr1 cells or Th3 cells) may originate during a normal immune response.

The cell may be a Natural Killer cell (or NK cell). NK cells form part of the innate immune system. NK cells provide rapid responses to innate signals from virally infected cells in an MHC independent manner NK cells (belonging to the group of innate lymphoid cells) are defined as large granular lymphocytes (LGL) and constitute the third kind of cells differentiated from the common lymphoid progenitor generating B and T lymphocytes. NK cells are known to differentiate and mature in the bone marrow, lymph node, spleen, tonsils and thymus where they then enter into the circulation.

The CCR-expressing cells of the invention may be any of the cell types mentioned above.

T or NK cells according to the first aspect of the invention may either be created ex vivo either from a patient's own peripheral blood (1st party), or in the setting of a haematopoietic stem cell transplant from donor peripheral blood (2nd party), or peripheral blood from an unconnected donor (3rd party).

Alternatively, T or NK cells according to the first aspect of the invention may be derived from ex vivo differentiation of inducible progenitor cells or embryonic progenitor cells to T or NK cells. Alternatively, an immortalized T-cell line which retains its lytic function and could act as a therapeutic may be used.

In all these embodiments, CCR-expressing cells are generated by introducing DNA or RNA coding for the or each CCR(s) by one of many means including transduction with a viral vector, transfection with DNA or RNA.

The cell of the invention may be an ex vivo T or NK cell from a subject. The T or NK cell may be from a peripheral blood mononuclear cell (PBMC) sample. T or NK cells may be activated and/or expanded prior to being transduced with nucleic acid encoding the molecules providing the CCR according to the first aspect of the invention, for example by treatment with an anti-CD3 monoclonal antibody.

The T or NK cell of the invention may be made by:
(i) isolation of a T or NK cell-containing sample from a subject or other sources listed above; and
(ii) transduction or transfection of the T or NK cells with one or more a nucleic acid sequence(s) encoding a CCR.

The T or NK cells may then by purified, for example, selected on the basis of expression of the antigen-binding domain of the antigen-binding polypeptide.

Pharmaceutical Composition

The present invention also relates to a pharmaceutical composition containing a plurality of cells according to the invention.

The pharmaceutical composition may additionally comprise a pharmaceutically acceptable carrier, diluent or excipient. The pharmaceutical composition may optionally comprise one or more further pharmaceutically active polypeptides and/or compounds. Such a formulation may, for example, be in a form suitable for intravenous infusion.

Method of Treatment

The present invention provides a method for treating and/or preventing a disease which comprises the step of administering the cells of the present invention (for example in a pharmaceutical composition as described above) to a subject.

A method for treating a disease relates to the therapeutic use of the cells of the present invention. Herein the cells may be administered to a subject having an existing disease or condition in order to lessen, reduce or improve at least one symptom associated with the disease and/or to slow down, reduce or block the progression of the disease.

The method for preventing a disease relates to the prophylactic use of the cells of the present invention. Herein such cells may be administered to a subject who has not yet contracted the disease and/or who is not showing any symptoms of the disease to prevent or impair the cause of the disease or to reduce or prevent development of at least one symptom associated with the disease. The subject may have a predisposition for, or be thought to be at risk of developing, the disease.

The method may involve the steps of:
(i) isolating a T or NK cell-containing sample;
(ii) transducing or transfecting such cells with a nucleic acid sequence or vector provided by the present invention;
(iii) administering the cells from (ii) to a subject.

The T or NK cell-containing sample may be isolated from a subject or from other sources, for example as described above. The T or NK cells may be isolated from a subject's own peripheral blood (1st party), or in the setting of a haematopoietic stem cell transplant from donor peripheral blood (2nd party), or peripheral blood from an unconnected donor (3rd party).

The present invention provides a CCR-expressing cell of the present invention for use in treating and/or preventing a disease.

The invention also relates to the use of a CCR-expressing cell of the present invention in the manufacture of a medicament for the treatment and/or prevention of a disease.

The disease to be treated and/or prevented by the methods of the present invention may be a cancerous disease, such as bladder cancer, breast cancer, colon cancer, endometrial cancer, kidney cancer (renal cell), leukaemia, lung cancer, melanoma, non-Hodgkin lymphoma, pancreatic cancer, prostate cancer and thyroid cancer.

Where the ligand recognised by the CCR is PSA, the cancer may be prostate cancer.

The cells of the present invention may be capable of killing target cells, such as cancer cells. The target cell may be characterised by the presence of a tumour secreted ligand or chemokine ligand in the vicinity of the target cell. The target cell may be characterised by the presence of a soluble ligand together with the expression of a tumour-associated antigen (TAA) at the target cell surface.

The cells and pharmaceutical compositions of present invention may be for use in the treatment and/or prevention of the diseases described above.

The cells and pharmaceutical compositions of present invention may be for use in any of the methods described above.

Chimeric Transmembrane Protein

The present invention also provides a chimeric transmembrane protein comprising a dimerization domain; and a cytokine receptor endodomain.

Dimerisation may occur spontaneously, in which case the chimeric transmembrane protein will be constitutively active. Alternatively, dimerization may occur only in the presence of a chemical inducer of dimerization (CID) in which case the transmembrane protein only causes cytokine-type signalling in the presence of the CID.

Suitable dimerization domains and CIDs are described in WO2015/150771, the contents of which are hereby incorporated by reference.

For example, one dimerization domain may comprise the rapamycin binding domain of FK-binding protein 12 (FKBP12), the other may comprise the FKBP12-Rapamycin Binding (FRB) domain of mTOR; and the CID may be rapamycin or a derivative thereof.

One dimerization domain may comprise the FK506 (Tacrolimus) binding domain of FK-binding protein 12 (FKBP12) and the other dimerization domain may comprise the cyclosporin binding domain of cylcophilin A; and the CID may be an FK506/cyclosporin fusion or a derivative thereof.

One dimerization domain may comprise an oestrogen-binding domain (EBD) and the other dimerization domain may comprise a streptavidin binding domain; and the CID may be an estrone/biotin fusion protein or a derivative thereof.

One dimerization domain may comprise a glucocorticoid-binding domain (GBD) and the other dimerization domain may comprise a dihydrofolate reductase (DHFR) binding domain; and the CID may be a dexamethasone/methotrexate fusion protein or a derivative thereof.

One dimerization domain may comprise an 06-alkylguanine-DNA alkyltransferase (AGT) binding domain and the other dimerization domain may comprise a dihydrofolate reductase (DHFR) binding domain; and the CID may be an 06-benzylguanine derivative/methotrexate fusion protein or a derivative thereof.

One dimerization domain may comprise a retinoic acid receptor domain and the other dimerization domain may comprise an ecodysone receptor domain; and the CID may be RSL1 or a derivative thereof.

Where the dimerization domain spontaneously heterodimerizes, it may be based on the dimerization domain of an antibody. In particular it may comprise the dimerization portion of a heavy chain constant domain (CH) and a light chain constant domain (CL). The "dimerization portion" of a constant domain is the part of the sequence which forms the inter-chain disulphide bond.

The chimeric cytokine receptor may comprise the Fab portion of an antibody as exodomain, for example as illustrated schematically in FIG. 5.

The chimeric transmembrane protein may comprise two polypeptides:
(i) a first polypeptide which comprises:
(a) a first dimerisation domain; and
(b) a first chain of the cytokine receptor endodomain; and
(ii) a second polypeptide which comprises:
(a) a second dimerization domain, which dimerises with the first dimerization domain; and
(b) a second chain of the cytokine-receptor endodomain.

The sections above defining the cytokine receptor endodomain of the chimeric cytokine receptor also apply to the chimeric transmembrane protein of the present invention.

The sections above relating to nucleic acids, vectors, kits, cells, pharmaceutical compositions and methods also apply to the chimeric transmembrane protein of the present invention.

The invention will now be further described by way of Examples, which are meant to serve to assist one of ordinary skill in the art in carrying out the invention and are not intended in any way to limit the scope of the invention.

EXAMPLES

Example 1—In Vitro Testing

T-cells are transduced with either a PSMA-specific CAR, or transduced with a construct which co-expresses a PSMA-specific CAR with a PSA-specific CCR. T-cells are co-cultured with PSMA expressing target cells which secrete or do not secrete PSA. This co-culture is conducted in the presence or absence of exogenous IL2. This co-culture is conducted at different effector to target ratios. This co-culture is repeated serially with T-cells challenged with repeated target cells. Proliferation of T-cells and killing of target cells is determined. In this way, the contribution to proliferation and survival of T-cells the CCR makes can be measured. Further, the ability contribution to repeated re-challenge the ability of serial Example 2—In Vivo Testing NSG mice are engrafted with a human prostate cancer cell line which expresses PSMA and secretes PSA and which expresses firefly Luciferase. T-cells are transduced with either a PSMA-specific CAR, or transduced with a construct which co-expresses the PSMA-specific CAR with a PSA-specific CCR. T-cells are administered to the mice. The tumour burden can be serially measured using bioluminescent imaging and the response to CAR T-cells evaluated. Mice within each cohort can be sacrificed at different time-points and tumour burden directly measured by macroscopic measurements and by immunohistochemistry. Further, engraftment/expansion of T-cells at the tumour bed or within lymphoid tissues such as lymph nodes, spleen and bone-marrow measured by flow cytometry of said tissues.

Example 3—Creation of and Testing a Constitutively Active Cytokine-Signalling Molecule A constitutively active cytokine-signalling chimeric transmembrane protein was produced by linking cytokine receptor endodomains to a "Fab" type exodomain (FIG. 5). This structure uses the natural dimerization components of antibodies, namely the dimerization domain from the heavy and light chain constant regions. The chimeric transmembrane protein has two chains; a first polypeptide which comprises the antibody light κ chain and the IL2 receptor common γ chain as endodomain; and a second polypeptide which comprises the antibody heavy chain CH1 and an endodomain which comprises either: the IL2 receptor β chain (giving a constitutively active IL2-signalling molecule); or the IL7 receptor (giving a constitutively active IL7-signalling molecule). The constitutively active cytokine-signalling chimeric transmembrane proteins tested in this study included the scFv heavy and light chain variable regions. These domains are not needed for dimerization to occur. The signal is independent of antigen binding and the structure could equally be "headless" (as shown in FIG. 5) or comprise another entity such as a protein tag.

Nucleic acid sequences encoding these two polypeptides were cloned in frame separated by a 2A-peptide encoding sequence.

CTLL-2 (ATCC® TIB-214™) are murine cytotoxic T lymphocyte cells which are dependent upon IL-2 for growth. In the absence of IL-2 the cells undergo apoptosis. CTLL-2 cells were transduced with a vector expressing the chimeric protein comprising an IL2-receptor endodomain (Fab_IL2endo) or a vector expressing the chimeric protein comprising an IL7 receptor endodomain (Fab_IL7endo) or left untransduced (WT). As a positive control, cells of all three types were co-cultured with 100 U/ml murine IL2. Cell proliferation was assessed after 3 and 7 days of culture and the results are shown in FIG. 6.

Untransduced CTLL2 cells, together with CTLL2 cells transduced with either construct (Fab_IL2endo or Fab_IL7endo) proliferated in the presence of 100 U/mL murine IL2 (FIG. 6, left-hand panel). However, in the absence of exogenously added IL2, only cells transduced with the construct having an IL2R endodomain (Fab_IL2endo) survived and proliferated. This shows that the chimeric transmembrane receptor provides the CTLL2 cells with the necessary IL2 signal.

Example 4—Generation and Testing of a Chimeric Cytokine Receptor Against PSA

A panel of chimeric cytokine receptors targeting PSA was developed using scFvs derived from two antibodies which bind to different PSA epitopes: 5D5A5 and 5D3D11. The crystal structure of PSA has been obtained in a sandwich complex with these two (Stura et al (2011) as above).

Schematic diagrams illustrating some of the panel of CCRs is illustrated in FIG. 7.

The panel included the following constructs:

A5-CD8stk-IL2Rg_D11-Hinge-IL2Rb: A CCR with an IL-2R endodomain having A5 on the chain with common γ chain and D11 on the chain with the IL2R β chain;

D11-CD8stk-IL2Rg_A5-Hinge-IL2Rb: A CCR with an IL-2R endodomain having D11 on the chain with common γ chain and A5 on the chain with IL2R β chain;

D11-CD8stk-RL_A5-Hinge-IL2Rb: A negative control construct which is equivalent D11-CD8stk-IL2Rg_A5-Hinge-IL2Rb, but in which the IL2Rγ chain is replaced by a rigid linker;

D11-CD8stk-IL2Rg_A5-Hinge-IL7Ra: A CCR with an IL-7R endodomain having D11 on the chain with common γ chain and A5 on the chain with IL7R α chain; and D11-CD8stk-RL_A5-Hinge-IL7Ra: A negative control construct which is equivalent D11-CD8stk-IL2Rg_A5-Hinge-IL7Ra, but in which the IL2Rγ chain is replaced by a rigid linker;

CTLL2 cells were transduced with vectors expressing these constructs. Cells were cultured in the presence or absence of IL2 (the presence of IL2 acting as a positive control) and the presence or absence of 5 ng/mL or 5 μg/mL PSA. CTLL2 cell proliferation was assessed after 3 and 7 days and the results are shown in FIG. 8.

CTLL2 cells expressing a CCR with an IL7 endodomain did not support CTLL2 cell survival and proliferation (FIG. 8, last two panels). The presence of murine IL-2 in these cells supported CTLL2 cell growth and proliferation at day 3, but by day 7 the majority of cells had undergone apoptosis.

The anti-PSA chimeric cytokine receptors with an IL2R endodomain supported CTLL2 cell proliferation in the absence of IL2 and the presence of PSA at both 5 ng/ml and 5 μg/ml (FIG. 8, first panel), with 5 μg/ml giving greater survival and proliferation, particularly at day 7.

Both the anti-PSA chimeric cytokine receptors with an IL2R endodomain, i.e. A5-CD8stk-IL2Rg_D11-Hinge-IL2Rb and D11-CD8stk-IL2Rg_A5-Hinge-IL2Rb, indicating that the relative positioning of the two PSA-binding domains: 5D5A5 and 5D3D11, is not important for function.

Substitution of the common γ chain with a rigid linker abolished the capacity of the CCR to support CTLL2 cell survival and proliferation (FIG. 8, third panel).

As another read-out for IL2 signalling, the phosphorylation of Y694 of STAT5 was investigated using phospho-flow.

CTLL2 cells were either untransduced (WT); transduced with a PSA CCR constructs having an IL2R endodomain (D11-CD8STK-IL2Rg_A5-Hinge-IL2Rb); or transduced with an equivalent negative control construct in which the IL2Rγ chain is replaced with a rigid linker (D11-CD8STK-RL_A5-Hinge-IL2Rb). The cells were incubated overnight in the absence of exogenously added IL-2. The following day, the cells were incubated with either Pervanadate at 500 μM (a positive control which inhibits phosphatase and will lead to STAT5 phoshorylation) or 500 ng/mL PSA for 1 or 4 hours. After incubation the cells were fixed, permeabilised and analysed by flow cytometry.

The results are shown in FIG. 9. In the cells expressing the PSA CCR, the presence of PSA lead to increasing STAT5 phosphorylation with time (FIG. 9, central panel). No such increase in phosphorylation was seen with untransduced CTLL2 cells, or with CTLL2 cells transduced with an equivalent construct in which the IL2Rγ chain is replaced with a rigid linker (FIG. 9, right hand panel).

These results are consistent with the CTLL2 survival/proliferation data shown in FIG. 8 and demonstrate that a chimeric cytokine receptor against a soluble ligand (here, PSA) can be used to trigger cytokine signalling in a T-cell.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A chimeric cytokine receptor (CCR) comprising a first and a second chimeric transmembrane polypeptides, wherein:
   (i) the first chimeric transmembrane polypeptide comprises:
      (a) a first exodomain which comprises an antigen-binding domain of an antibody which binds a first epitope of a ligand;
      (b) a first transmembrane domain; and
      (c) a first cytokine receptor endodomain; and
   (ii) the second chimeric transmembrane polypeptide comprises:
      (a) a second exodomain which comprises an antigen-binding domain of an antibody which binds a second epitope of the ligand;
      (b) a second transmembrane domain; and
      (c) a second cytokine receptor endodomain;
wherein the ligand is a tumour secreted factor; and wherein the first cytokine receptor endodomain or the second cytokine receptor endodomain is an IL-2 receptor β-chain endodomain, an IL-7 receptor α-chain endodomain, or an IL-15 receptor α-chain endodomain; and wherein the other cytokine receptor endodomain is a γ-chain receptor endodomain of an IL-2 receptor, an IL-7 receptor, or an IL-15 receptor.

2. A chimeric cytokine receptor (CCR) comprising a first and a second chimeric transmembrane polypeptides, wherein:
(i) the first chimeric transmembrane polypeptide comprises:
(a) a first exodomain which comprises a heavy chain variable domain ($V_H$) of an antibody that binds to the ligand;
(b) a first transmembrane domain; and
(c) a first cytokine receptor endodomain; and
(ii) the second chimeric transmembrane polypeptide comprises:
(a) a second exodomain which comprises a light chain variable domain ($V_L$) of the antibody that binds to the ligand;
(b) a second transmembrane domain; and
(c) a second cytokine-receptor endodomain;
wherein the ligand is a tumour secreted factor; and
wherein the first cytokine receptor endodomain or the second cytokine receptor endodomain is an IL-2 receptor β-chain endodomain, an IL-7 receptor α-chain endodomain, or an IL-15 receptor α-chain endodomain; and wherein the other cytokine receptor endodomain is a γ-chain receptor endodomain of an IL-2 receptor, an IL-7 receptor, or an IL-15 receptor.

3. A chimeric cytokine receptor according to claim 1, wherein the ligand is a tumour secreted factor selected from: prostate-specific antigen (PSA), carcinoembryonic antigen (CEA), vascular endothelial growth factor (VEGF), and CA125.

4. The CCR according to claim 1, wherein the antigen-binding domains of the first exodomain and the second exodomain each comprises a single-chain variable fragment (scFv) that binds to the ligand.

5. The CCR according to claim 1, wherein the antigen-binding domains of the first exodomain and the second exodomain each comprise a single-chain variable fragment (scFv) which bind to different prostate-specific antigen (PSA) epitopes.

6. The CCR according to claim 2, wherein the first exodomain comprises a VH of an antibody that binds to PSA; and wherein the second exodomain which comprises a VL of the antibody that binds to PSA.

7. The CCR according to claim 1,
wherein the first chimeric transmembrane polypeptide further comprises a first spacer connecting the first exodomain and the first transmembrane domain; and
wherein the second chimeric transmembrane polypeptide further comprises a second spacer connecting the second exodomain and the second transmembrane domain.

8. The CCR according to claim 7, wherein the first spacer comprises an IgG1 Fc region, an IgG1 hinge, or a CD8 stalk; and wherein the second spacer comprises an IgG1 Fc region, an IgG1 hinge, or a CD8 stalk.

9. The CCR according to claim 2,
wherein the first chimeric transmembrane polypeptide further comprises a first spacer connecting the first exodomain and the first transmembrane domain; and
wherein the second chimeric transmembrane polypeptide further comprises a second spacer connecting the second exodomain and the second transmembrane domain.

10. The CCR according to claim 9, wherein the first spacer comprises an IgG1 Fc region, an IgG1 hinge, or a CD8 stalk; and wherein the second spacer comprises an IgG1 Fc region, an IgG1 hinge, or a CD8 stalk.

11. A chimeric cytokine receptor according to claim 2, wherein the ligand is a tumour secreted factor selected from: prostate-specific antigen (PSA), carcinoembryonic antigen (CEA), vascular endothelial growth factor (VEGF), and CA125.

12. A nucleic acid construct which encodes a CCR according to claim 1, the nucleic acid construct comprising a first nucleic acid sequence encoding the first chimeric transmembrane polypeptide and a second nucleic acid sequence encoding the second chimeric transmembrane polypeptide, the nucleic acid construct having the structure:
AgB1-spacer1-TM1-endo1-coexpr-AbB2-spacer2-TM2-endo2
in which
AgB1 is a nucleic acid sequence encoding the first exodomain which comprises the first antigen-binding domain;
spacer1 is a nucleic acid sequence encoding a spacer between the first exodomain and the first transmembrane domain;
TM1 is a nucleic acid sequence encoding the first transmembrane domain;
endo1 is a nucleic acid sequence encoding the first cytokine receptor endodomain;
coexpr is a nucleic acid sequence enabling co-expression of the first chimeric transmembrane polypeptide and the second chimeric transmembrane polypeptide;
AgB2 is a nucleic acid sequence encoding the second exodomain which comprises the second antigen-binding domain;
spacer2 is a nucleic acid sequence encoding a spacer between the second exodomain and the second transmembrane domain;
TM2 is a nucleic acid sequence encoding the second transmembrane domain;
endo2 is a nucleic acid sequence encoding the second cytokine receptor endodomain.

13. A vector comprising a nucleic acid construct according to claim 12.

14. A method for making a cell which comprises a chimeric cytokine receptor, the method comprising introducing into an isolated cell: the nucleic acid construct of claim 12 or a vector comprising said nucleic acid construct.

15. An isolated cell which comprises a chimeric cytokine receptor according to claim 1.

16. An isolated cell which comprises a chimeric cytokine receptor according to claim 2.

17. An isolated cell according to claim 15, which also comprises a chimeric antigen receptor.

18. A pharmaceutical composition comprising a plurality of cells according to claim 15.

19. A pharmaceutical composition comprising a plurality of cells according to claim 16.

20. A kit which comprises:
i) a vector comprising a nucleic acid sequence encoding the first chimeric transmembrane polypeptide of claim 1; and
ii) a vector comprising a nucleic acid sequence encoding the second chimeric transmembrane polypeptide according to claim 1.

21. A kit according to claim 20 which also comprises a vector comprising a nucleic acid sequence encoding a chimeric antigen receptor.

22. A kit comprising the vector according to claim 13 and a vector comprising a nucleic acid sequence encoding a chimeric antigen receptor.

* * * * *

UNITED STATES PATENT AND TRADEMARK OFFICE
CERTIFICATE OF CORRECTION

PATENT NO.          : 10,800,854 B2                                      Page 1 of 1
APPLICATION NO.     : 15/753486
DATED               : October 13, 2020
INVENTOR(S)         : Martin Pulé et al.

It is certified that error appears in the above-identified patent and that said Letters Patent is hereby corrected as shown below:

In the Claims

At Column 95, Line 58, "polypeptides," should be -- polypeptide, --.

At Column 97, Line 5, "polypeptides," should be -- polypeptide, --.

At Column 97, Line 45, "VH" should be -- $V_H$ --.

At Column 97, Line 47, "VL" should be -- $V_L$ --.

At Column 98, Line 15, "AbB2" should be -- AgB2 --.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 55

<210> SEQ ID NO 1
<211> LENGTH: 86
<212> TYPE: PRT
<213> ORGANISM: Artificial Sequence
<220> FEATURE:
<223> OTHER INFORMATION: endodomain derived from IL-2 receptor common
      gamma-chain

<400> SEQUENCE: 1

Glu Arg Thr Met Pro Arg Ile Pro Thr Leu Lys Asn Leu Glu Asp Leu
1               5                   10                  15

Val Thr Glu Tyr His Gly Asn Phe Ser Ala Trp Ser Gly Val Ser Lys
            20                  25                  30

Gly Leu Ala Glu Ser Leu Gln Pro Asp Tyr Ser Glu Arg Leu Cys Leu
        35                  40                  45

Val Ser Glu Ile Pro Pro Lys Gly Gly Ala Leu Gly Glu Gly Pro Gly
    50                  55                  60

Ala Ser Pro Cys Asn Gln His Ser Pro Tyr Trp Ala Pro Pro Cys Tyr
65                  70                  75                  80

Thr Leu Lys Pro Glu Thr
```

<210> SEQ ID NO 2
<211> LENGTH: 286
<212> TYPE: PRT
<213> ORGANISM: Artificial Sequence
<220> FEATURE:
<223> OTHER INFORMATION: endodomain derived from IL-2 receptor common beta-chain

<400> SEQUENCE: 2

```
Asn Cys Arg Asn Thr Gly Pro Trp Leu Lys Lys Val Leu Lys Cys Asn
1               5                   10                  15
Thr Pro Asp Pro Ser Lys Phe Phe Ser Gln Leu Ser Ser Glu His Gly
            20                  25                  30
Gly Asp Val Gln Lys Trp Leu Ser Ser Pro Phe Pro Ser Ser Ser Phe
        35                  40                  45
Ser Pro Gly Gly Leu Ala Pro Glu Ile Ser Pro Leu Glu Val Leu Glu
    50                  55                  60
Arg Asp Lys Val Thr Gln Leu Leu Leu Gln Gln Asp Lys Val Pro Glu
65                  70                  75                  80
Pro Ala Ser Leu Ser Ser Asn His Ser Leu Thr Ser Cys Phe Thr Asn
                85                  90                  95
Gln Gly Tyr Phe Phe Phe His Leu Pro Asp Ala Leu Glu Ile Glu Ala
            100                 105                 110
Cys Gln Val Tyr Phe Thr Tyr Asp Pro Tyr Ser Glu Glu Asp Pro Asp
        115                 120                 125
Glu Gly Val Ala Gly Ala Pro Thr Gly Ser Ser Pro Gln Pro Leu Gln
    130                 135                 140
Pro Leu Ser Gly Glu Asp Asp Ala Tyr Cys Thr Phe Pro Ser Arg Asp
145                 150                 155                 160
Asp Leu Leu Leu Phe Ser Pro Ser Leu Leu Gly Gly Pro Ser Pro Pro
                165                 170                 175
Ser Thr Ala Pro Gly Gly Ser Gly Ala Gly Glu Glu Arg Met Pro Pro
            180                 185                 190
Ser Leu Gln Glu Arg Val Pro Arg Asp Trp Asp Pro Gln Pro Leu Gly
        195                 200                 205
Pro Pro Thr Pro Gly Val Pro Asp Leu Val Asp Phe Gln Pro Pro Pro
    210                 215                 220
Glu Leu Val Leu Arg Glu Ala Gly Glu Glu Val Pro Asp Ala Gly Pro
225                 230                 235                 240
Arg Glu Gly Val Ser Phe Pro Trp Ser Arg Pro Pro Gly Gln Gly Glu
                245                 250                 255
Phe Arg Ala Leu Asn Ala Arg Leu Pro Leu Asn Thr Asp Ala Tyr Leu
            260                 265                 270
Ser Leu Gln Glu Leu Gln Gly Gln Asp Pro Thr His Leu Val
        275                 280                 285
```

<210> SEQ ID NO 3
<211> LENGTH: 195
<212> TYPE: PRT
<213> ORGANISM: Artificial Sequence
<220> FEATURE:
<223> OTHER INFORMATION: endodomain derived from IL-7 receptor alpha-chain

<400> SEQUENCE: 3

```
Lys Lys Arg Ile Lys Pro Ile Val Trp Pro Ser Leu Pro Asp His Lys
```

```
              1               5                  10                 15
            Lys Thr Leu Glu His Leu Cys Lys Lys Pro Arg Lys Asn Leu Asn Val
                            20                  25                 30

Ser Phe Asn Pro Glu Ser Phe Leu Asp Cys Gln Ile His Arg Val Asp
                            35                  40                 45

Asp Ile Gln Ala Arg Asp Glu Val Glu Gly Phe Leu Gln Asp Thr Phe
                            50                  55                 60

Pro Gln Gln Leu Glu Glu Ser Glu Lys Gln Arg Leu Gly Gly Asp Val
             65                  70                 75                 80

Gln Ser Pro Asn Cys Pro Ser Glu Asp Val Val Ile Thr Pro Glu Ser
                                85                 90                 95

Phe Gly Arg Asp Ser Ser Leu Thr Cys Leu Ala Gly Asn Val Ser Ala
                            100                 105                110

Cys Asp Ala Pro Ile Leu Ser Ser Arg Ser Leu Asp Cys Arg Glu
                            115                 120                125

Ser Gly Lys Asn Gly Pro His Val Tyr Gln Asp Leu Leu Ser Leu
                            130                 135                140

Gly Thr Thr Asn Ser Thr Leu Pro Pro Phe Ser Leu Gln Ser Gly
             145                 150                155                160

Ile Leu Thr Leu Asn Pro Val Ala Gln Gly Gln Pro Ile Leu Thr Ser
                            165                 170                175

Leu Gly Ser Asn Gln Glu Glu Ala Tyr Val Thr Met Ser Ser Phe Tyr
                            180                 185                190

Gln Asn Gln
                    195

<210> SEQ ID NO 4
<211> LENGTH: 234
<212> TYPE: PRT
<213> ORGANISM: Artificial Sequence
<220> FEATURE:
<223> OTHER INFORMATION: hinge-CH2CH3 of human IgG1

<400> SEQUENCE: 4

Ala Glu Pro Lys Ser Pro Asp Lys Thr His Thr Cys Pro Pro Cys Pro
             1               5                  10                 15

Ala Pro Pro Val Ala Gly Pro Ser Val Phe Leu Phe Pro Pro Lys Pro
                            20                  25                 30

Lys Asp Thr Leu Met Ile Ala Arg Thr Pro Glu Val Thr Cys Val Val
                            35                  40                 45

Val Asp Val Ser His Glu Asp Pro Glu Val Lys Phe Asn Trp Tyr Val
                            50                  55                 60

Asp Gly Val Glu Val His Asn Ala Lys Thr Lys Pro Arg Glu Glu Gln
             65                  70                 75                 80

Tyr Asn Ser Thr Tyr Arg Val Val Ser Val Leu Thr Val Leu His Gln
                            85                  90                 95

Asp Trp Leu Asn Gly Lys Glu Tyr Lys Cys Lys Val Ser Asn Lys Ala
                            100                 105                110

Leu Pro Ala Pro Ile Glu Lys Thr Ile Ser Lys Ala Lys Gly Gln Pro
                            115                 120                125

Arg Glu Pro Gln Val Tyr Thr Leu Pro Pro Ser Arg Asp Glu Leu Thr
                            130                 135                140

Lys Asn Gln Val Ser Leu Thr Cys Leu Val Lys Gly Phe Tyr Pro Ser
             145                 150                155                160

Asp Ile Ala Val Glu Trp Glu Ser Asn Gly Gln Pro Glu Asn Asn Tyr
```

```
                165                 170                 175
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Lys Asp
225                 230
```

<210> SEQ ID NO 5
<211> LENGTH: 46
<212> TYPE: PRT
<213> ORGANISM: Artificial Sequence
<220> FEATURE:
<223> OTHER INFORMATION: human CD8 stalk

<400> SEQUENCE: 5

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile
        35                  40                  45
```

<210> SEQ ID NO 6
<211> LENGTH: 20
<212> TYPE: PRT
<213> ORGANISM: Artificial Sequence
<220> FEATURE:
<223> OTHER INFORMATION: human IgG1 hinge

<400> SEQUENCE: 6

```
Ala Glu Pro Lys Ser Pro Asp Lys Thr His Thr Cys Pro Pro Cys Pro
1               5                   10                  15

Lys Asp Pro Lys
            20
```

<210> SEQ ID NO 7
<211> LENGTH: 21
<212> TYPE: PRT
<213> ORGANISM: Artificial Sequence
<220> FEATURE:
<223> OTHER INFORMATION: transmembrane derived from human common gamma
      chain

<400> SEQUENCE: 7

```
Val Val Ile Ser Val Gly Ser Met Gly Leu Ile Ile Ser Leu Leu Cys
1               5                   10                  15

Val Tyr Phe Trp Leu
            20
```

<210> SEQ ID NO 8
<211> LENGTH: 25
<212> TYPE: PRT
<213> ORGANISM: Artificial Sequence
<220> FEATURE:
<223> OTHER INFORMATION: transmembrane derived from human IL-2Rbeta

<400> SEQUENCE: 8

```
Ile Pro Trp Leu Gly His Leu Leu Val Gly Leu Ser Gly Ala Phe Gly
1               5                   10                  15
```

-continued

Phe Ile Ile Leu Val Tyr Leu Leu Ile
                20                  25

<210> SEQ ID NO 9
<211> LENGTH: 25
<212> TYPE: PRT
<213> ORGANISM: Artificial Sequence
<220> FEATURE:
<223> OTHER INFORMATION: transmembrane derived from human IL-7Ralpha

<400> SEQUENCE: 9

Pro Ile Leu Leu Thr Ile Ser Ile Leu Ser Phe Phe Ser Val Ala Leu
1               5                   10                  15

Leu Val Ile Leu Ala Cys Val Leu Trp
                20                  25

<210> SEQ ID NO 10
<211> LENGTH: 22
<212> TYPE: PRT
<213> ORGANISM: Artificial Sequence
<220> FEATURE:
<223> OTHER INFORMATION: transmembrane derived from human IL-15Ralpha

<400> SEQUENCE: 10

Ala Ile Ser Thr Ser Thr Val Leu Leu Cys Gly Leu Ser Ala Val Ser
1               5                   10                  15

Leu Leu Ala Cys Tyr Leu
                20

<210> SEQ ID NO 11
<211> LENGTH: 118
<212> TYPE: PRT
<213> ORGANISM: Artificial Sequence
<220> FEATURE:
<223> OTHER INFORMATION: sequence of 5D3D11 VH

<400> SEQUENCE: 11

Gln Val Gln Leu Gln Gln Ser Gly Pro Glu Leu Val Lys Pro Gly Ala
1               5                   10                  15

Ser Val Lys Ile Ser Cys Lys Val Ser Gly Tyr Ala Ile Ser Ser Ser
                20                  25                  30

Trp Met Asn Trp Val Lys Gln Arg Pro Gly Gln Gly Leu Glu Trp Ile
            35                  40                  45

Gly Arg Ile Tyr Pro Gly Asp Gly Asp Thr Lys Tyr Asn Gly Lys Phe
        50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Asp Gly Tyr Arg Tyr Tyr Phe Asp Tyr Trp Gly Gln Gly Thr
                100                 105                 110

Ser Val Thr Val Ser Ser
        115

<210> SEQ ID NO 12
<211> LENGTH: 112
<212> TYPE: PRT
<213> ORGANISM: Artificial Sequence
<220> FEATURE:
<223> OTHER INFORMATION: sequence of 5D3D11 VL

<400> SEQUENCE: 12

Asp Ile Val Met Thr Gln Thr Ala Pro Ser Val Phe Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Met Gln His
                85                  90                  95

Leu Glu Tyr Pro Val Thr Phe Gly Ala Gly Thr Lys Val Glu Ile Lys
            100                 105                 110

<210> SEQ ID NO 13
<211> LENGTH: 117
<212> TYPE: PRT
<213> ORGANISM: Artificial Sequence
<220> FEATURE:
<223> OTHER INFORMATION: sequence of 5D5A5 VH

<400> SEQUENCE: 13

Gln Val Gln Leu Gln Gln Ser Gly Ala Glu Leu Ala Lys Pro Gly Ala
1               5                   10                  15

Ser Val Lys Met Ser Cys Lys Thr Ser Gly Tyr Ser Phe Ser Ser Tyr
            20                  25                  30

Trp Met His Trp Val Lys Gln Arg Pro Gly Gln Gly Leu Glu Trp Ile
        35                  40                  45

Gly Tyr Ile Asn Pro Ser Thr Gly Tyr Thr Glu Asn Asn Gln Lys Phe
    50                  55                  60

Lys Asp Lys Val Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Gly Arg Leu Tyr Phe Asp Val Trp Gly Ala Gly Thr Thr
            100                 105                 110

Val Thr Val Ser Ser
        115

<210> SEQ ID NO 14
<211> LENGTH: 111
<212> TYPE: PRT
<213> ORGANISM: Artificial Sequence
<220> FEATURE:
<223> OTHER INFORMATION: sequence of 5D5A5 VL

<400> SEQUENCE: 14

Asp Ile Val Leu Thr Gln Ser Pro Pro Ser Leu Ala Val Ser Leu Gly
1               5                   10                  15

Gln Arg Ala Thr Ile Ser Cys Arg Ala Ser Glu Ser Ile Asp Leu Tyr
            20                  25                  30

Gly Phe Thr Phe Met His Trp Tyr Gln Gln Lys Pro Gly Gln Pro Pro
        35                  40                  45

Lys Ile Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Thr His
                85                  90                  95

Glu Asp Pro Tyr Thr Phe Gly Gly Gly Thr Lys Leu Glu Ile Lys
            100                 105                 110

<210> SEQ ID NO 15
<211> LENGTH: 248
<212> TYPE: PRT
<213> ORGANISM: Artificial Sequence
<220> FEATURE:
<223> OTHER INFORMATION: ScFv based on 5D5A5

<400> SEQUENCE: 15

Gln Val Gln Leu Gln Gln Ser Gly Ala Glu Leu Ala Lys Pro Gly Ala
1               5                   10                  15

Ser Val Lys Met Ser Cys Lys Thr Ser Gly Tyr Ser Phe Ser Ser Tyr
                20                  25                  30

Trp Met His Trp Val Lys Gln Arg Pro Gly Gln Gly Leu Glu Trp Ile
            35                  40                  45

Gly Tyr Ile Asn Pro Ser Thr Gly Tyr Thr Glu Asn Asn Gln Lys Phe
    50                  55                  60

Lys Asp Lys Val Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Tyr Cys
                85                  90                  95

Ala Arg Ser Gly Arg Leu Tyr Phe Asp Val Trp Gly Ala Gly Thr Thr
            100                 105                 110

Val Thr Val Ser Ser Gly Gly Gly Gly Ser Gly Gly Gly Gly Ser Gly
        115                 120                 125

Gly Gly Ser Gly Gly Gly Gly Ser Asp Ile Val Leu Thr Gln Ser
    130                 135                 140

Pro Pro Ser Leu Ala Val Ser Leu Gly Gln Arg Ala Thr Ile Ser Cys
145                 150                 155                 160

Arg Ala Ser Glu Ser Ile Asp Leu Tyr Gly Phe Thr Phe Met His Trp
                165                 170                 175

Tyr Gln Gln Lys Pro Gly Gln Pro Pro Lys Ile Leu Ile Tyr Arg Ala
            180                 185                 190

Ser Asn Leu Glu Ser Gly Ile Pro Ala Arg Phe Ser Gly Ser Gly Ser
        195                 200                 205

Arg Thr Asp Phe Thr Leu Thr Ile Asn Pro Val Glu Ala Asp Asp Val
    210                 215                 220

Ala Thr Tyr Tyr Cys Gln Gln Thr His Glu Asp Pro Tyr Thr Phe Gly
225                 230                 235                 240

Gly Gly Thr Lys Leu Glu Ile Lys
                245

<210> SEQ ID NO 16
<211> LENGTH: 250
<212> TYPE: PRT
<213> ORGANISM: Artificial Sequence
<220> FEATURE:
<223> OTHER INFORMATION: ScFv based on 5D3D11

<400> SEQUENCE: 16

Gln Val Gln Leu Gln Gln Ser Gly Pro Glu Leu Val Lys Pro Gly Ala
1               5                   10                  15

Ser Val Lys Ile Ser Cys Lys Val Ser Gly Tyr Ala Ile Ser Ser Ser

```
                20                  25                  30
Trp Met Asn Trp Val Lys Gln Arg Pro Gly Gln Gly Leu Glu Trp Ile
             35                  40                  45
Gly Arg Ile Tyr Pro Gly Asp Gly Asp Thr Lys Tyr Asn Gly Lys Phe
         50                  55                  60
Lys Asp Lys Ala Thr Leu Thr Val Asp Lys Ser Ser Thr Ala Tyr
65                  70                  75                  80
Met Gln Leu Ser Ser Leu Thr Ser Val Asp Ser Ala Val Tyr Phe Cys
                 85                  90                  95
Ala Arg Asp Gly Tyr Arg Tyr Tyr Phe Asp Tyr Trp Gly Gln Gly Thr
             100                 105                 110
Ser Val Thr Val Ser Ser Gly Gly Gly Gly Ser Gly Gly Gly Gly Ser
         115                 120                 125
Gly Gly Gly Gly Ser Gly Gly Gly Gly Ser Asp Ile Val Met Thr Gln
     130                 135                 140
Thr Ala Pro Ser Val Phe Val Thr Pro Gly Glu Ser Val Ser Ile Ser
145                 150                 155                 160
Cys Arg Ser Ser Lys Ser Leu Leu His Ser Asn Gly Asn Thr Tyr Leu
                 165                 170                 175
Tyr Trp Phe Leu Gln Arg Pro Gly Gln Ser Pro Gln Leu Leu Ile Tyr
             180                 185                 190
Arg Met Ser Asn Leu Ala Ser Gly Val Pro Asp Arg Phe Ser Gly Ser
         195                 200                 205
Gly Ser Gly Thr Asp Phe Thr Leu Arg Ile Ser Arg Val Glu Ala Glu
     210                 215                 220
Asp Val Gly Val Tyr Tyr Cys Met Gln His Leu Glu Tyr Pro Val Thr
225                 230                 235                 240
Phe Gly Ala Gly Thr Lys Val Glu Ile Lys
                 245                 250

<210> SEQ ID NO 17
<211> LENGTH: 356
<212> TYPE: PRT
<213> ORGANISM: Artificial Sequence
<220> FEATURE:
<223> OTHER INFORMATION: sequence of CXCR4

<400> SEQUENCE: 17

Met Ser Ile Pro Leu Pro Leu Leu Gln Ile Tyr Thr Ser Asp Asn Tyr
1               5                  10                  15
Thr Glu Glu Met Gly Ser Gly Asp Tyr Asp Ser Met Lys Glu Pro Cys
                20                  25                  30
Phe Arg Glu Glu Asn Ala Asn Phe Asn Lys Ile Phe Leu Pro Thr Ile
             35                  40                  45
Tyr Ser Ile Ile Phe Leu Thr Gly Ile Val Gly Asn Gly Leu Val Ile
         50                  55                  60
Leu Val Met Gly Tyr Gln Lys Lys Leu Arg Ser Met Thr Asp Lys Tyr
65                  70                  75                  80
Arg Leu His Leu Ser Val Ala Asp Leu Leu Phe Val Ile Thr Leu Pro
                 85                  90                  95
Phe Trp Ala Val Asp Ala Val Ala Asn Trp Tyr Phe Gly Asn Phe Leu
             100                 105                 110
Cys Lys Ala Val His Val Ile Tyr Thr Val Asn Leu Tyr Ser Ser Val
         115                 120                 125
Leu Ile Leu Ala Phe Ile Ser Leu Asp Arg Tyr Leu Ala Ile Val His
```

```
        130                 135                 140
Ala Thr Asn Ser Gln Arg Pro Arg Lys Leu Leu Ala Glu Lys Val Val
145                 150                 155                 160

Tyr Val Gly Val Trp Ile Pro Ala Leu Leu Leu Thr Ile Pro Asp Phe
                165                 170                 175

Ile Phe Ala Asn Val Ser Glu Ala Asp Asp Arg Tyr Ile Cys Asp Arg
            180                 185                 190

Phe Tyr Pro Asn Asp Leu Trp Val Val Phe Gln Phe Gln His Ile
        195                 200                 205

Met Val Gly Leu Ile Leu Pro Gly Ile Val Ile Leu Ser Cys Tyr Cys
    210                 215                 220

Ile Ile Ile Ser Lys Leu Ser His Ser Lys Gly His Gln Lys Arg Lys
225                 230                 235                 240

Ala Leu Lys Thr Thr Val Ile Leu Ile Leu Ala Phe Phe Ala Cys Trp
                245                 250                 255

Leu Pro Tyr Tyr Ile Gly Ile Ser Ile Asp Ser Phe Ile Leu Leu Glu
                260                 265                 270

Ile Ile Lys Gln Gly Cys Glu Phe Glu Asn Thr Val His Lys Trp Ile
            275                 280                 285

Ser Ile Thr Glu Ala Leu Ala Phe Phe His Cys Cys Leu Asn Pro Ile
        290                 295                 300

Leu Tyr Ala Phe Leu Gly Ala Lys Phe Lys Thr Ser Ala Gln His Ala
305                 310                 315                 320

Leu Thr Ser Val Ser Arg Gly Ser Ser Leu Lys Ile Leu Ser Lys Gly
                325                 330                 335

Lys Arg Gly Gly His Ser Ser Val Ser Thr Glu Ser Glu Ser Ser Ser
                340                 345                 350

Phe His Ser Ser
        355

<210> SEQ ID NO 18
<211> LENGTH: 374
<212> TYPE: PRT
<213> ORGANISM: Artificial Sequence
<220> FEATURE:
<223> OTHER INFORMATION: sequence of cell surface receptor CCR2

<400> SEQUENCE: 18

Met Leu Ser Thr Ser Arg Ser Arg Phe Ile Arg Asn Thr Asn Glu Ser
1               5                   10                  15

Gly Glu Glu Val Thr Thr Phe Phe Asp Tyr Asp Tyr Gly Ala Pro Cys
            20                  25                  30

His Lys Phe Asp Val Lys Gln Ile Gly Ala Gln Leu Leu Pro Pro Leu
        35                  40                  45

Tyr Ser Leu Val Phe Ile Phe Gly Phe Val Gly Asn Met Leu Val Val
    50                  55                  60

Leu Ile Leu Ile Asn Cys Lys Lys Leu Lys Cys Leu Thr Asp Ile Tyr
65                  70                  75                  80

Leu Leu Asn Leu Ala Ile Ser Asp Leu Phe Leu Ile Thr Leu Pro
                85                  90                  95

Leu Trp Ala His Ser Ala Ala Asn Glu Trp Val Phe Gly Asn Ala Met
                100                 105                 110

Cys Lys Leu Phe Thr Gly Leu Tyr His Ile Gly Tyr Phe Gly Gly Ile
            115                 120                 125

Phe Phe Ile Ile Leu Leu Thr Ile Asp Arg Tyr Leu Ala Ile Val His
```

```
            130                 135                 140

Ala Val Phe Ala Leu Lys Ala Arg Thr Val Thr Phe Gly Val Val Thr
145                 150                 155                 160

Ser Val Ile Thr Trp Leu Val Ala Val Phe Ala Ser Val Pro Gly Ile
                165                 170                 175

Ile Phe Thr Lys Cys Gln Lys Glu Asp Ser Val Tyr Val Cys Gly Pro
                180                 185                 190

Tyr Phe Pro Arg Gly Trp Asn Asn Phe His Thr Ile Met Arg Asn Ile
                195                 200                 205

Leu Gly Leu Val Leu Pro Leu Leu Ile Met Val Ile Cys Tyr Ser Gly
            210                 215                 220

Ile Leu Lys Thr Leu Leu Arg Cys Arg Asn Glu Lys Lys Arg His Arg
225                 230                 235                 240

Ala Val Arg Val Ile Phe Thr Ile Met Ile Val Tyr Phe Leu Phe Trp
                245                 250                 255

Thr Pro Tyr Asn Ile Val Ile Leu Leu Asn Thr Phe Gln Glu Phe Phe
                260                 265                 270

Gly Leu Ser Asn Cys Glu Ser Thr Ser Gln Leu Asp Gln Ala Thr Gln
                275                 280                 285

Val Thr Glu Thr Leu Gly Met Thr His Cys Cys Ile Asn Pro Ile Ile
290                 295                 300

Tyr Ala Phe Val Gly Glu Lys Phe Arg Ser Leu Phe His Ile Ala Leu
305                 310                 315                 320

Gly Cys Arg Ile Ala Pro Leu Gln Lys Pro Val Cys Gly Gly Pro Gly
                325                 330                 335

Val Arg Pro Gly Lys Asn Val Lys Val Thr Thr Gln Gly Leu Leu Asp
                340                 345                 350

Gly Arg Gly Lys Gly Lys Ser Ile Gly Arg Ala Pro Glu Ala Ser Leu
                355                 360                 365

Gln Asp Lys Glu Gly Ala
            370

<210> SEQ ID NO 19
<211> LENGTH: 360
<212> TYPE: PRT
<213> ORGANISM: Artificial Sequence
<220> FEATURE:
<223> OTHER INFORMATION: sequence of cell surface receptor CCR4

<400> SEQUENCE: 19

Met Asn Pro Thr Asp Ile Ala Asp Thr Thr Leu Asp Glu Ser Ile Tyr
1               5                   10                  15

Ser Asn Tyr Tyr Leu Tyr Glu Ser Ile Pro Lys Pro Cys Thr Lys Glu
                20                  25                  30

Gly Ile Lys Ala Phe Gly Glu Leu Phe Leu Pro Pro Leu Tyr Ser Leu
            35                  40                  45

Val Phe Val Phe Gly Leu Leu Gly Asn Ser Val Val Val Leu Val Leu
    50                  55                  60

Phe Lys Tyr Lys Arg Leu Arg Ser Met Thr Asp Val Tyr Leu Leu Asn
65                  70                  75                  80

Leu Ala Ile Ser Asp Leu Leu Phe Val Phe Ser Leu Pro Phe Trp Gly
                85                  90                  95

Tyr Tyr Ala Ala Asp Gln Trp Val Phe Gly Leu Gly Leu Cys Lys Met
                100                 105                 110

Ile Ser Trp Met Tyr Leu Val Gly Phe Tyr Ser Gly Ile Phe Phe Val
```

```
            115                 120                 125
Met Leu Met Ser Ile Asp Arg Tyr Leu Ala Ile Val His Ala Val Phe
            130                 135                 140

Ser Leu Arg Ala Arg Thr Leu Thr Tyr Gly Val Ile Thr Ser Leu Ala
145                 150                 155                 160

Thr Trp Ser Val Ala Val Phe Ala Ser Leu Pro Gly Phe Leu Phe Ser
                165                 170                 175

Thr Cys Tyr Thr Glu Arg Asn His Thr Tyr Cys Lys Thr Lys Tyr Ser
                180                 185                 190

Leu Asn Ser Thr Thr Trp Lys Val Leu Ser Ser Leu Glu Ile Asn Ile
                195                 200                 205

Leu Gly Leu Val Ile Pro Leu Gly Ile Met Leu Phe Cys Tyr Ser Met
            210                 215                 220

Ile Ile Arg Thr Leu Gln His Cys Lys Asn Glu Lys Lys Asn Lys Ala
225                 230                 235                 240

Val Lys Met Ile Phe Ala Val Val Val Leu Phe Leu Gly Phe Trp Thr
                245                 250                 255

Pro Tyr Asn Ile Val Leu Phe Leu Glu Thr Leu Val Glu Leu Glu Val
                260                 265                 270

Leu Gln Asp Cys Thr Phe Glu Arg Tyr Leu Asp Tyr Ala Ile Gln Ala
            275                 280                 285

Thr Glu Thr Leu Ala Phe Val His Cys Cys Leu Asn Pro Ile Ile Tyr
            290                 295                 300

Phe Phe Leu Gly Glu Lys Phe Arg Lys Tyr Ile Leu Gln Leu Phe Lys
305                 310                 315                 320

Thr Cys Arg Gly Leu Phe Val Leu Cys Gln Tyr Cys Gly Leu Leu Gln
                325                 330                 335

Ile Tyr Ser Ala Asp Thr Pro Ser Ser Ser Tyr Thr Gln Ser Thr Met
                340                 345                 350

Asp His Asp Leu His Asp Ala Leu
            355                 360

<210> SEQ ID NO 20
<211> LENGTH: 238
<212> TYPE: PRT
<213> ORGANISM: Artificial Sequence
<220> FEATURE:
<223> OTHER INFORMATION: scFv based on J591

<400> SEQUENCE: 20

Glu Val Gln Leu Gln Gln Ser Gly Pro Glu Leu Lys Lys Pro Gly Thr
1               5                   10                  15

Ser Val Arg Ile Ser Cys Lys Thr Ser Gly Tyr Thr Phe Thr Glu Tyr
                20                  25                  30

Thr Ile His Trp Val Lys Gln Ser His Gly Lys Ser Leu Glu Trp Ile
                35                  40                  45

Gly Asn Ile Asn Pro Asn Asn Gly Gly Thr Thr Tyr Asn Gln Lys Phe
            50                  55                  60

Glu Asp Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Ala Gly Trp Asn Phe Asp Tyr Trp Gly Gln Gly Thr Thr Leu Thr
                100                 105                 110

Val Ser Ser Gly Gly Gly Gly Ser Gly Gly Gly Gly Ser Gly Gly Gly
```

```
                115                 120                 125
Gly Ser Asp Ile Val Met Thr Gln Ser His Lys Phe Met Ser Thr Ser
        130                 135                 140

Val Gly Asp Arg Val Ser Ile Ile Cys Lys Ala Ser Gln Asp Val Gly
145                 150                 155                 160

Thr Ala Val Asp Trp Tyr Gln Gln Lys Pro Gly Gln Ser Pro Lys Leu
                165                 170                 175

Leu Ile Tyr Trp Ala Ser Thr Arg His Thr Gly Val Pro Asp Arg Phe
            180                 185                 190

Thr Gly Ser Gly Ser Gly Thr Asp Phe Thr Leu Thr Ile Thr Asn Val
        195                 200                 205

Gln Ser Glu Asp Leu Ala Asp Tyr Phe Cys Gln Gln Tyr Asn Ser Tyr
    210                 215                 220

Pro Leu Thr Phe Gly Ala Gly Thr Met Leu Asp Leu Lys Arg
225                 230                 235

<210> SEQ ID NO 21
<211> LENGTH: 21
<212> TYPE: PRT
<213> ORGANISM: Artificial Sequence
<220> FEATURE:
<223> OTHER INFORMATION: signal peptide derived from TCR beta chain

<400> SEQUENCE: 21

Met Gly Thr Ser Leu Leu Cys Trp Met Ala Leu Cys Leu Leu Gly Ala
1               5                   10                  15

Asp His Ala Asp Gly
            20

<210> SEQ ID NO 22
<211> LENGTH: 21
<212> TYPE: PRT
<213> ORGANISM: Artificial Sequence
<220> FEATURE:
<223> OTHER INFORMATION: signal peptide derived from IgG1

<400> SEQUENCE: 22

Met Ser Leu Pro Val Thr Ala Leu Leu Leu Pro Leu Ala Leu Leu Leu
1               5                   10                  15

His Ala Ala Arg Pro
            20

<210> SEQ ID NO 23
<211> LENGTH: 20
<212> TYPE: PRT
<213> ORGANISM: Artificial Sequence
<220> FEATURE:
<223> OTHER INFORMATION: signal peptide derived from CD8a

<400> SEQUENCE: 23

Met Ala Val Pro Thr Gln Val Leu Gly Leu Leu Leu Leu Trp Leu Thr
1               5                   10                  15

Asp Ala Arg Cys
            20

<210> SEQ ID NO 24
<211> LENGTH: 112
<212> TYPE: PRT
<213> ORGANISM: Artificial Sequence
<220> FEATURE:
<223> OTHER INFORMATION: CD3 Z endodomain
```

<400> SEQUENCE: 24

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 25
<211> LENGTH: 152
<212> TYPE: PRT
<213> ORGANISM: Artificial Sequence
<220> FEATURE:
<223> OTHER INFORMATION: CD28 and CD3 Zeta endodomains

<400> SEQUENCE: 25

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Val Lys Phe Ser Arg Ser Ala
        35                  40                  45

Asp Ala Pro Ala Tyr Gln Gln Gly Gln Asn Gln Leu Tyr Asn Glu Leu
    50                  55                  60

Asn Leu Gly Arg Arg Glu Glu Tyr Asp Val Leu Asp Lys Arg Arg Gly
65                  70                  75                  80

Arg Asp Pro Glu Met Gly Gly Lys Pro Arg Arg Lys Asn Pro Gln Glu
                85                  90                  95

Gly Leu Tyr Asn Glu Leu Gln Lys Asp Lys Met Ala Glu Ala Tyr Ser
            100                 105                 110

Glu Ile Gly Met Lys Gly Glu Arg Arg Gly Lys Gly His Asp Gly
        115                 120                 125

Leu Tyr Gln Gly Leu Ser Thr Ala Thr Lys Asp Thr Tyr Asp Ala Leu
    130                 135                 140

His Met Gln Ala Leu Pro Pro Arg
145                 150

<210> SEQ ID NO 26
<211> LENGTH: 188
<212> TYPE: PRT
<213> ORGANISM: Artificial Sequence
<220> FEATURE:
<223> OTHER INFORMATION: CD28, OX40 and CD3 Zeta endodomains

<400> SEQUENCE: 26

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser Arg Asp Gln Arg Leu Pro Pro Asp
            35                  40                  45

Ala His Lys Pro Pro Gly Gly Gly Ser Phe Arg Thr Pro Ile Gln Glu
 50                  55                  60

Glu Gln Ala Asp Ala His Ser Thr Leu Ala Lys Ile Arg Val Lys Phe
 65                  70                  75                  80

Ser Arg Ser Ala Asp Ala Pro Ala Tyr Gln Gln Gly Gln Asn Gln Leu
                 85                  90                  95

Tyr Asn Glu Leu Asn Leu Gly Arg Arg Glu Glu Tyr Asp Val Leu Asp
            100                 105                 110

Lys Arg Arg Gly Arg Asp Pro Glu Met Gly Gly Lys Pro Arg Arg Lys
            115                 120                 125

Asn Pro Gln Glu Gly Leu Tyr Asn Glu Leu Gln Lys Asp Lys Met Ala
            130                 135                 140

Glu Ala Tyr Ser Glu Ile Gly Met Lys Gly Glu Arg Arg Arg Gly Lys
145                 150                 155                 160

Gly His Asp Gly Leu Tyr Gln Gly Leu Ser Thr Ala Thr Lys Asp Thr
                165                 170                 175

Tyr Asp Ala Leu His Met Gln Ala Leu Pro Pro Arg
            180                 185

<210> SEQ ID NO 27
<211> LENGTH: 38
<212> TYPE: PRT
<213> ORGANISM: Artificial Sequence
<220> FEATURE:
<223> OTHER INFORMATION: ICOS endodomain

<400> SEQUENCE: 27

Cys Trp Leu Thr Lys Lys Lys Tyr Ser Ser Val His Asp Pro Asn
 1               5                   10                  15

Gly Glu Tyr Met Phe Met Arg Ala Val Asn Thr Ala Lys Lys Ser Arg
            20                  25                  30

Leu Thr Asp Val Thr Leu
        35

<210> SEQ ID NO 28
<211> LENGTH: 48
<212> TYPE: PRT
<213> ORGANISM: Artificial Sequence
<220> FEATURE:
<223> OTHER INFORMATION: CD27 endodomain

<400> SEQUENCE: 28

Gln Arg Arg Lys Tyr Arg Ser Asn Lys Gly Glu Ser Pro Val Glu Pro
 1               5                   10                  15

Ala Glu Pro Cys His Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
            35                  40                  45

<210> SEQ ID NO 29
<211> LENGTH: 111
<212> TYPE: PRT
<213> ORGANISM: Artificial Sequence
<220> FEATURE:
<223> OTHER INFORMATION: BTLA endodomain

<400> SEQUENCE: 29

Arg Arg His Gln Gly Lys Gln Asn Glu Leu Ser Asp Thr Ala Gly Arg

```
                1               5                   10                  15
            Glu Ile Asn Leu Val Asp Ala His Leu Lys Ser Glu Gln Thr Glu Ala
                        20                  25                  30

Ser Thr Arg Gln Asn Ser Gln Val Leu Leu Ser Glu Thr Gly Ile Tyr
                        35                  40                  45

Asp Asn Asp Pro Asp Leu Cys Phe Arg Met Gln Gly Ser Glu Val
                50                  55                  60

Tyr Ser Asn Pro Cys Leu Glu Glu Asn Lys Pro Gly Ile Val Tyr Ala
             65                 70                  75                  80

Ser Leu Asn His Ser Val Ile Gly Pro Asn Ser Arg Leu Ala Arg Asn
                        85                  90                  95

Val Lys Glu Ala Pro Thr Glu Tyr Ala Ser Ile Cys Val Arg Ser
                        100                 105                 110

<210> SEQ ID NO 30
<211> LENGTH: 188
<212> TYPE: PRT
<213> ORGANISM: Artificial Sequence
<220> FEATURE:
<223> OTHER INFORMATION: CD30 endodomain

<400> SEQUENCE: 30

His Arg Arg Ala Cys Arg Lys Arg Ile Arg Gln Lys Leu His Leu Cys
            1               5                   10                  15

Tyr Pro Val Gln Thr Ser Gln Pro Lys Leu Glu Leu Val Asp Ser Arg
                        20                  25                  30

Pro Arg Arg Ser Ser Thr Gln Leu Arg Ser Gly Ala Ser Val Thr Glu
                        35                  40                  45

Pro Val Ala Glu Glu Arg Gly Leu Met Ser Gln Pro Leu Met Glu Thr
                50                  55                  60

Cys His Ser Val Gly Ala Ala Tyr Leu Glu Ser Leu Pro Leu Gln Asp
             65                 70                  75                  80

Ala Ser Pro Ala Gly Gly Pro Ser Ser Pro Arg Asp Leu Pro Glu Pro
                        85                  90                  95

Arg Val Ser Thr Glu His Thr Asn Asn Lys Ile Glu Lys Ile Tyr Ile
                        100                 105                 110

Met Lys Ala Asp Thr Val Ile Val Gly Thr Val Lys Ala Glu Leu Pro
                        115                 120                 125

Glu Gly Arg Gly Leu Ala Gly Pro Ala Glu Pro Glu Leu Glu Glu Glu
                        130                 135                 140

Leu Glu Ala Asp His Thr Pro His Tyr Pro Glu Gln Glu Thr Glu Pro
            145                 150                 155                 160

Pro Leu Gly Ser Cys Ser Asp Val Met Leu Ser Val Glu Glu Glu Gly
                        165                 170                 175

Lys Glu Asp Pro Leu Pro Thr Ala Ala Ser Gly Lys
                        180                 185

<210> SEQ ID NO 31
<211> LENGTH: 58
<212> TYPE: PRT
<213> ORGANISM: Artificial Sequence
<220> FEATURE:
<223> OTHER INFORMATION: GITR endodomain

<400> SEQUENCE: 31

Gln Leu Gly Leu His Ile Trp Gln Leu Arg Ser Gln Cys Met Trp Pro
            1               5                   10                  15
```

```
Arg Glu Thr Gln Leu Leu Leu Glu Val Pro Pro Ser Thr Glu Asp Ala
             20                  25                  30

Arg Ser Cys Gln Phe Pro Glu Glu Glu Arg Gly Glu Arg Ser Ala Glu
         35                  40                  45

Glu Lys Gly Arg Leu Gly Asp Leu Trp Val
     50                  55

<210> SEQ ID NO 32
<211> LENGTH: 60
<212> TYPE: PRT
<213> ORGANISM: Artificial Sequence
<220> FEATURE:
<223> OTHER INFORMATION: HVEM endodomain

<400> SEQUENCE: 32

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
             20                  25                  30

Glu Ala Leu Gln Ala Pro Pro Asp Val Thr Thr Val Ala Val Glu Glu
         35                  40                  45

Thr Ile Pro Ser Phe Thr Gly Arg Ser Pro Asn His
     50                  55                  60

<210> SEQ ID NO 33
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 33

Tyr His Ala Asp Tyr Tyr Lys Gln Arg Leu Ile His Asp Val Glu Met
1               5                   10                  15

Asn Pro Gly Pro
             20

<210> SEQ ID NO 34
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 34

His Tyr Ala Gly Tyr Phe Ala Asp Leu Leu Ile His Asp Ile Glu Thr
1               5                   10                  15

Asn Pro Gly Pro
             20

<210> SEQ ID NO 35
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 35

Gln Cys Thr Asn Tyr Ala Leu Leu Lys Leu Ala Gly Asp Val Glu Ser
1               5                   10                  15

Asn Pro Gly Pro
             20
```

```
<210> SEQ ID NO 36
<211> LENGTH: 19
<212> TYPE: PRT
<213> ORGANISM: Artificial Sequence
<220> FEATURE:
<223> OTHER INFORMATION: cleavage site, 2A-like sequence

<400> SEQUENCE: 36

Ala Thr Asn Phe Ser Leu Leu Lys Gln Ala Gly Asp Val Glu Glu Asn
1               5                   10                  15

Pro Gly Pro

<210> SEQ ID NO 37
<211> LENGTH: 19
<212> TYPE: PRT
<213> ORGANISM: Artificial Sequence
<220> FEATURE:
<223> OTHER INFORMATION: cleavage site, 2A-like sequence

<400> SEQUENCE: 37

Ala Ala Arg Gln Met Leu Leu Leu Leu Ser Gly Asp Val Glu Thr Asn
1               5                   10                  15

Pro Gly Pro

<210> SEQ ID NO 38
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 38

Arg Ala Glu Gly Arg Gly Ser Leu Leu Thr Cys Gly Asp Val Glu Glu
1               5                   10                  15

Asn Pro Gly Pro
            20

<210> SEQ ID NO 39
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 39

Thr Arg Ala Glu Ile Glu Asp Glu Leu Ile Arg Ala Gly Ile Glu Ser
1               5                   10                  15

Asn Pro Gly Pro
            20

<210> SEQ ID NO 40
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 40

Thr Arg Ala Glu Ile Glu Asp Glu Leu Ile Arg Ala Asp Ile Glu Ser
1               5                   10                  15

Asn Pro Gly Pro
            20
```

<210> SEQ ID NO 41
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 41

Ala Lys Phe Gln Ile Asp Lys Ile Leu Ile Ser Gly Asp Val Glu Leu
1               5                   10                  15

Asn Pro Gly Pro
            20

<210> SEQ ID NO 42
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 42

Ser Ser Ile Ile Arg Thr Lys Met Leu Val Ser Gly Asp Val Glu Glu
1               5                   10                  15

Asn Pro Gly Pro
            20

<210> SEQ ID NO 43
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 43

Cys Asp Ala Gln Arg Gln Lys Leu Leu Leu Ser Gly Asp Ile Glu Gln
1               5                   10                  15

Asn Pro Gly Pro
            20

<210> SEQ ID NO 44
<211> LENGTH: 20
<212> TYPE: PRT
<213> ORGANISM: Artificial Sequence
<220> FEATURE:
<223> OTHER INFORMATION: cleavage site, 2A-like sequence

<400> SEQUENCE: 44

Tyr Pro Ile Asp Phe Gly Gly Phe Leu Val Lys Ala Asp Ser Glu Phe
1               5                   10                  15

Asn Pro Gly Pro
            20

<210> SEQ ID NO 45
<211> LENGTH: 1722
<212> TYPE: PRT
<213> ORGANISM: Artificial Sequence
<220> FEATURE:
<223> OTHER INFORMATION: fusion construct with IL-2R beta chain

<400> SEQUENCE: 45

Met Ser Leu Pro Val Thr Ala Leu Leu Leu Pro Leu Ala Leu Leu Leu
1               5                   10                  15

His Ala Ala Glu Val Gln Leu Gln Gln Ser Gly Pro Glu Leu Lys Lys
            20                  25                  30

Pro Gly Thr Ser Val Arg Ile Ser Cys Lys Thr Ser Gly Tyr Thr Phe
            35                  40                  45

Thr Glu Tyr Thr Ile His Trp Val Lys Gln Ser His Gly Lys Ser Leu
 50                  55                  60

Glu Trp Ile Gly Asn Ile Asn Pro Asn Asn Gly Gly Thr Thr Tyr Asn
 65                  70                  75                  80

Gln Lys Phe Glu Asp Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
                100                 105                 110

Tyr Tyr Cys Ala Ala Gly Trp Asn Phe Asp Tyr Trp Gly Gln Gly Thr
            115                 120                 125

Thr Leu Thr Val Ser Ser Gly Gly Gly Gly Ser Gly Gly Gly Gly Ser
130                 135                 140

Gly Gly Gly Gly Ser Asp Ile Val Met Thr Gln Ser His Lys Phe Met
145                 150                 155                 160

Ser Thr Ser Val Gly Asp Arg Val Ser Ile Ile Cys Lys Ala Ser Gln
                165                 170                 175

Asp Val Gly Thr Ala Val Asp Trp Tyr Gln Gln Lys Pro Gly Gln Ser
            180                 185                 190

Pro Lys Leu Leu Ile Tyr Trp Ala Ser Thr Arg His Thr Gly Val Pro
            195                 200                 205

Asp Arg Phe Thr Gly Ser Gly Ser Gly Thr Asp Phe Thr Leu Thr Ile
            210                 215                 220

Thr Asn Val Gln Ser Glu Asp Leu Ala Asp Tyr Phe Cys Gln Gln Tyr
225                 230                 235                 240

Asn Ser Tyr Pro Leu Thr Phe Gly Ala Gly Thr Met Leu Asp Leu Lys
            245                 250                 255

Arg Ser Asp Pro Ala Glu Pro Lys Ser Pro Asp Lys Thr His Thr Cys
            260                 265                 270

Pro Pro Cys Pro Ala Pro Pro Val Ala Gly Pro Ser Val Phe Leu Phe
            275                 280                 285

Pro Pro Lys Pro Lys Asp Thr Leu Met Ile Ala Arg Thr Pro Glu Val
            290                 295                 300

Thr Cys Val Val Val Asp Val Ser His Glu Asp Pro Glu Val Lys Phe
305                 310                 315                 320

Asn Trp Tyr Val Asp Gly Val Glu Val His Asn Ala Lys Thr Lys Pro
            325                 330                 335

Arg Glu Glu Gln Tyr Asn Ser Thr Tyr Arg Val Val Ser Val Leu Thr
            340                 345                 350

Val Leu His Gln Asp Trp Leu Asn Gly Lys Glu Tyr Lys Cys Lys Val
            355                 360                 365

Ser Asn Lys Ala Leu Pro Ala Pro Ile Glu Lys Thr Ile Ser Lys Ala
370                 375                 380

Lys Gly Gln Pro Arg Glu Pro Gln Val Tyr Thr Leu Pro Pro Ser Arg
385                 390                 395                 400

Asp Glu Leu Thr Lys Asn Gln Val Ser Leu Thr Cys Leu Val Lys Gly
            405                 410                 415

Phe Tyr Pro Ser Asp Ile Ala Val Glu Trp Glu Ser Asn Gly Gln Pro
            420                 425                 430

Glu Asn Asn Tyr Lys Thr Thr Pro Pro Val Leu Asp Ser Asp Gly Ser
            435                 440                 445

Phe Phe Leu Tyr Ser Lys Leu Thr Val Asp Lys Ser Arg Trp Gln Gln

-continued

```
                450             455             460
Gly Asn Val Phe Ser Cys Ser Val Met His Glu Ala Leu His Asn His
465                 470                 475                 480

Tyr Thr Gln Lys Ser Leu Ser Leu Ser Pro Gly Lys Phe Trp Val Leu
                485                 490                 495

Val Val Val Gly Gly Val Leu Ala Cys Tyr Ser Leu Leu Val Thr Val
            500                 505                 510

Ala Phe Ile Ile Phe Trp Val Arg Arg Val Lys Phe Ser Arg Ser Ala
        515                 520                 525

Asp Ala Pro Ala Tyr Gln Gln Gly Gln Asn Gln Leu Tyr Asn Glu Leu
    530                 535                 540

Asn Leu Gly Arg Arg Glu Glu Tyr Asp Val Leu Asp Lys Arg Arg Gly
545                 550                 555                 560

Arg Asp Pro Glu Met Gly Gly Lys Pro Arg Arg Lys Asn Pro Gln Glu
                565                 570                 575

Gly Leu Tyr Asn Glu Leu Gln Lys Asp Lys Met Ala Glu Ala Tyr Ser
                580                 585                 590

Glu Ile Gly Met Lys Gly Glu Arg Arg Arg Gly Lys Gly His Asp Gly
                595                 600                 605

Leu Tyr Gln Gly Leu Ser Thr Ala Thr Lys Asp Thr Tyr Asp Ala Leu
                610                 615                 620

His Met Gln Ala Leu Pro Pro Arg Arg Ala Glu Gly Arg Gly Ser Leu
625                 630                 635                 640

Leu Thr Cys Gly Asp Val Glu Glu Asn Pro Gly Pro Met Glu Thr Asp
                645                 650                 655

Thr Leu Ile Leu Trp Val Leu Leu Leu Val Pro Gly Ser Thr Gly
                660                 665                 670

Gln Val Gln Leu Gln Gln Ser Gly Ala Glu Leu Ala Lys Pro Gly Ala
                675                 680                 685

Ser Val Lys Met Ser Cys Lys Thr Ser Gly Tyr Ser Phe Ser Ser Tyr
                690                 695                 700

Trp Met His Trp Val Lys Gln Arg Pro Gly Gln Gly Leu Glu Trp Ile
705                 710                 715                 720

Gly Tyr Ile Asn Pro Ser Thr Gly Tyr Thr Glu Asn Asn Gln Lys Phe
                725                 730                 735

Lys Asp Lys Val Thr Leu Thr Ala Asp Lys Ser Ser Asn Thr Ala Tyr
                740                 745                 750

Met Gln Leu Asn Ser Leu Thr Ser Glu Asp Ser Ala Val Tyr Tyr Cys
                755                 760                 765

Ala Arg Ser Gly Arg Leu Tyr Phe Asp Val Trp Gly Ala Gly Thr Thr
                770                 775                 780

Val Thr Val Ser Ser Gly Gly Gly Gly Ser Gly Gly Gly Gly Ser Gly
785                 790                 795                 800

Gly Gly Ser Gly Gly Gly Gly Ser Asp Ile Val Leu Thr Gln Ser
                805                 810                 815

Pro Pro Ser Leu Ala Val Ser Leu Gly Gln Arg Ala Thr Ile Ser Cys
                820                 825                 830

Arg Ala Ser Glu Ser Ile Asp Leu Tyr Gly Phe Thr Phe Met His Trp
                835                 840                 845

Tyr Gln Gln Lys Pro Gly Gln Pro Pro Lys Ile Leu Ile Tyr Arg Ala
                850                 855                 860

Ser Asn Leu Glu Ser Gly Ile Pro Ala Arg Phe Ser Gly Ser Gly Ser
865                 870                 875                 880
```

-continued

Arg Thr Asp Phe Thr Leu Thr Ile Asn Pro Val Glu Ala Asp Val
                885                 890                 895

Ala Thr Tyr Tyr Cys Gln Gln Thr His Glu Asp Pro Tyr Thr Phe Gly
            900                 905                 910

Gly Gly Thr Lys Leu Glu Ile Lys Ser Asp Pro Ala Thr Thr Pro
        915                 920                 925

Ala Pro Arg Pro Pro Thr Pro Ala Pro Thr Ile Ala Ser Gln Pro Leu
930                 935                 940

Ser Leu Arg Pro Glu Ala Cys Arg Pro Ala Ala Gly Gly Ala Val His
945                 950                 955                 960

Thr Arg Gly Leu Asp Phe Ala Cys Asp Ile Val Val Ile Ser Val Gly
                965                 970                 975

Ser Met Gly Leu Ile Ile Ser Leu Leu Cys Val Tyr Phe Trp Leu Glu
            980                 985                 990

Arg Thr Met Pro Arg Ile Pro Thr Leu Lys Asn Leu Glu Asp Leu Val
        995                 1000                1005

Thr Glu Tyr His Gly Asn Phe Ser Ala Trp Ser Gly Val Ser Lys
    1010                1015                1020

Gly Leu Ala Glu Ser Leu Gln Pro Asp Tyr Ser Glu Arg Leu Cys
    1025                1030                1035

Leu Val Ser Glu Ile Pro Pro Lys Gly Gly Ala Leu Gly Glu Gly
    1040                1045                1050

Pro Gly Ala Ser Pro Cys Asn Gln His Ser Pro Tyr Trp Ala Pro
    1055                1060                1065

Pro Cys Tyr Thr Leu Lys Pro Glu Thr Gln Cys Thr Asn Tyr Ala
    1070                1075                1080

Leu Leu Lys Leu Ala Gly Asp Val Glu Ser Asn Pro Gly Pro Met
    1085                1090                1095

Glu Thr Asp Thr Leu Ile Leu Trp Val Leu Leu Leu Val Pro
    1100                1105                1110

Gly Ser Thr Gly Gln Val Gln Leu Gln Gln Ser Gly Pro Glu Leu
    1115                1120                1125

Val Lys Pro Gly Ala Ser Val Lys Ile Ser Cys Lys Val Ser Gly
    1130                1135                1140

Tyr Ala Ile Ser Ser Ser Trp Met Asn Trp Val Lys Gln Arg Pro
    1145                1150                1155

Gly Gln Gly Leu Glu Trp Ile Gly Arg Ile Tyr Pro Gly Asp Gly
    1160                1165                1170

Asp Thr Lys Tyr Asn Gly Lys Phe Lys Asp Lys Ala Thr Leu Thr
    1175                1180                1185

Val Asp Lys Ser Ser Ser Thr Ala Tyr Met Gln Leu Ser Ser Leu
    1190                1195                1200

Thr Ser Val Asp Ser Ala Val Tyr Phe Cys Ala Arg Asp Gly Tyr
    1205                1210                1215

Arg Tyr Tyr Phe Asp Tyr Trp Gly Gln Gly Thr Ser Val Thr Val
    1220                1225                1230

Ser Ser Gly Gly Gly Gly Ser Gly Gly Gly Gly Ser Gly Gly Gly
    1235                1240                1245

Gly Ser Gly Gly Gly Gly Ser Asp Ile Val Met Thr Gln Thr Ala
    1250                1255                1260

Pro Ser Val Phe Val Thr Pro Gly Glu Ser Val Ser Ile Ser Cys
    1265                1270                1275

-continued

Arg Ser Ser Lys Ser Leu Leu His Ser Asn Gly Asn Thr Tyr Leu
    1280            1285                1290

Tyr Trp Phe Leu Gln Arg Pro Gly Gln Ser Pro Gln Leu Leu Ile
    1295            1300                1305

Tyr Arg Met Ser Asn Leu Ala Ser Gly Val Pro Asp Arg Phe Ser
    1310            1315                1320

Gly Ser Gly Ser Gly Thr Asp Phe Thr Leu Arg Ile Ser Arg Val
    1325            1330                1335

Glu Ala Glu Asp Val Gly Val Tyr Tyr Cys Met Gln His Leu Glu
    1340            1345                1350

Tyr Pro Val Thr Phe Gly Ala Gly Thr Lys Val Glu Ile Lys Ser
    1355            1360                1365

Asp Pro Ala Lys Ile Glu Val Met Tyr Pro Pro Tyr Leu Asp
    1370            1375                1380

Asn Glu Lys Ser Asn Gly Thr Ile Ile His Val Lys Gly Lys His
    1385            1390                1395

Leu Cys Pro Ser Pro Leu Phe Pro Gly Pro Ser Lys Pro Ile Pro
    1400            1405                1410

Trp Leu Gly His Leu Leu Val Gly Leu Ser Gly Ala Phe Gly Phe
    1415            1420                1425

Ile Ile Leu Val Tyr Leu Leu Ile Asn Cys Arg Asn Thr Gly Pro
    1430            1435                1440

Trp Leu Lys Lys Val Leu Lys Cys Asn Thr Pro Asp Pro Ser Lys
    1445            1450                1455

Phe Phe Ser Gln Leu Ser Ser Glu His Gly Gly Asp Val Gln Lys
    1460            1465                1470

Trp Leu Ser Ser Pro Phe Pro Ser Ser Ser Phe Ser Pro Gly Gly
    1475            1480                1485

Leu Ala Pro Glu Ile Ser Pro Leu Glu Val Leu Glu Arg Asp Lys
    1490            1495                1500

Val Thr Gln Leu Leu Leu Gln Asp Lys Val Pro Glu Pro Ala
    1505            1510                1515

Ser Leu Ser Ser Asn His Ser Leu Thr Ser Cys Phe Thr Asn Gln
    1520            1525                1530

Gly Tyr Phe Phe Phe His Leu Pro Asp Ala Leu Glu Ile Glu Ala
    1535            1540                1545

Cys Gln Val Tyr Phe Thr Tyr Asp Pro Tyr Ser Glu Glu Asp Pro
    1550            1555                1560

Asp Glu Gly Val Ala Gly Ala Pro Thr Gly Ser Ser Pro Gln Pro
    1565            1570                1575

Leu Gln Pro Leu Ser Gly Glu Asp Asp Ala Tyr Cys Thr Phe Pro
    1580            1585                1590

Ser Arg Asp Asp Leu Leu Leu Phe Ser Pro Ser Leu Leu Gly Gly
    1595            1600                1605

Pro Ser Pro Pro Ser Thr Ala Pro Gly Gly Ser Gly Ala Gly Glu
    1610            1615                1620

Glu Arg Met Pro Pro Ser Leu Gln Glu Arg Val Pro Arg Asp Trp
    1625            1630                1635

Asp Pro Gln Pro Leu Gly Pro Pro Thr Pro Gly Val Pro Asp Leu
    1640            1645                1650

Val Asp Phe Gln Pro Pro Pro Glu Leu Val Leu Arg Glu Ala Gly
    1655            1660                1665

Glu Glu Val Pro Asp Ala Gly Pro Arg Glu Gly Val Ser Phe Pro

```
            1670                1675                1680
Trp Ser Arg Pro Gly Gln Gly Glu Phe Arg Ala Leu Asn Ala
        1685                1690                1695

Arg Leu Pro Leu Asn Thr Asp Ala Tyr Leu Ser Leu Gln Glu Leu
    1700                1705                1710

Gln Gly Gln Asp Pro Thr His Leu Val
    1715                1720

<210> SEQ ID NO 46
<211> LENGTH: 1631
<212> TYPE: PRT
<213> ORGANISM: Artificial Sequence
<220> FEATURE:
<223> OTHER INFORMATION: fusion construct with IL-7R alpha chain

<400> SEQUENCE: 46

Met Ser Leu Pro Val Thr Ala Leu Leu Leu Pro Leu Ala Leu Leu Leu
1               5                   10                  15

His Ala Ala Glu Val Gln Leu Gln Gln Ser Gly Pro Glu Leu Lys Lys
            20                  25                  30

Pro Gly Thr Ser Val Arg Ile Ser Cys Lys Thr Ser Gly Tyr Thr Phe
        35                  40                  45

Thr Glu Tyr Thr Ile His Trp Val Lys Gln Ser His Gly Lys Ser Leu
    50                  55                  60

Glu Trp Ile Gly Asn Ile Asn Pro Asn Asn Gly Gly Thr Thr Tyr Asn
65                  70                  75                  80

Gln Lys Phe Glu Asp Lys Ala Thr Leu Thr Val Asp Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Ala Gly Trp Asn Phe Asp Tyr Trp Gly Gln Gly Thr
        115                 120                 125

Thr Leu Thr Val Ser Ser Gly Gly Gly Gly Ser Gly Gly Gly Gly Ser
    130                 135                 140

Gly Gly Gly Gly Ser Asp Ile Val Met Thr Gln Ser His Lys Phe Met
145                 150                 155                 160

Ser Thr Ser Val Gly Asp Arg Val Ser Ile Ile Cys Lys Ala Ser Gln
                165                 170                 175

Asp Val Gly Thr Ala Val Asp Trp Tyr Gln Gln Lys Pro Gly Gln Ser
            180                 185                 190

Pro Lys Leu Leu Ile Tyr Trp Ala Ser Thr Arg His Thr Gly Val Pro
        195                 200                 205

Asp Arg Phe Thr Gly Ser Gly Ser Gly Thr Asp Phe Thr Leu Thr Ile
    210                 215                 220

Thr Asn Val Gln Ser Glu Asp Leu Ala Asp Tyr Phe Cys Gln Gln Tyr
225                 230                 235                 240

Asn Ser Tyr Pro Leu Thr Phe Gly Ala Gly Thr Met Leu Asp Leu Lys
                245                 250                 255

Arg Ser Asp Pro Ala Glu Pro Lys Ser Pro Asp Lys Thr His Thr Cys
            260                 265                 270

Pro Pro Cys Pro Ala Pro Pro Val Ala Gly Pro Ser Val Phe Leu Phe
        275                 280                 285

Pro Pro Lys Pro Lys Asp Thr Leu Met Ile Ala Arg Thr Pro Glu Val
    290                 295                 300

Thr Cys Val Val Val Asp Val Ser His Glu Asp Pro Glu Val Lys Phe
```

```
                305                 310                 315                 320
Asn Trp Tyr Val Asp Gly Val Glu Val His Asn Ala Lys Thr Lys Pro
                    325                 330                 335
Arg Glu Glu Gln Tyr Asn Ser Thr Tyr Arg Val Val Ser Val Leu Thr
                    340                 345                 350
Val Leu His Gln Asp Trp Leu Asn Gly Lys Glu Tyr Lys Cys Lys Val
                    355                 360                 365
Ser Asn Lys Ala Leu Pro Ala Pro Ile Glu Lys Thr Ile Ser Lys Ala
                370                 375                 380
Lys Gly Gln Pro Arg Glu Pro Gln Val Tyr Thr Leu Pro Pro Ser Arg
385                 390                 395                 400
Asp Glu Leu Thr Lys Asn Gln Val Ser Leu Thr Cys Leu Val Lys Gly
                    405                 410                 415
Phe Tyr Pro Ser Asp Ile Ala Val Glu Trp Glu Ser Asn Gly Gln Pro
                    420                 425                 430
Glu Asn Asn Tyr Lys Thr Thr Pro Pro Val Leu Asp Ser Asp Gly Ser
                    435                 440                 445
Phe Phe Leu Tyr Ser Lys Leu Thr Val Asp Lys Ser Arg Trp Gln Gln
                450                 455                 460
Gly Asn Val Phe Ser Cys Ser Val Met His Glu Ala Leu His Asn His
465                 470                 475                 480
Tyr Thr Gln Lys Ser Leu Ser Leu Ser Pro Gly Lys Phe Trp Val Leu
                    485                 490                 495
Val Val Val Gly Gly Val Leu Ala Cys Tyr Ser Leu Leu Val Thr Val
                    500                 505                 510
Ala Phe Ile Ile Phe Trp Val Arg Arg Val Lys Phe Ser Arg Ser Ala
                515                 520                 525
Asp Ala Pro Ala Tyr Gln Gln Gly Gln Asn Gln Leu Tyr Asn Glu Leu
                530                 535                 540
Asn Leu Gly Arg Arg Glu Glu Tyr Asp Val Leu Asp Lys Arg Arg Gly
545                 550                 555                 560
Arg Asp Pro Glu Met Gly Gly Lys Pro Arg Arg Lys Asn Pro Gln Glu
                    565                 570                 575
Gly Leu Tyr Asn Glu Leu Gln Lys Asp Lys Met Ala Glu Ala Tyr Ser
                    580                 585                 590
Glu Ile Gly Met Lys Gly Glu Arg Arg Arg Gly Lys Gly His Asp Gly
                    595                 600                 605
Leu Tyr Gln Gly Leu Ser Thr Ala Thr Lys Asp Thr Tyr Asp Ala Leu
                610                 615                 620
His Met Gln Ala Leu Pro Pro Arg Arg Ala Glu Gly Arg Gly Ser Leu
625                 630                 635                 640
Leu Thr Cys Gly Asp Val Glu Glu Asn Pro Gly Pro Met Glu Thr Asp
                    645                 650                 655
Thr Leu Ile Leu Trp Val Leu Leu Leu Val Pro Gly Ser Thr Gly
                    660                 665                 670
Gln Val Gln Leu Gln Gln Ser Gly Ala Glu Leu Ala Lys Pro Gly Ala
                675                 680                 685
Ser Val Lys Met Ser Cys Lys Thr Ser Gly Tyr Ser Phe Ser Ser Tyr
                690                 695                 700
Trp Met His Trp Val Lys Gln Arg Pro Gly Gln Gly Leu Glu Trp Ile
705                 710                 715                 720
Gly Tyr Ile Asn Pro Ser Thr Gly Tyr Thr Glu Asn Asn Gln Lys Phe
                    725                 730                 735
```

```
Lys Asp Lys Val Thr Leu Thr Ala Asp Lys Ser Ser Asn Thr Ala Tyr
            740                 745                 750

Met Gln Leu Asn Ser Leu Thr Ser Glu Asp Ser Ala Val Tyr Tyr Cys
            755                 760                 765

Ala Arg Ser Gly Arg Leu Tyr Phe Asp Val Trp Gly Ala Gly Thr Thr
            770                 775                 780

Val Thr Val Ser Ser Gly Gly Gly Gly Ser Gly Gly Gly Gly Ser Gly
785             790                 795                 800

Gly Gly Ser Gly Gly Gly Gly Ser Asp Ile Val Leu Thr Gln Ser
            805                 810                 815

Pro Pro Ser Leu Ala Val Ser Leu Gly Gln Arg Ala Thr Ile Ser Cys
            820                 825                 830

Arg Ala Ser Glu Ser Ile Asp Leu Tyr Gly Phe Thr Phe Met His Trp
            835                 840                 845

Tyr Gln Gln Lys Pro Gly Gln Pro Pro Lys Ile Leu Ile Tyr Arg Ala
            850                 855                 860

Ser Asn Leu Glu Ser Gly Ile Pro Ala Arg Phe Ser Gly Ser Gly Ser
865             870                 875                 880

Arg Thr Asp Phe Thr Leu Thr Ile Asn Pro Val Glu Ala Asp Asp Val
            885                 890                 895

Ala Thr Tyr Tyr Cys Gln Gln Thr His Glu Asp Pro Tyr Thr Phe Gly
            900                 905                 910

Gly Gly Thr Lys Leu Glu Ile Lys Ser Asp Pro Ala Thr Thr Thr Pro
            915                 920                 925

Ala Pro Arg Pro Pro Thr Pro Ala Pro Thr Ile Ala Ser Gln Pro Leu
            930                 935                 940

Ser Leu Arg Pro Glu Ala Cys Arg Pro Ala Ala Gly Gly Ala Val His
945             950                 955                 960

Thr Arg Gly Leu Asp Phe Ala Cys Asp Ile Val Val Ile Ser Val Gly
            965                 970                 975

Ser Met Gly Leu Ile Ile Ser Leu Leu Cys Val Tyr Phe Trp Leu Glu
            980                 985                 990

Arg Thr Met Pro Arg Ile Pro Thr Leu Lys Asn Leu Glu Asp Leu Val
            995                 1000                1005

Thr Glu Tyr His Gly Asn Phe Ser Ala Trp Ser Gly Val Ser Lys
    1010                1015                1020

Gly Leu Ala Glu Ser Leu Gln Pro Asp Tyr Ser Glu Arg Leu Cys
    1025                1030                1035

Leu Val Ser Glu Ile Pro Pro Lys Gly Gly Ala Leu Gly Glu Gly
    1040                1045                1050

Pro Gly Ala Ser Pro Cys Asn Gln His Ser Pro Tyr Trp Ala Pro
    1055                1060                1065

Pro Cys Tyr Thr Leu Lys Pro Glu Thr Gln Cys Thr Asn Tyr Ala
    1070                1075                1080

Leu Leu Lys Leu Ala Gly Asp Val Glu Ser Asn Pro Gly Pro Met
    1085                1090                1095

Glu Thr Asp Thr Leu Ile Leu Trp Val Leu Leu Leu Leu Val Pro
    1100                1105                1110

Gly Ser Thr Gly Gln Val Gln Leu Gln Gln Ser Gly Pro Glu Leu
    1115                1120                1125

Val Lys Pro Gly Ala Ser Val Lys Ile Ser Cys Lys Val Ser Gly
    1130                1135                1140
```

-continued

Tyr Ala Ile Ser Ser Ser Trp Met Asn Trp Val Lys Gln Arg Pro
    1145            1150            1155

Gly Gln Gly Leu Glu Trp Ile Gly Arg Ile Tyr Pro Gly Asp Gly
    1160            1165            1170

Asp Thr Lys Tyr Asn Gly Lys Phe Lys Asp Lys Ala Thr Leu Thr
    1175            1180            1185

Val Asp Lys Ser Ser Ser Thr Ala Tyr Met Gln Leu Ser Ser Leu
    1190            1195            1200

Thr Ser Val Asp Ser Ala Val Tyr Phe Cys Ala Arg Asp Gly Tyr
    1205            1210            1215

Arg Tyr Tyr Phe Asp Tyr Trp Gly Gln Gly Thr Ser Val Thr Val
    1220            1225            1230

Ser Ser Gly Gly Gly Gly Ser Gly Gly Gly Gly Ser Gly Gly Gly
    1235            1240            1245

Gly Ser Gly Gly Gly Gly Ser Asp Ile Val Met Thr Gln Thr Ala
    1250            1255            1260

Pro Ser Val Phe Val Thr Pro Gly Glu Ser Val Ser Ile Ser Cys
    1265            1270            1275

Arg Ser Ser Lys Ser Leu Leu His Ser Asn Gly Asn Thr Tyr Leu
    1280            1285            1290

Tyr Trp Phe Leu Gln Arg Pro Gly Gln Ser Pro Gln Leu Leu Ile
    1295            1300            1305

Tyr Arg Met Ser Asn Leu Ala Ser Gly Val Pro Asp Arg Phe Ser
    1310            1315            1320

Gly Ser Gly Ser Gly Thr Asp Phe Thr Leu Arg Ile Ser Arg Val
    1325            1330            1335

Glu Ala Glu Asp Val Gly Val Tyr Tyr Cys Met Gln His Leu Glu
    1340            1345            1350

Tyr Pro Val Thr Phe Gly Ala Gly Thr Lys Val Glu Ile Lys Ser
    1355            1360            1365

Asp Pro Ala Lys Ile Glu Val Met Tyr Pro Pro Pro Tyr Leu Asp
    1370            1375            1380

Asn Glu Lys Ser Asn Gly Thr Ile Ile His Val Lys Gly Lys His
    1385            1390            1395

Leu Cys Pro Ser Pro Leu Phe Pro Gly Pro Ser Lys Pro Pro Ile
    1400            1405            1410

Leu Leu Thr Ile Ser Ile Leu Ser Phe Phe Ser Val Ala Leu Leu
    1415            1420            1425

Val Ile Leu Ala Cys Val Leu Trp Lys Lys Arg Ile Lys Pro Ile
    1430            1435            1440

Val Trp Pro Ser Leu Pro Asp His Lys Lys Thr Leu Glu His Leu
    1445            1450            1455

Cys Lys Lys Pro Arg Lys Asn Leu Asn Val Ser Phe Asn Pro Glu
    1460            1465            1470

Ser Phe Leu Asp Cys Gln Ile His Arg Val Asp Asp Ile Gln Ala
    1475            1480            1485

Arg Asp Glu Val Glu Gly Phe Leu Gln Asp Thr Phe Pro Gln Gln
    1490            1495            1500

Leu Glu Glu Ser Glu Lys Gln Arg Leu Gly Gly Asp Val Gln Ser
    1505            1510            1515

Pro Asn Cys Pro Ser Glu Asp Val Val Ile Thr Pro Glu Ser Phe
    1520            1525            1530

Gly Arg Asp Ser Ser Leu Thr Cys Leu Ala Gly Asn Val Ser Ala

```
                    1535                1540                1545

Cys Asp Ala Pro Ile Leu Ser Ser Ser Arg Ser Leu Asp Cys Arg
    1550                1555                1560

Glu Ser Gly Lys Asn Gly Pro His Val Tyr Gln Asp Leu Leu Leu
    1565                1570                1575

Ser Leu Gly Thr Thr Asn Ser Thr Leu Pro Pro Pro Phe Ser Leu
    1580                1585                1590

Gln Ser Gly Ile Leu Thr Leu Asn Pro Val Ala Gln Gly Gln Pro
    1595                1600                1605

Ile Leu Thr Ser Leu Gly Ser Asn Gln Glu Glu Ala Tyr Val Thr
    1610                1615                1620

Met Ser Ser Phe Tyr Gln Asn Gln
    1625                1630

<210> SEQ ID NO 47
<211> LENGTH: 19
<212> TYPE: PRT
<213> ORGANISM: Artificial Sequence
<220> FEATURE:
<223> OTHER INFORMATION: signal sequence derived from human CD8a

<400> SEQUENCE: 47

Met Ser Leu Pro Val Thr Ala Leu Leu Leu Pro Leu Ala Leu Leu
1               5                   10                  15

His Ala Ala

<210> SEQ ID NO 48
<211> LENGTH: 4
<212> TYPE: PRT
<213> ORGANISM: Artificial Sequence
<220> FEATURE:
<223> OTHER INFORMATION: linker

<400> SEQUENCE: 48

Ser Asp Pro Ala
1

<210> SEQ ID NO 49
<211> LENGTH: 231
<212> TYPE: PRT
<213> ORGANISM: Artificial Sequence
<220> FEATURE:
<223> OTHER INFORMATION: human IgG1Fc spacer (HCH2CH3pvaa)

<400> SEQUENCE: 49

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110
```

```
Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 50
<211> LENGTH: 27
<212> TYPE: PRT
<213> ORGANISM: Artificial Sequence
<220> FEATURE:
<223> OTHER INFORMATION: transmembrane derived from human CD28

<400> SEQUENCE: 50

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 51
<211> LENGTH: 113
<212> TYPE: PRT
<213> ORGANISM: Artificial Sequence
<220> FEATURE:
<223> OTHER INFORMATION: endodomain derived from TCRz

<400> SEQUENCE: 51

Arg Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
        35                  40                  45

Lys Pro Arg Arg Lys Asn Pro Gln Glu Gly Leu Tyr Asn Glu Leu Gln
50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 52
<211> LENGTH: 20
<212> TYPE: PRT
<213> ORGANISM: Artificial Sequence
<220> FEATURE:
```

```
<223> OTHER INFORMATION: signal sequence derived from mouse kappa VIII

<400> SEQUENCE: 52

Met Glu Thr Asp Thr Leu Ile Leu Trp Val Leu Leu Leu Leu Val Pro
1               5                   10                  15

Gly Ser Thr Gly
            20

<210> SEQ ID NO 53
<211> LENGTH: 40
<212> TYPE: PRT
<213> ORGANISM: Artificial Sequence
<220> FEATURE:
<223> OTHER INFORMATION: human CD28STK spacer

<400> SEQUENCE: 53

Lys Ile Glu Val Met Tyr Pro Pro Pro Tyr Leu Asp Asn Glu Lys Ser
1               5                   10                  15

Asn Gly Thr Ile Ile His Val Lys Gly Lys His Leu Cys Pro Ser Pro
                20                  25                  30

Leu Phe Pro Gly Pro Ser Lys Pro
        35                  40

<210> SEQ ID NO 54
<211> LENGTH: 4
<212> TYPE: PRT
<213> ORGANISM: Artificial Sequence
<220> FEATURE:
<223> OTHER INFORMATION: furin cleavage site
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be Arg or Lys

<400> SEQUENCE: 54

Arg Xaa Xaa Arg
1

<210> SEQ ID NO 55
<211> LENGTH: 7
<212> TYPE: PRT
<213> ORGANISM: Artificial Sequence
<220> FEATURE:
<223> OTHER INFORMATION: consensus Tobacco Etch Virus (TEV) cleavage
      site

<400> SEQUENCE: 55

Glu Asn Leu Tyr Phe Gln Ser
1               5
```